(12) United States Patent
Crew et al.

(10) Patent No.: US 10,946,017 B2
(45) Date of Patent: Mar. 16, 2021

(54) TANK-BINDING KINASE-1 PROTACS AND ASSOCIATED METHODS OF USE

(71) Applicant: Arvinas Operations, Inc., New Haven, CT (US)

(72) Inventors: Andrew P. Crew, Guilford, CT (US); Jing Wang, Milford, CT (US); Hanqing Dong, Madison, CT (US); Yimin Qian, Plainsboro, NJ (US)

(73) Assignee: ARVINAS OPERATIONS, INC., New Haven, CT (US)

( * ) Notice: Subject to any disclaimer, the term of this patent is extended or adjusted under 35 U.S.C. 154(b) by 0 days.

(21) Appl. No.: 16/284,790

(22) Filed: Feb. 25, 2019

(65) Prior Publication Data

US 2019/0192514 A1 Jun. 27, 2019

Related U.S. Application Data

(63) Continuation of application No. 15/574,770, filed as application No. PCT/US2016/036036 on Jun. 6, 2016, now abandoned.

(60) Provisional application No. 62/171,299, filed on Jun. 5, 2015.

(51) Int. Cl.
| | |
|---|---|
| *A61K 31/506* | (2006.01) |
| *C07K 5/062* | (2006.01) |
| *C07D 417/04* | (2006.01) |
| *A61K 45/06* | (2006.01) |
| *C07D 413/04* | (2006.01) |
| *A61K 47/66* | (2017.01) |

(52) U.S. Cl.
CPC ............ *A61K 31/506* (2013.01); *A61K 45/06* (2013.01); *A61K 47/665* (2017.08); *C07D 413/04* (2013.01); *C07D 417/04* (2013.01); *C07K 5/06034* (2013.01); *A61K 2300/00* (2013.01)

(58) Field of Classification Search
CPC .... A61K 31/506; A61K 47/665; A61K 45/06; A61K 2300/00; C07D 413/04; C07D 417/04; C07K 5/06034
USPC ....................................................... 514/275
See application file for complete search history.

(56) References Cited

U.S. PATENT DOCUMENTS

| | | | |
|---|---|---|---|
| 6,306,663 B1 | 10/2001 | Kenten et al. |
| 6,670,348 B1 | 12/2003 | Rosen et al. |
| 7,030,141 B2 | 4/2006 | Bigge et al. |
| 7,041,298 B2 | 5/2006 | Deshaies et al. |
| 7,109,337 B2 | 9/2006 | Kath et al. |
| 7,208,157 B2 | 4/2007 | Sakamoto et al. |
| 7,244,851 B2 | 7/2007 | Cohen et al. |
| 7,345,081 B2 | 3/2008 | Cohen et al. |
| 7,419,975 B2 | 9/2008 | Palermo et al. |
| 7,517,906 B2 | 4/2009 | Condon et al. |
| 7,915,293 B2 | 3/2011 | Ramesh |
| 9,500,653 B2 | 11/2016 | Crews et al. |
| 9,632,089 B2 | 4/2017 | Crews et al. |
| 2006/0128632 A1 | 6/2006 | Sharma et al. |
| 2008/0051432 A1 | 2/2008 | Zhang |
| 2008/0214501 A1 | 9/2008 | Zhengying et al. |
| 2008/0269140 A1 | 10/2008 | Wang et al. |
| 2010/0056524 A1 | 3/2010 | McIver et al. |
| 2010/0203012 A1 | 8/2010 | Laurent et al. |
| 2011/0195043 A1 | 8/2011 | Sun et al. |
| 2012/0270800 A1 | 10/2012 | Verdine et al. |
| 2014/0235629 A1 | 8/2014 | Bartberger et al. |
| 2014/0243372 A1 | 8/2014 | Rew |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0291562 A1 | 10/2015 | Crew et al. |
| 2015/0344473 A1 | 10/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0368911 A1 | 12/2016 | Campos et al. |
| 2017/0008904 A1 | 1/2017 | Crew et al. |

(Continued)

FOREIGN PATENT DOCUMENTS

| | | |
|---|---|---|
| CN | 1844118 A | 10/2006 |
| CN | 103688176 A | 3/2014 |

(Continued)

OTHER PUBLICATIONS

Ahn, et al., "HIF-lalpha peptide derivatives with modifications at the hydroxyproline residue as activators of HIF-lalpha", Bioorg Med Chem Lett. 19(15), 2009, 4403-4405.

(Continued)

*Primary Examiner* — Kristin A Vajda

(74) *Attorney, Agent, or Firm* — Bryan D. Zerhusen, Esq.; Nicholas R. Herrel, Esq.; Cantor Colburn LLP

(57) ABSTRACT

The present invention relates to bifunctional compounds, which find utility to degrade and (inhibit) TBK1. In particular, the present invention is directed to compounds, which contain on one end an E3 ubiquitin ligase binding moiety which binds to an E3 ubiquitin ligase and on the other end a moiety which binds TBK1 such that TBK1 is placed in proximity to the ubiquitin ligase to effect degradation (and inhibition) of TBK1. The present invention exhibits a broad range of pharmacological activities associated with compounds according to the present invention, consistent with the degradation/inhibition of TBK1.

21 Claims, 8 Drawing Sheets

(56) References Cited

U.S. PATENT DOCUMENTS

| | | |
|---|---|---|
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0237418 A1 | 8/2018 | Crew et al. |
| 2018/0256586 A1 | 9/2018 | Crew et al. |

FOREIGN PATENT DOCUMENTS

| | | |
|---|---|---|
| EP | 2985285 | 2/2016 |
| JP | A 2004-525889 | 8/2004 |
| JP | A 2010-502627 | 1/2010 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 2000/066119 | 11/2000 |
| WO | WO 2002/066512 | 8/2002 |
| WO | WO 2002/100845 | 12/2002 |
| WO | WO 2005/097791 | 10/2005 |
| WO | WO 2006/069063 | 6/2006 |
| WO | WO 2006/113942 | 10/2006 |
| WO | WO 2007/101347 | 9/2007 |
| WO | WO 2007/106670 | 9/2007 |
| WO | WO 2007/130626 | 11/2007 |
| WO | WO 2008/011392 | 1/2008 |
| WO | WO 2008/014236 | 1/2008 |
| WO | WO 2008/109057 | 9/2008 |
| WO | WO 2008/128121 | 10/2008 |
| WO | WO 2008/128171 | 10/2008 |
| WO | WO 2008/134679 | 11/2008 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2011/008260 | 1/2011 |
| WO | WO 2012/003281 | 1/2012 |
| WO | WO 2012/040527 | 3/2012 |
| WO | WO 2012/078559 | 6/2012 |
| WO | WO 2012/090104 | 7/2012 |
| WO | WO 2013/071035 | 5/2013 |
| WO | WO 2013/071039 | 5/2013 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/038606 | 3/2014 |
| WO | WO 2014/047024 | 3/2014 |
| WO | WO 2014/055461 | 4/2014 |
| WO | WO 2014/074658 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2015/000868 | 1/2015 |
| WO | WO 2015/006524 | 1/2015 |
| WO | WO 2015/160845 | 10/2015 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197114 | 12/2016 |
| WO | WO 2017/011590 | 1/2017 |
| WO | WO 2017/030814 | 2/2017 |
| WO | WO 2017/079267 | 5/2017 |
| WO | WO 2017/185036 | 10/2017 |
| WO | WO 2017/197051 | 11/2017 |

OTHER PUBLICATIONS

Ardecky, RJ, et al., "Design, synthesis and evaluation of inhibitor of apoptosis protein (IAP) antagonists that are highly selective for the BIR2 domain of XIAP", Bioorg. Med. Chem., 23(14): 4253-4257 (2013).

Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).

Bargagna-Mohan, et al., "Use of PROTACS as molecular probes of angiogenesis", Bioorg Med Chem Left. 15(11) 2005, 2724-2727.

Bondeson, et al., (2017) "Targeted Protein Degradation by Small Molecules." *Annu Rev Pharmacol Toxicol* 57:107-123.

Bondeson, et al., "Catalytic in vivo protein knockdown by small-molecule PROTACS", National Chem Biol. 11(8) Aug. 2015, 611-617.

Buckley, et al., "HaloPROTACS: use of small molecule PROTACS to induce degradation of HaloTag fusion proteins", ACS Chem Biol. 10(8), 2015, 1831-1837.

Buckley, et al., "Small-molecule inhibitors of the interaction between the E3 ligase VHL and H1Fla", Angew Chem Int Ed Engl.51(46), Oct. 12, 2012 11463-11467.

Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.

Burslem, et al., (2017) "Small-Molecule Modulation of Protein Homeostasis." *Chem Rev* 117(17):11269-11301.

Capitosti, S., et al., "Thalidomide analogues demonstrate dual inhibition of both angiogenesis and prostate cancer", Bioorganic & Medicinal Chemistry 12, (2004) 327-336.

Carmony, KC, et al., "PROTAC-Induced Proteolytic Targeting", Methods Mol. Biol., 2012, vol. 832, pp. 627-638.

CAS Registry No. 1004933-70-3, which entered STN on Feb. 21, 2008.

CAS Registry No. 871986-52-6 entered STN Jan. 16, 2006.

Chene, P., et al., "Inhibiting the p53-MDM2 interaction: an important target for cancer therapy" Nat. Rev. Cancer (2003), 3, 102-109.

Cohen, F, et al., "Orally bioavailable antagonists of inhibitor of apoptosis proteins based on an azabicyclooctane scaffold", J. Med. Chem., 52(6), 1723-1730 (2009).

Cohen, F. et al., "Antogonists of inhibitors of apoptosis proteins based on thiazole amide isosteres", Bioorg. Med. Chem. Lett., 20(7), 2229-2233 (2010).

Contino-Pepin, Christiane, et al., "Preliminary biological evaluations of new thalidomide analogues for multiple sclerosis application", Bioorganic & Medicinal Chemistry Letter 19 (2009), 878-881.

Corson, et al., "Design and applications of bifunctional small molecules: why two heads are better than one", ACS Chemical Biology vol. 3 No. 11, pp. 677-692; Nov. 21, 2008.

Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (2010).

Cromm, et al., (2017) "Targeted Protein Degradation: from Chemical Biology to Drug Discovery." *Cell Chem Biol* 24(9):1181-1190.

(56) References Cited

OTHER PUBLICATIONS

Cyrus, et al., "Jostling for position: optimizing linker location in the design of estrogen receptor-targeting PROTACs", Chem Med Chem. 5(7), Jul. 5, 2010 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed PROTAC: An Effective New Tool for Targeted Protein Degradation," Chembiochem., 2010, vol. 11, pp. 1531-1534.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al).
Dixon, S. J. et al., "Identifying druggable disease-modifying gene products",. *Curr Opin Chem Biol* 13, 549-555, doi:S1367-5931(09)00107-0 [pii] 10.1016/j.cbpa.2009.08.003 (2009).
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 ( 2010).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hon, et al., "Structural basis for the recognition of hydroxyproline in Hlf-1 alpha by pVHL", Nature 417, Jun. 27, 2002 975-978.
Huang, et al., (2016) "Drugging the undruggables: exploring the ubiquitin system for drug development." Cell Res 26(4):484-498.
Hughes, et al., (2017) "Molecular recognition of ternary complexes: a new dimension in the structure-guided design of chemical degraders." *Essays Biochem* 61(5):505-516.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Kim, K.S., "Discovery of tetrahydroisoquinoline-based bivalent heterodimeric IAP antagonists", Bioorg. Med. Chem. Lett. 24(21), 5022-5029 (2014).
Knott, Edward (1955). "Compounds containing sulphur chromophores. Part I. The action of bases on heterocyclic sulphide quarternary salts", Journal of The Chemical Society (resumed). 10.1039/jr9550000916. 949-954) (USPTO summary attached).

Kronke, et al, "Lenalidomide Causes Selective Degradation of IKZF1 and IKZF3 in Multiple Myeloma Cells", Science 343, 301-305 (2014).
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012).
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Maniaci C, et al. (2017) "Homo-PROTACs: bivalent small-molecule dimerizers of the VHL E3 ubiquitin ligase to induce self-degradation." *Nat Commun* 8(1):830 1-13.
Mannhold, R., et al., "IAP antagonists: promising candidates for cancer therapy", Drug Discov. Today, 15 (5-6), 210-219 (2010).
Medline Plus Trusted Health Information for You, wwv.nlm.nih.gov/medlineplus/cancer.html pp. 1-10, (2007).
Min, Jung-hyun, et al., "Structure of an HIV-1-alpha—pVHL complex: hydroxyproline recognition in signaling", Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (2015) 23, 2360-2367.
Muller, G., et al., "Amino- Substituted Thalodomide Analogs: Potent Inhibitors of TNF-α Production", Bioorganic & Medicinal Chemistry Letters 9 (1999) 1625-1630.
Ndubaku, C, et al., "Antagonism of c-Iap and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (2012).
Nikolovska-Coleska, et al., "Interaction of a cyclic, Bivalent Smac Mimetic with the X-linked inhibitor of apoptosis protein", Biochemistry, 2008, 47(37), pp. 9811-9824.
Oost, T.K. et al., "Discovery of potent antagonists of the antiapoptotic protein XIAP for the treatment of cancer", Journal of Medicinal Chemistry 2004, 47, 4417-4426.
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Perez, HL,"Discovery of potent heterodimeric antagonists of inhibitor of apoptosis proteins (IAPs) with sustained antitumor activity", J. Med. Chem. 58(3), 1556-1562 (2015).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.

(56) References Cited

OTHER PUBLICATIONS

Raina, et al., (2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014 PubMed PMID: 25384157. (J. Med. Chem. (2014) 57, 10499-10511 Rew, et al.).
Richters, A., et al., "Identification and further development of potent TBK1 inhibitors", ACS Chemical Biology, vol. 10, No. 1, Jan. 16, 2015, pp. 289-298 (2015).
Rodriguez-Gonzalez, et al., "Targeting steroid hormone receptors for ubiquitination and degradation in breast and prostate cancer", Oncogene. 27(57), Dec. 4, 2008 7201-7211.
Rotili, D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Ghemical Proteomics", Bioorg Med Chem Lett. 18(22), Nov. 15, 2008 5904-5908.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017.
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.

Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Suzuki et al. "Severe impairment of interleukin-1 and toll-like receptor signaling in mice lacking IRAK-4", Nature, 416(6882), 2002, 750-756.
Toure, et al., (2016) "Small-Molecule PROTACS: New Approaches to Protein Degradation." *Angew Chem Int Ed Engl* 55(6):1966-1973.
Turk, B. E., "Binding of thalidomide to alphal-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Molle, et al., "Dissecting fragment-based lead discovery at the von Hippel-Lindau protein:hypoxia inducible factor la protein-protein interface", Chem Biol. 19(10), Oct. 26, 2012 1300-1312.
Vassilev, et al., "In vivo activation of the p53 pathway by small-molecule antagonists of MDM2", Science 303, Feb. 6, 2004 844-848.
Vazquez, A. et al., "The genetics of the p53 pathway, apoptosis and cancer therapy", Nat. Rev. Drug. Dis., 7, 979-982 (2008).
Vu, B. et al. "Discovery of RG7112: a small-molecule MDM2 inhibitor in clinical development", ACS Med. Chem. Lett. (2013) 4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.
Winter, et al., "Phthalimide Conjugation as a strategy for in vivo target protein degradation", Science, 2015 vol. 348 (6241), pp. 1376-1381 [Pub online: May 21, 2015].
Zengerle, et al., "Selective Small Molecule Induced Degradation of the BET Bromodomain Protein BRD4" ACS Chemical Biology, Jun. 2, 2015, vol. 10, pp. 1770-1777.
Zhang B.et al., "Small-molecule MDM2-p53 inhibitors: recent advances", Future Med. Chem. (2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (2017).
U.S. Appl. No. 15/574,770, filed Nov. 16, 2017, US 2018-0147202.

TANK-BINDING KINASE-1 PROTACS AND ASSOCIATED METHODS OF USE

CROSS-REFERENCE TO RELATED APPLICATIONS

The present disclosure is a Continuation Application of U.S. patent application Ser. No. 15/574,770, filed 16 Nov. 2017, entitled: TANK-BINDING KINASE-1 PROTACs AND ASSOCIATED METHODS OF USE, which is a National Stage of PCT/US2016/036036, filed 6 Jun. 2016, entitled TANK-BINDING KINASE-1 PROTACs AND ASSOCIATED METHODS OF USE, and which claims priority to the U.S. Provisional Application No. 62/171,299, filed Jun. 5, 2015, all of which are incorporated herein by reference in their entirety for all purposes.

BACKGROUND

Field of the Discovery

1. Field of the Discovery

The description provides bifunctional compounds and associated methods of use. The bifunctional compounds are useful as modulators of targeted ubiquitination, especially with respect to a variety of polypeptides and other proteins, which are degraded and/or otherwise inhibited by bifunctional compounds according to the present invention.

2. Background Information

The most common therapeutic interventions available to the prescribing physician are inhibitor-based drugs such that the active pharmaceutical ingredient mediates the function of the aberrant protein via direct or allosteric inhibition of the mechanistic activity of said protein.

Although inhibition of protein activity is a clinically validated approach there are significant constraints to its wider applicability. Firstly, it carries the burden of requiring protracted target engagement for the mechanism and consequential function to be effectively abrogated. Many protein-small molecule interactions are associated with rapid off-rates, resulting in very low inhibitor occupancy of the protein active site and inadequate downregulation of downstream signaling.

Secondly, inability to reach tolerated free-drug concentrations at or above the in vitro $IC_{90}$, either because of high plasma protein binding, poor pharmacokinetics, or toxicity can limit the effectiveness of inhibitor drugs.

Finally, many proteins possess little or no mechanistic activity, yet execute their biological role by providing a scaffolding function. As a result, these proteins are less susceptible to the inhibitor paradigm.

E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped.

Technologies that can reduce levels of a target protein in a manner that requires only transient interactions with the protein could provide significant therapeutic utility.

SUMMARY

Proteolysis Targeting Chimeras (PROTACs) (Corson, T. W.; Aberle, N.; Crews, C. M. *ACS Chem. Biol.* 2008 3(11) 677-692; Sakamoto, K. M.; Kim, K. B.; Verma, R.; Ransick, A.; Stein, B.; Crews, C. M.; Deshaies, R. J. *Mol. Cell. Proteomics* 2003 2(12) 1350-1358; Sakamoto, K. M.; Kim, K. B.; Kumagai, A.; Mercurio, F.; Crews, C. M.; Deshaies, R. J. *Proc. Natl. Acad. Sci. USA* 2001 98(15) 8554-8559) are a class of bifunctional molecules that live in the "beyond rule of 5" (bRo5) (Barbie, D. A.; Tamayo, P.; Boehm, J. S.; Kim, S. Y.; Moody, S. E.; Dunn, I. F.; Schinzel, A. C.; Sandy, P.; Meylan, E.; Scholl, C.; et al. *Nature* 2009 462 108-112) space that hijack the endogenous protein homeostasis machinery via recruitment of an E3 ubiquitin ligase via one component ligand and associating it with a target protein of interest (PoI) through another component ligand to mediate ubiquitin transfer to, and degradation of, the latter via the proteasome (FIG. 1).

The present disclosure describes compounds, including compositions comprising the same, which function to recruit endogenous proteins to an E3 ubiquitin ligase enzyme, e.g., Von Hippel-Lindau (VHL) E3 ubiquitin ligase, cereblon, IAP (XIAP), and MDM2, for ubiquitination and subsequent degradation, and methods of using the same. In particular, the present disclosure provides bifunctional or proteolysis targeting chimeric (PROTAC) compounds, which find utility as modulators of targeted ubiquitination and degradation of TANK-binding kinase 1 (TBK1).

Thus, in one aspect, the disclosure provides compounds which function to recruit endogenous proteins, e.g., TBK1 proteins, to E3 Ubiquitin Ligase for ubiquitination and degradation. In certain embodiments, the compounds have the following general structure:

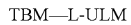

TBM—L—ULM  (I), wherein TBM is an TBK1 binding moiety, ULM is an E3 ligase binding moiety, e.g., a VHL E3 ligase binding moiety (VLM), cereblon binding moiety (CLM), XIAP binding moiety, or MDM2 binding moiety, and L is a bond or a linker moiety which links the TBM and ULM.

As such, in certain embodiments, the description provides compounds having the following general structure:

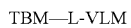

TBM—L—VLM  (II), wherein TBM is an TBK1 binding moiety, VLM is a VHL E3 ligase binding moiety and L is a bond or a linker moiety which links the TBM and VLM.

It will be understood that the general structures are exemplary and the respective moieties can be arranged spatially in any desired order or configuration, e.g., ULM-L-TBM, and VLM-L-TBM respectively.

In certain additional embodiments, the compounds comprise a plurality of E3 ligase binding moieties and/or a plurality of TBMs.

In certain embodiments, the description provides a bifunctional compound having a structure as described herein, a salt, a polymorph, and a prodrug thereof.

In another aspect, the description provides compositions comprising compounds as described herein, and a pharmaceutically acceptable carrier. In certain embodiments, the compositions are therapeutic or pharmaceutical compositions comprising an effective amount of a compound as described herein and a pharmaceutically acceptable carrier. In certain embodiments, the therapeutic or pharmaceutical compositions comprise an additional biologically active agent, e.g., an agent effective for the treatment of cancer.

In any of the aspects or embodiments described herein, the therapeutic compositions comprising compounds described herein can be in any suitable dosage form, e.g., solid, or liquid, and configured to be delivered by any suitable route, e.g., oral, parenteral, intravenous, intraperitoneal, subcutaneous, intramuscular, etc.

In another aspect, the disclosure provides methods of modulating protein ubiquitination and degradation in a subject, e.g., a cell, a tissue, mammal, or human patient, the method comprising administering an effective amount of a compound as described herein or a composition comprising an effective amount of the same to a subject, wherein the compound or composition comprising the same is effective in modulating protein ubiquitination and degradation of the protein in the subject. In certain embodiments, the protein is TBK1.

In another aspect, the disclosure provides methods of modulating TBK1 protein ubiquitination and degradation in a subject, e.g., a cell, a tissue, mammal, or human patient, the method comprising administering an effective amount of a compound as described herein or a composition comprising an effective amount of the same to a subject, wherein the compound or composition comprising the same is effective in modulating TBK1 protein ubiquitination and degradation of the protein in the subject.

In another aspect, the disclosure provides methods of treating or ameliorating a symptom of a disease related to TBK1 activity in a subject, e.g., a cell, a tissue, mammal, or human patient, the method comprising administering an effective amount of a compound as described herein or a composition comprising an effective amount of the same to a subject in need thereof, wherein the compound or composition comprising the same is effective in treating or ameliorating a symptom of a disease related to TBK1 activity in the subject. In a preferred embodiment, the subject is a human.

In another aspect, the disclosure provides methods for identifying the effects of the degradation of proteins of interest in a biological system using compounds according to the present invention.

In another aspect, the description provides kits comprising compounds or compositions as described herein. The kit may be promoted, distributed, or sold as a unit for performing the methods of the present invention. In addition, the kits of the present invention may preferably contain instructions which describe a suitable use. Such kits can be conveniently used, e.g., in clinical settings, to treat patients.

Where applicable or not specifically disclaimed, any one of the embodiments described herein are contemplated to be able to combine with any other one or more embodiments, even though the embodiments are described under different aspects of the invention. As such, the preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1:
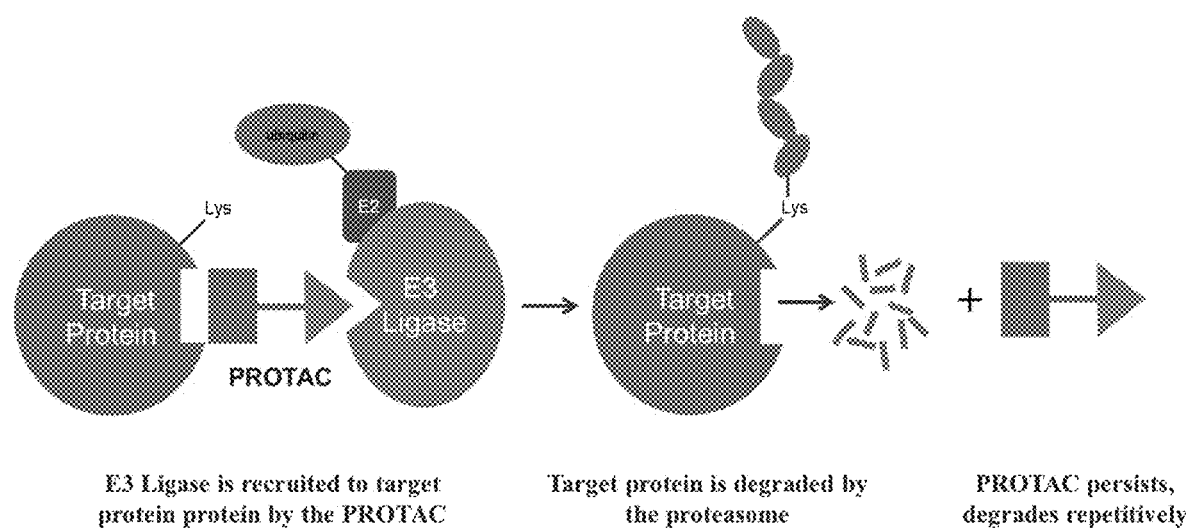
FIG. 1. Proteolysis Targeting Chimeras (PROTACs) recruit an E3 ligase to a target protein to facilitate ubiquitin transfer from the former to the latter.

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The present description relates to the surprising and unexpected discovery that an E3 ubiquitin ligase protein can ubiquitinate a target protein once the E3 ubiquitin ligase protein and the target protein are brought into proximity by a chimeric construct (e.g., PROTAC) as described herein, which binds the E3 ubiquitin ligase protein and the target protein. Accordingly, the present description provides compounds, compositions comprising the same, and associated methods of use for ubiquitination and degradation of a chosen target protein, e.g., TBK1 (See FIG. 1).

The present description is related in certain aspects to U.S. Patent Publication 2014/0356322A1, which is incorporated herein by reference in its entirety for all purposes.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The term "about" and the like, as used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the phrase "about " is normally used to encompass values within the standard deviation or standard error.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" can refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anticancer agent. In particularly preferred aspects, the co-administration of compounds results in synergistic activity and/or therapy, including anticancer activity.

The term "effective" can mean, but is in no way limited to, that amount/dose of the active pharmaceutical ingredient, which, when used in the context of its intended use, effectuates or is sufficient to prevent, inhibit the occurrence, ameliorate, delay or treat (alleviate a symptom to some extent, preferably all) the symptoms of a condition, disorder or disease state in a subject in need of such treatment or receiving such treatment. The term effective subsumes all other effective amount or effective concentration terms, e.g., "effective amount/dose," "pharmaceutically effective amount/dose" or "therapeutically effective amount/dose," which are otherwise described or used in the present application.

The effective amount depends on the type and severity of disease, the composition used, the route of administration, the type of mammal being treated, the physical characteristics of the specific mammal under consideration, concurrent medication, and other factors which those skilled in the medical arts will recognize. The exact amount can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "pharmacological composition," "therapeutic composition," "therapeutic formulation" or "pharmaceutically acceptable formulation" can mean, but is in no way limited to, a composition or formulation that allows for the effective distribution of an agent provided by the invention, which is in a form suitable for administration to the physical location most suitable for their desired activity, e.g., systemic administration.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

The term "local administration" refers to a route of administration in which the agent is delivered to a site that is apposite or proximal, e.g., within about 10 cm, to the site of the lesion or disease.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described.

It is understood by those of ordinary skill that molecules which are described herein are stable compounds as generally described hereunder. When the bond  is shown, both a double bond and single bond are represented within the context of the compound shown.

As used herein, "derivatives" can mean compositions formed from the native compounds either directly, by modification, or by partial substitution. As used herein, "analogs" can mean compositions that have a structure similar to, but not identical to, the native compound.

The term "Ubiquitin Ligase" refers to a family of proteins that facilitate the transfer of ubiquitin to a specific substrate protein, targeting the substrate protein for degradation. For example, Von Hippel-Lindau E3 Ubiquitin Ligase or VCB E3 Ubiquitin Ligase is protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "subject" is used throughout the specification to describe a cell, tissue, or animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

Compounds

In one aspect, the present invention provides compounds useful for regulating protein activity. The composition comprises a ubiquitin pathway protein binding moiety (preferably for an E3 ubiquitin ligase, alone or in complex with an E2 ubiquitin conjugating enzyme which is responsible for the transfer of ubiquitin to targeted proteins) according to a defined chemical structure and a protein targeting moiety which are linked or coupled together, preferably through a linker, wherein the ubiquitin pathway protein binding moiety recognizes an ubiquitin pathway protein and the targeting moiety recognizes a target protein (e.g., TBK1).

In certain embodiments, the disclosure provides compounds which function to recruit TBK1 proteins to E3 Ubiquitin Ligase for ubiquintination and degradation. In certain embodiments, the compounds have the following general structure:

$$TBM—L-ULM \quad (I),$$

wherein ULM is an E3 ligase binding moiety, e.g., a moiety that binds a member selected from the group of Von Hippel-Lindau (VHL) E3 ubiquitin ligase, cereblon, IAP (XIAP), and MDM2, TBM is a TBK1 binding moiety, which binds to a TBK1 protein and L is a bond or a chemical linker moiety which links the TBM and ULM.

Without being bound by any particular theory, it is hypothesized that due at least in part to the proximity of TBK1 and the E3 ubiquitin ligase, the TBK1 is ubiquitinated by the ubiquitin ligase and degraded. In certain embodiments, the TBM is chemically linked or coupled directly to the ULM group. In certain additional embodiments, the TBM is chemically linked or coupled to the ULM via a chemical linker moiety.

The von Hippel-Lindau (VHL) tumor suppressor. VHL comprises the substrate recognition subunit/E3 ligase complex VCB, which includes elongins B and C, and a complex including Cullin-2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. We generated the first small molecule ligands of Von Hippel Lindau (VHL) to the substrate recognition subunit of the E3 ligase, VCB, an important target in cancer, chronic anemia and ischemia, and obtained crystal structures confirming that the compound mimics the binding mode of the transcription factor HIF-1α, the major substrate of VHL.

Inhibitors of Apoptosis Protein (IAPs) are guardian ubiquitin ligases that keep classic pro-apoptotic proteins in check, and regulates not only caspases and apoptosis, but also modulates inflammatory signaling and immunity, copper homeostasis, mitogenic kinase signaling, cell proliferation, as well as cell invasion and metastasis. IAPs act as a direct caspase inhibitor, and directly bind to the active site pocket of CASP3 and CASP7 and obstruct substrate entry. IAPS also inactivate CASP9 by keeping it in a monomeric, inactive state. IAP acts as an E3 ubiquitin-protein ligase regulating NF-kappa-B signaling and the target proteins for its E3 ubiquitin-protein ligase activity include: RIPK1, CASP3, CASP7, CASP8, CASP9, MAP3K2/MEKK2, DIABLO/SMAC, AIFM1, CCS and BIRC5/survivin. Ubiquitination of CCS leads to enhancement of its chaperone activity toward its physiologic target, SOD1, rather than proteasomal degradation. Ubiquitinion of MAP3K2/MEKK2 and AIFM1 does not lead to proteasomal degradation. IAP plays a role in copper homeostasis by ubiquitinating COMMD1 and promoting its proteasomal degradation, and can also function as E3 ubiquitin-protein ligase of the NEDD8 conjugation pathway, targeting effector caspases for neddylation and inactivation. IAP regulates the BMP signaling pathway and the SMAD and MAP3K7/TAK1 dependent pathways leading to NF-kappa-B and JNK activation.

IAPs are an important regulator of innate immune signaling via regulation of Nodlike receptors (NLRs), and protects cells from spontaneous formation of the ripoptosome, a large multi-protein complex that has the capability to kill cancer cells in a caspase-dependent and caspase-independent manner. Suppresses ripoptosome formation by ubiquitinating RIPK1 and CASP8. Acts as a positive regulator of Wnt signaling and ubiquitinates TLE1, TLE2, TLE3, TLE4 and AES. Ubiquitination of TLE3 results in inhibition of its interaction with TCF7L2/TCF4 thereby allowing efficient recruitment and binding of the transcriptional coactivator beta-catenin to TCF7L2/TCF4 that is required to initiate a Wnt-specific transcriptional program. Inhibitors of the IAP, which are useful in making compounds as described herein, are known in the art.

Mouse double minute 2 homolog (MDM2) also known as E3 ubiquitin-protein ligase Mdm2 is a protein that in humans is encoded by the MDM2 gene. Mdm2 is an important negative regulator of the p53 tumor suppressor. Mdm2 protein functions both as an E3 ubiquitin ligase that recognizes the N-terminal trans-activation domain (TAD) of the p53 tumor suppressor and an inhibitor of p53 transcriptional activation. Inhibitors of the MDM2-p53 interaction, which are useful in making compounds as described herein, include the cis-imidazoline analog nutlin.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Thalidomide, which has been approved for the treatment of a number of immunological indications, has also been approved for the treatment of certain neoplastic diseases, including multiple myeloma. In addition to multiple myeloma, thalidomide and several of its analogs are also currently under investigation for use in treating a variety of other types of cancer. While the precise mechanism of thalidomide's anti-tumor activity is still emerging, it is known to inhibit angiogenesis. Recent literature discussing the biology of the imides includes Lu et al Science 343, 305 (2014) and Krönke et al Science 343, 301 (2014).

Significantly, thalidomide and its analogs e.g. pomolinamiode and lenalinomide, are known to bind cereblon. These agents bind to cereblon, altering the specificity of the complex to induce the ubiquitination and degradation of Ikaros (IKZF1) and Aiolos (IKZF3), transcription factors essential for multiple myeloma growth. Indeed, higher expression of cereblon has been linked to an increase in efficacy of imide drugs in the treatment of multiple myeloma. Therefore, thalidomide and its analogs are useful cereblon binding moieties for use in making compounds as described herein.

In additional embodiments, the description provides compounds having the following general structure:

wherein TBM is a TBK1 binding moiety and VLM is a Von Hippel-Lindau E3 Ubiquitin Ligase binding moiety, and L is a bond or a chemical linker moiety which links the TBM and VLM. The ULM or VLM group and TBM group may be covalently linked to the linker group through any covalent bond which is appropriate and stable to the chemistry of the linker.

In certain embodiments, the bifunctional compound further comprises a chemical linker ("L"). In this example, the structure of the bifunctional compound can be depicted as:

wherein TBM is a TBK1 binding moiety, L is a linker, and CLM is a cereblon E3 ubiquitin ligase binding moiety.

It will be understood that the general structures are exemplary and the respective moieties can be arranged in any desired order or configuration, e.g., ULM-L-TBM, and VLM-L-TBM respectively. In certain additional embodiments, the compounds comprise a plurality of E3 ligase binding moieties and/or a plurality of TBMs.

In any of the aspects or embodiments of compounds described herein, unless indicated otherwise, the compounds are intended to encompass pharmaceutically acceptable salts, enantiomers, stereoisomers, solvates or polymorphs thereof.

Exemplary ULMs

In certain embodiments of the compounds as described herein, the ULM comprises a chemical structure selected from the group ULM-a:

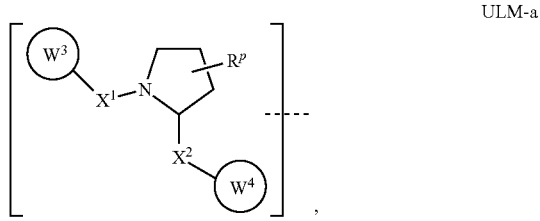

wherein:
a dashed line indicates the attachment of at least one TBM, another ULM or VLM (i.e., ULM' or VLM'), or a chemical linker moiety coupling at least one TBM, a ULM' or VLM' to the other end of the linker;
$X^1$, $X^2$ are each independently a bond, O, $NR^{Y3}$, $CR^{Y3}R^{Y4}$, C=O, C=S, SO, $SO_2$;

$R^{Y3}$, $R^{Y4}$ are each independently H, $C_{1-6}$ alkyl (linear, branched, optionally substituted by 1 or more halo, $C_{1-6}$ alkoxyl);
optionally substituted by 1-3 $R^P$ groups in the pyrrolidine moiety, wherein each $R^P$ is independently H, halo, —OH, $C_{1-3}$alkyl;
$W^3$ is an optionally substituted —T-N($R^{1a}R^{1b}$) —T-Aryl, an optionally substituted —T-Heteroaryl, an optionally substituted —T-Heterocycle, an optionally substituted —$NR^1$-T-Aryl, an optionally substituted —$NR^1$-T-Heteroaryl or an optionally substituted —$NR^1$-T-Heterocycle, where T is covalently bonded to $X^1$;
each $R^1$, $R^{1a}$, $R^{1b}$ is independently H, a $C_1$-$C_6$ alkyl group (linear, branched, optionally substituted by 1 or more halo, —OH), $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, N($R^{Y3}R^{Y4}$)$SO_2$;
T is an optionally substituted —$(CH_2)_n$— group, wherein each one of the methylene groups may be optionally substituted with one or two substituents, preferably selected from halogen, a $C_1$-$C_6$ alkyl group (linear, branched, optionally substituted by 1 or more halogen, —OH) or the sidechain of an amino acid as otherwise described herein, preferably methyl, which may be optionally substituted; and n is 0 to 6, often 0, 1, 2, or 3, preferably 0.
Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted; and
$W^4$ is an optionally substituted —$NR^1$-T-Aryl, an optionally substituted —$NR^1$-T-Heteroaryl group or an optionally substituted —$NR^1$-T-Heterocycle, where where —$NR^1$ is covalently bonded to $X^2$; $R^1$ is H or $CH_3$, preferably H, and T is an optionally substituted —$(CH_2)_n$— group, wherein each one of the methylene groups may be optionally substituted with one or two substituents, preferably selected from halogen, an amino acid sidechain as otherwise described herein or a $C_1$-$C_6$ alkyl group (linear, branched, optionally substituted by 1 or more halo, —OH), preferably one or two methyl groups, which may be optionally substituted; and n is 0 to 6, often 0, 1, 2 or 3, preferably 0 or 1.
Alternatively, T may also be a —$(CH_2O)_n$— group, a —$(OCH_2)_n$— group, a —$(CH_2CH_2O)_n$— group, a —$(OCH_2CH_2)_n$— group, all of which groups are optionally substituted.

In any of the embodiments described herein, $W^3$ and/or $W^4$ can be attached to a linker moiety as described herein.

In certain embodiments, aryl groups for $W^3$ include optionally substituted phenyl or naphthyl groups, preferably phenyl groups, wherein the phenyl or naphthyl group is optionally substituted with a linker group to which is attached a TBM group (including a ULM' group) and/or a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and $R_2$ are the same as for $R^1$), a halogen (often F or Cl), OH, $CH_3$, $CF_3$, OMe, $OCF_3$, $NO_2$—CN or a $S(O)_2R_S$ group ($R_S$ is a a $C_1$-$C_6$ alkyl group, an optionally substituted aryl, heteroaryl or heterocycle group or a —$(CH_2)_m NR_1R_2$ group), each of which may be substituted in ortho-, meta- and/or para-positions of the phenyl ring, preferably para-), or an Aryl (preferably phenyl), heteroaryl or heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a TBM group (including a ULM' group), wherein the substitution occurs in ortho-, meta- and/or para-positions of the phenyl ring, preferably para-, a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo- (preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally substituted with a linker group to which is attached a TBM group (including a ULM' group).

In certain embodiments, heteroaryl groups for $W^3$ include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

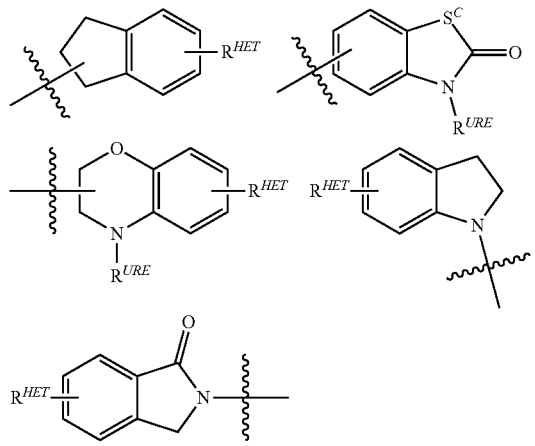

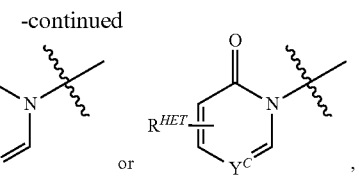

wherein:
$S^c$ is $CHR^{SS}$, $NR^{URE}$, or O;
$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted; and
$Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C-$R_a$ where $R_a$ is H or a $C_1$-$C_6$ alkyl group (preferably $C_1$-$C_3$ alkyl). Each of said heteroaryl groups may be optionally substituted with a linker group to which is attached a TBM group (including a ULM' group).

In additional embodiments, heterocycle groups for $W^3$ include tetrahydroquinoline, piperidine, piperazine, pyrrolidine, morpholine, tetrahydrofuran, tetrahydrothiophene, oxane and thiane, each of which groups may be optionally substituted or a group according to the chemical structure:

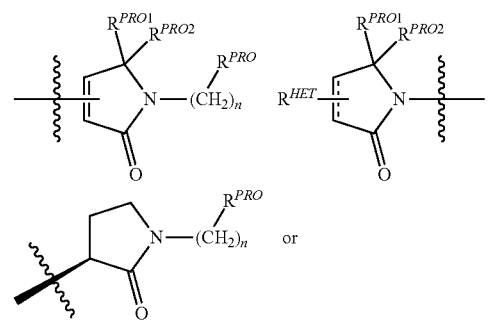

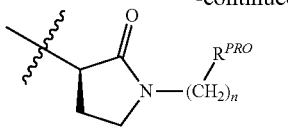

group,
wherein:
R$^{PRO}$ is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

R$^{PRO1}$ and R$^{PRO2}$ are each independently H, an optionally subsituted C$_1$-C$_3$ alkyl group or together form a keto group, and each n is 0, 1, 2, 3, 4, 5, or 6 (preferably 0 or 1), wherein each of said Heterocycle groups may be optionally substituted with a linker group to which is attached a TBM group (including a ULM' group) or a pharmaceutically acceptable salt, stereoisomer, solvate or polymorph thereof.

In certain embodiments, W$^3$ substituents for use in the present invention also include specifically (and without limitation to the specific compound disclosed) the W$^3$ substituents which are found in the identified compounds disclosed herein (which includes the specific compounds which are disclosed in the present specification, and the figures which are attached hereto). Each of these W$^3$ substituents may be used in conjunction with any number of W$^4$ substituents, which are also disclosed herein.

In certain embodiments, Aryl groups for W$^4$ include optionally substituted phenyl or naphthyl groups, preferably phenyl groups, wherein the phenyl group is optionally substituted with a linker group to which is attached an TBMTBM group (including a ULM' group), a halogen (preferably F or Cl), an amine, monoalkyl- or dialkyl amine (preferably, dimethylamine), F, Cl, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is preferably substituted with a linker group attached to a TBM group, including a ULM' group), and/or at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldi-azole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

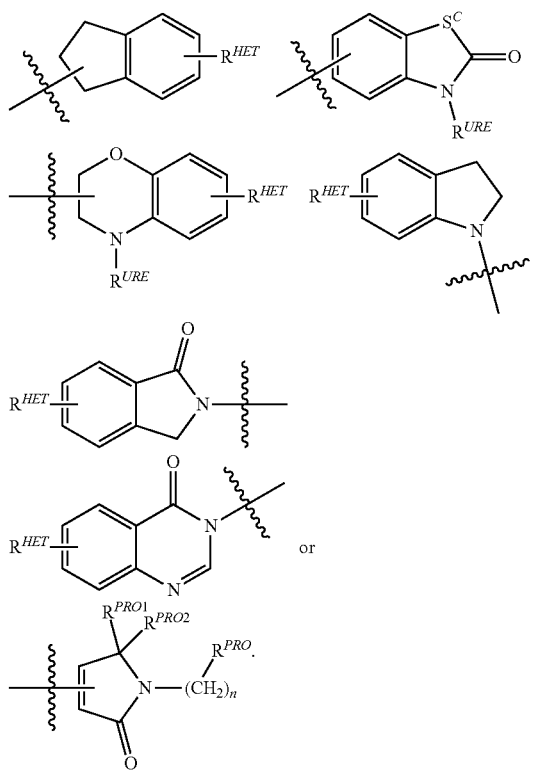

wherein:
S$^c$ is CHR$^{SS}$, NR$^{URE}$, or O;
R$^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);
R$^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);
R$^{URE}$ is H, a C$_1$-C$_6$ alkyl (preferably H or C$_1$-C$_3$ alkyl) or a —C(O)(C$_1$-C$_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally subsituted $C_1$-$C_3$ alkyl group or together form a keto group; and each n is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally substituted with a linker group to which is attached a TBM group (including a ULM' group).

In certain preferred aspects,

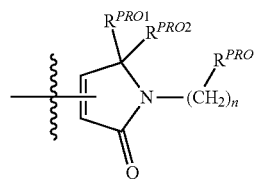

is a

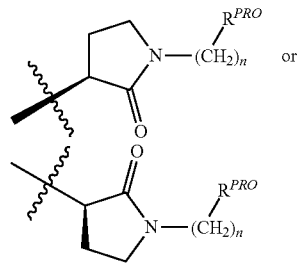

group,
where $R^{PRO}$ and n are the same as above.

In certain embodiments, heteroaryl groups for $W^4$ include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

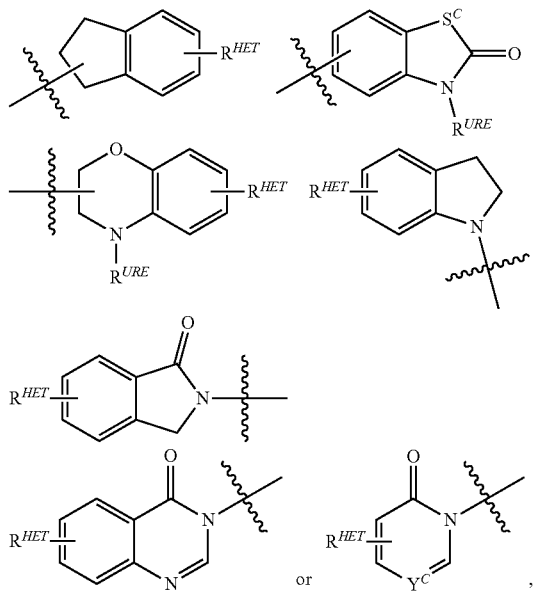

wherein:

$S^c$ is $CHR^{SS}$, $NR^{URE}$; or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O) ($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^c$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C— $R_a$ where $R_a$ is H or a $C_1$-$C_6$ alkyl group (preferably $C_1$-$C_3$ alkyl), each of which groups may be optionally substituted with a linker group to which is attached a TBM group (including a ULM' group).

In certain embodiments, heterocycle groups for $W^4$ include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

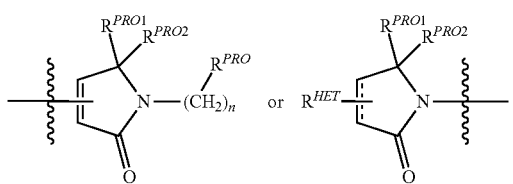 or 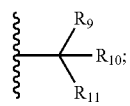

preferably, a

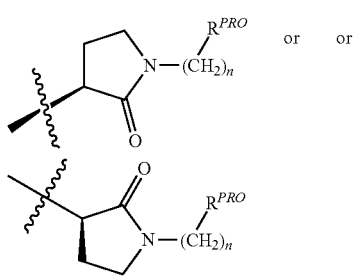 or or group,
wherein:
R$^{PRO}$ is H, optionally substituted C$_1$-C$_6$ alkyl or an optionally substituted aryl, heteroaryl or heterocyclic group;
R$^{PRO1}$ and R$^{PRO2}$ are each independently H, an optionally subsituted C$_1$-C$_3$ alkyl group or together form a keto group and
each n is independently 0, 1, 2, 3, 4, 5, or 6 (often 0 or 1), each of which groups may be optionally substituted with a linker group to which is attached a TBM group (including a ULM' group) In additional embodiments, W$^4$ substituents for use in the present invention also include specifically (and without limitation to the specific compound disclosed) the W$^4$ substituents which are found in the identified compounds disclosed herein (which includes the specific compounds which are disclosed in the present specification, and the figures which are attached hereto). Each of these W$^4$ substituents may be used in conjunction with any number of W$^3$ substituents which are also disclosed herein.

In certain additional embodiments, ULM-a, is optionally substituted by 1-3 R$^P$ groups in the pyrrolidine moiety. Each R$^P$ is independently H, halo, —OH, C$_{1-3}$alkyl.

In any of the embodiments described herein, the W$^3$, W$^4$ can independently be covalently coupled to a linker which is attached one or more TBM groups.

In certain embodiments, ULM is a group (derivatized or configured to be linked or coupled to an TBM via a linker (as indicated by the dashed line) according to the chemical structure:

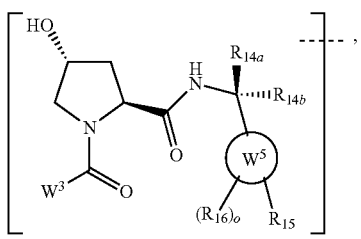

wherein:
W$^3$ is optionally substituted aryl, optionally substituted heteroaryl, or

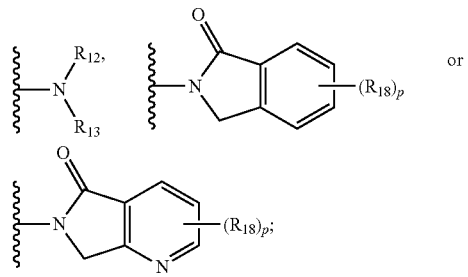

each R$_9$ and R$_{10}$ is independently hydrogen, optionally substituted alkyl, optionally substituted cycloalkyl, optionally substituted hydroxyalkyl, optionally substituted heteroaryl, or haloalkyl; or R$_9$, R$_{10}$, and the carbon atom to which they are attached form an optionally substituted cycloalkyl;
R$_{11}$ is optionally substituted heterocyclic, optionally substituted alkoxy, optionally substituted heteroaryl, optionally substituted aryl, R$_{12}$ is H or optionally substituted alkyl;
R$_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;
R$_{14a}$, R$_{14b}$, is each independently H, haloalkyl, or optionally substituted alkyl;
W$^5$ is a phenyl or a 5-10 membered heteroaryl,
R$_{15}$ is H, halogen, CN, OH, NO$_2$, NR$_{14a}$R$_{14b}$, OR$_{14a}$, CONR$_{14a}$R$_{14b}$, NR$_{14a}$COR$_{14b}$, SO$_2$NR$_{14a}$R$_{14b}$, NR$_{14a}$SO$_2$R$_{14b}$, optionally substituted alkyl, optionally substituted haloalkyl, optionally substituted haloalkoxy; aryl, heteroaryl, cycloalkyl, cycloheteroalkyl;
each R$_{16}$ is independently halo, optionally substituted alkyl, optionally substituted haloalkyl, hydroxy, or optionally substituted haloalkoxy;
o is 0, 1, 2, 3, or 4;
each R$_{18}$ is independently halo, optionally substituted alkoxy, cyano, optionally substituted alkyl, haloalkyl, haloalkoxy or a linker; and
p is 0, 1, 2, 3, or 4.
In certain embodiments, R$_{15}$ is

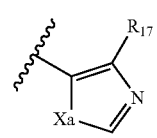

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In certain embodiments, $R_{17}$ is selected from the group methyl, ethyl, isopropyl, and cyclopropyl.

In certain additional embodiments, $R_{15}$ is selected from the group consisting of:

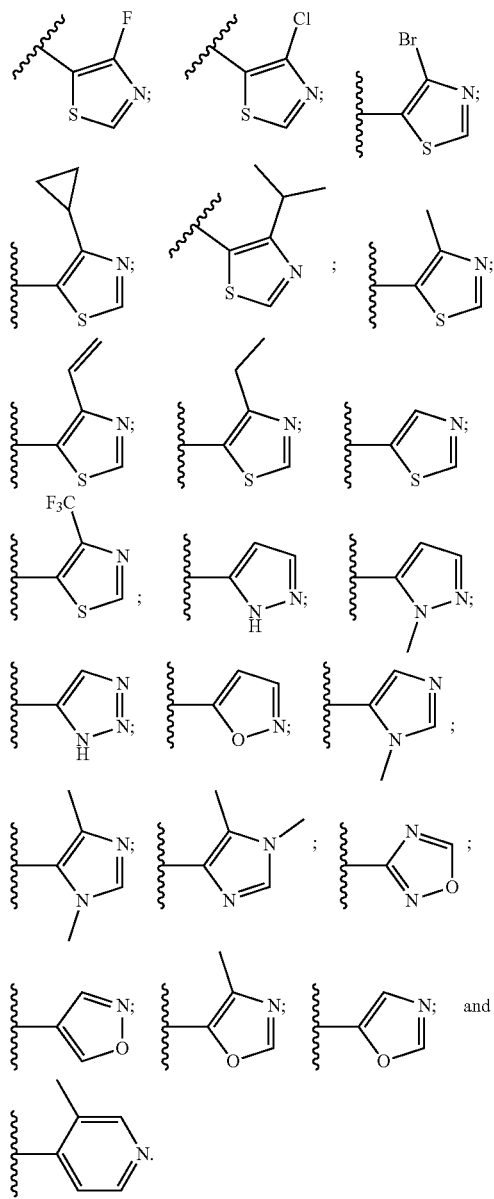

In certain embodiments, $R_{11}$ is selected from the group consisting of:

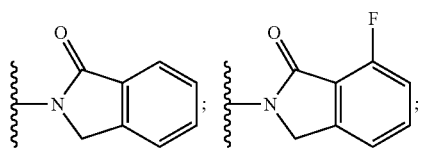

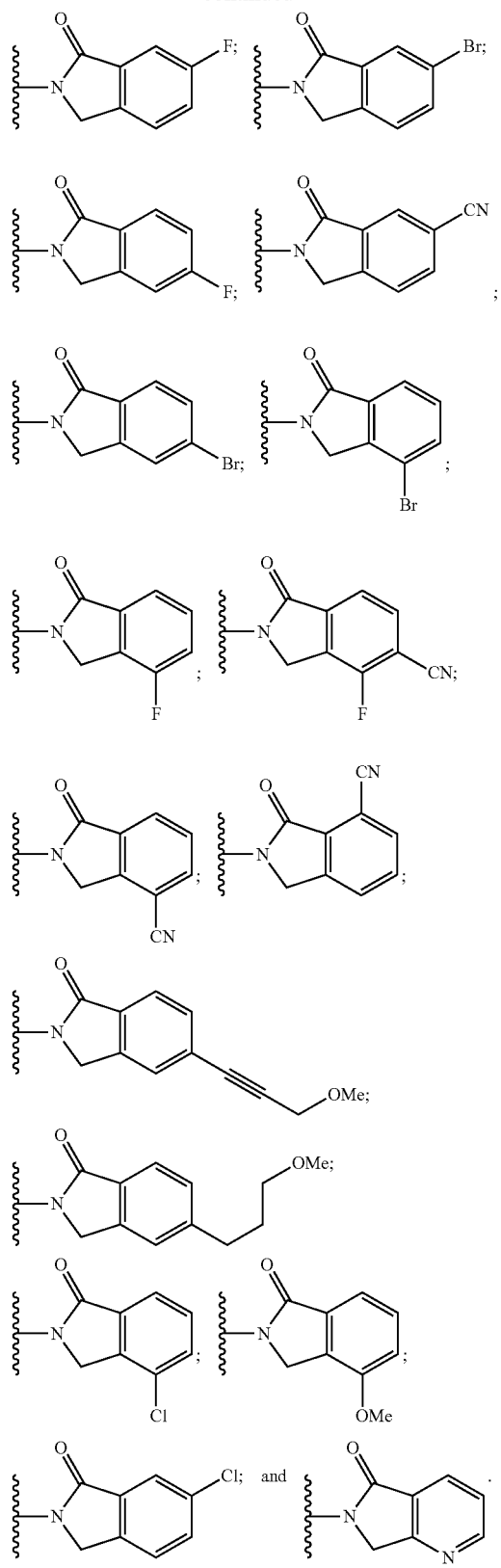

In certain embodiments, the ULM (derivatized or configured to be linked or coupled to an TBM via a linker (as indicated by the dashed line)) has the structure:

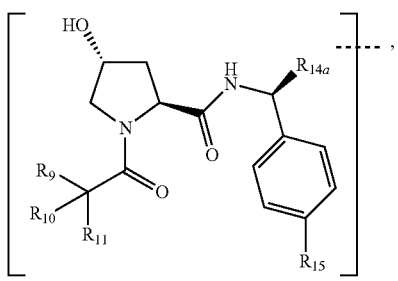

wherein:

$R_{14a}$ is independently H, haloalkyl, methyl, or optionally substituted alkyl;

$R_{15}$ is

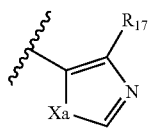

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalky $R_{17}$ is methyl, ethyl, isopropyl, or cyclopropyl;

$R_9$ is H;

$R_{10}$ is isopropyl, tert-butyl, sec-butyl, cyclopentyl, or cyclohexyl;

$R_{11}$ is

$R_{12}$ is H $R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; and In certain embodiments, the ULM or VLM is selected from the group consisting of:

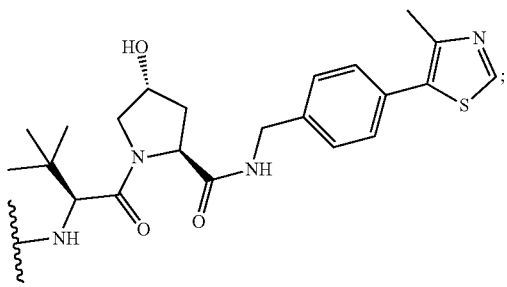

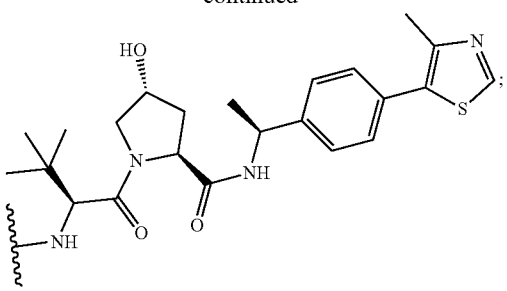

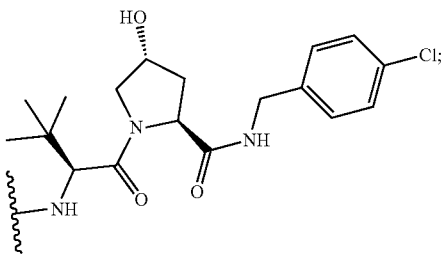

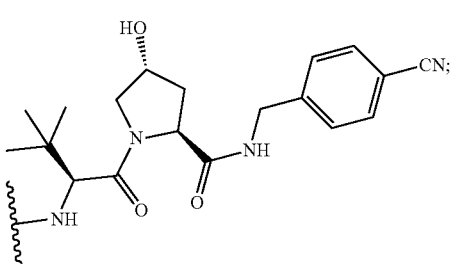

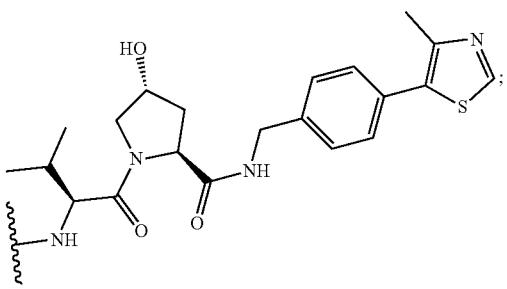

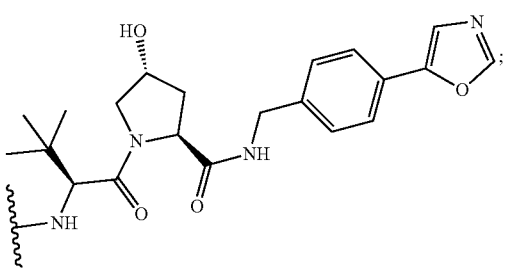

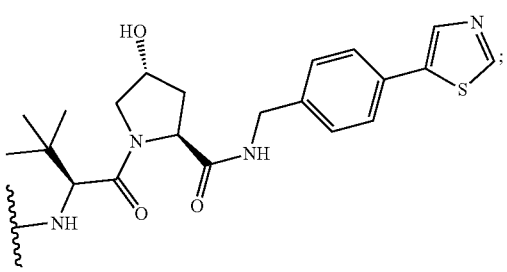

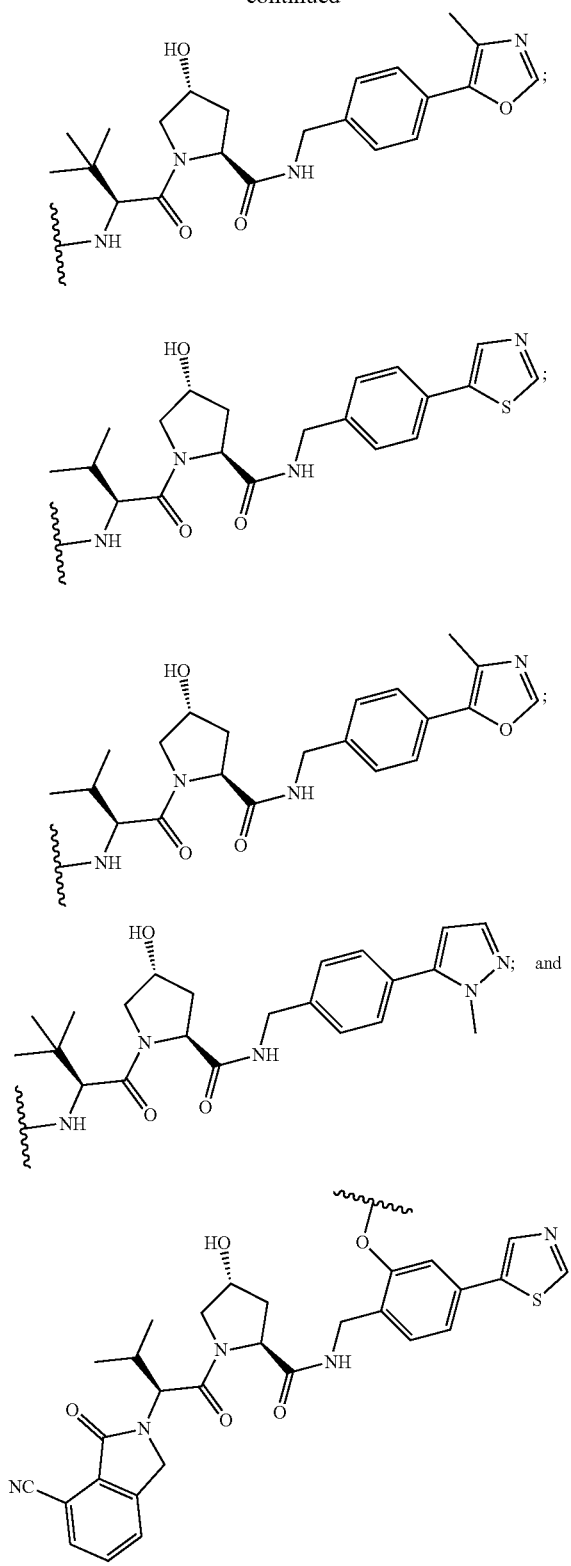

attached to the linker moiety at the position indicated.

In one aspect the description provides compounds useful for binding and/or inhibiting cereblon. In certain embodiments, the compound is selected from the group consisting of chemical structures:

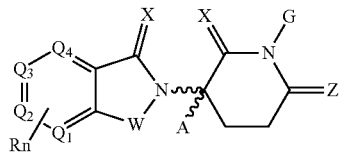
(a)

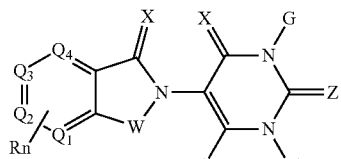
(b)

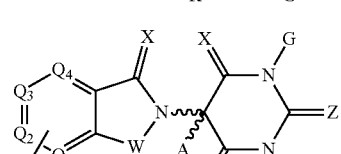
(c)

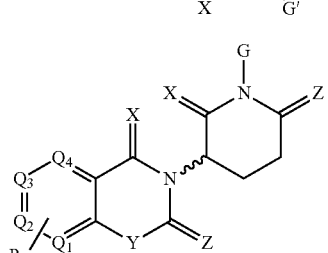
(d)

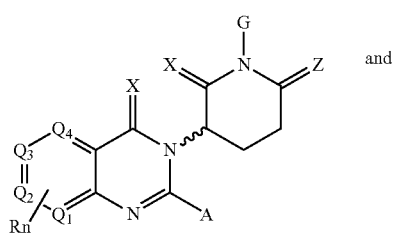
(e) and

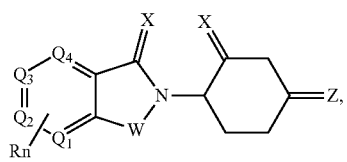
(f)

wherein:
W is independently selected from the group $CH_2$, CHR, C=O, $SO_2$, NH, and N-alkyl;
X is independently selected from the group O, S and $H_2$,
Y is independently selected from the group NH, N-alkyl, N-aryl, N-hetaryl, N-cycloalkyl, N-heterocyclyl, O, and S;
Z is independently selected from the group O, and S or $H_2$ except that both X and Z cannot be $H_2$,
G and G' are independently selected from the group H, alkyl, OH, $CH_2$-heterocyclyl optionally substituted with R', and benzyl optionally substituted with R';
Q1-Q4 represent a carbon C substituted with a group independently selected from R', N or N-oxide;
A is independently selected from the group alkyl, cycloalkyl, Cl and F;
R comprises, but is not limited to: —CONR'R", —OR', —NR'R",   —SR=,   —$SO_2$R',   —$SO_2$NR'R", —CR'R"—, —CR'NR'R"—, -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —CCR', —S(C=O)(C=N—R')R", —SF$_5$ and —OCF$_3$ R' and R" are independently selected from a bond, H, alkyl, cycloalkyl, aryl, hetaryl, heterocyclyl n is an integer from 1-4;

∿ represents a bond that may be stereospecific ((R) or (S)) or non-stereospecific; and R$_n$ comprises 1-4 independent functional groups or atoms.

In any of the compounds described herein, the CLM comprises a chemical structure selected from the group:

(a)
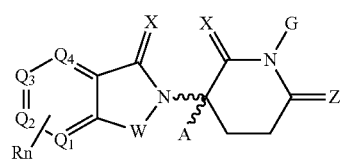

(b)
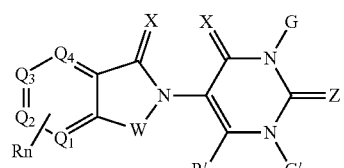

(c)
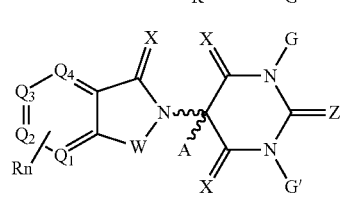

(d)
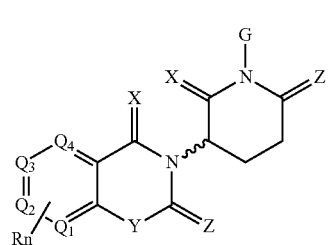

(e)
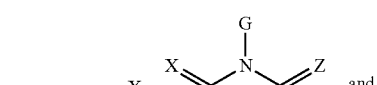
and
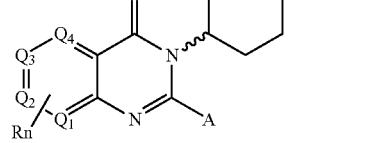

(f)
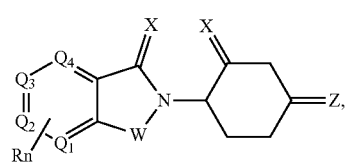

wherein:
W is independently selected from the group CH2, CHR, C=O, SO2, NH, and N-alkyl;
X is independently selected from the group O, S and H2;
Y is independently selected from the group NH, N-alkyl, N-aryl, N-hetaryl, N-cycloalkyl, N-heterocyclyl, O, and S;
Z is independently selected from the group O, and S or H2 except that both X and Z cannot be H2;
G and G' are independently selected from the group H, alkyl, OH, CH2-heterocyclyl optionally substituted with R', and benzyl optionally substituted with R';
Q1-Q4 represent a carbon C substituted with a group independently selected from R', N or N-oxide;
A is independently selected from the group alkyl, cycloalkyl, Cl and F;
R comprises, but is not limited to: —CONR'R", —OR', —NR'R", —SR', —SO2R', —SO2NR'R", —CR'R"—, —CR'NR'R"—, -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —CF3, —CN, —NR'SO2NR'R", —NR'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —CO2R', —C(C=N—OR')R", —CR'=CR'R", —CCR', —S(C=O)(C=N—R')R", —SF5 and —OCF3

R' and R" are independently selected from a bond, H, alkyl, cycloalkyl, aryl, hetaryl, heterocyclyl n is an integer from 1-4;

∿ represents a bond that may be stereospecific ((R) or (S)) or non-stereospecific; and Rn comprises 1-4 independent functional groups or atoms, and optionally, one of which is modified to be covalently joined to a PTM, a chemical linker group (L), a ULM, CLM (or CLM') or combination thereof.

Exemplary Linkers

In certain embodiments, the compounds as described herein include one or more TBM chemically linked or coupled to one or more ULMs or VLMs via a chemical linker (L). In certain embodiments, the linker group L is a group comprises one or more covalently connected structural units of A (e.g. -A$_1$ ... A$_q$-), wherein A$_1$ is coupled to an TBM moiety, and q is an integer greater than or equal to 0. In certain embodiments, q is an integer greater than or equal to 1.

In certain embodiments, e. g., where q is greater than 2, A$_q$ is a group which is connected to a ULM or VLM moiety, and A$_1$ and A$_q$ are connected via structural units of A (number of such structural units of A: q-2).

In certain embodiments, e. g., where q is 2, A$_q$ is a group which is connected to A$_1$ and to a ULM or VLM moiety.

In certain embodiments, e. g., where q is 1, the structure of the linker group L is -A$_1$-, and A$_1$ is a group which is connected to a ULM or VLM moiety and an TBM moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, A$_1$ to A$_q$ are, each independently, a bond, CR$^{L1}$R$^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L3}$C(=NCN), NR$^{L3}$C(=CNO$_2$)NR$^{L4}$, C$_{3-11}$cycloalkyl optionally substituted with 0-6 R$^{L1}$ and/or R$^{L2}$ groups, C$_{3-11}$heteocyclyl optionally substituted with 0-6 R$^{L1}$ and/or R$^{L2}$ groups, aryl optionally substituted with 0-6 R$^{L1}$ and/or R$^{L2}$ groups, heteroaryl optionally substituted with 0-6 $R^{L1}$ and/or $R^{L2}$ groups, wherein $R^{L1}$ or $R^L{}_2$, each independently, can be linked to other A groups to form cycloalkyl and/or heterocyclyl moeity which can be further substituted with 0-4 $R^{L5}$ groups;

wherein $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)$(C_{1-8}$alkyl), OH, $NH_2$, SH, $SO_2C_{1-8}$alkyl, $P(O)(OC_{1-8}$alkyl)$(C_{1-8}$alkyl), $P(O)(OC_{1-8}$alkyl$)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl)$CONH(C_{1-8}$alkyl), $N(C_{1-8}$alkyl)$CON(C_{1-8}$alkyl$)_2$, $NHCONH(C_{1-8}$alkyl), $NHCON(C_{1-8}$alkyl$)_2$, $NHCONH_2$, $N(C_{1-8}$alkyl)$SO_2NH(C_{1-8}$alkyl), $N(C_{1-8}$alkyl)$SO_2N(C_{1-8}$alkyl$)_2$, $NHSO_2NH(C_{1-8}$alkyl), $NHSO_2N(C_{1-8}$alkyl$)_2$, $NHSO_2NH_2$.

In certain embodiments, the linker (L) is selected from the group consisting of):

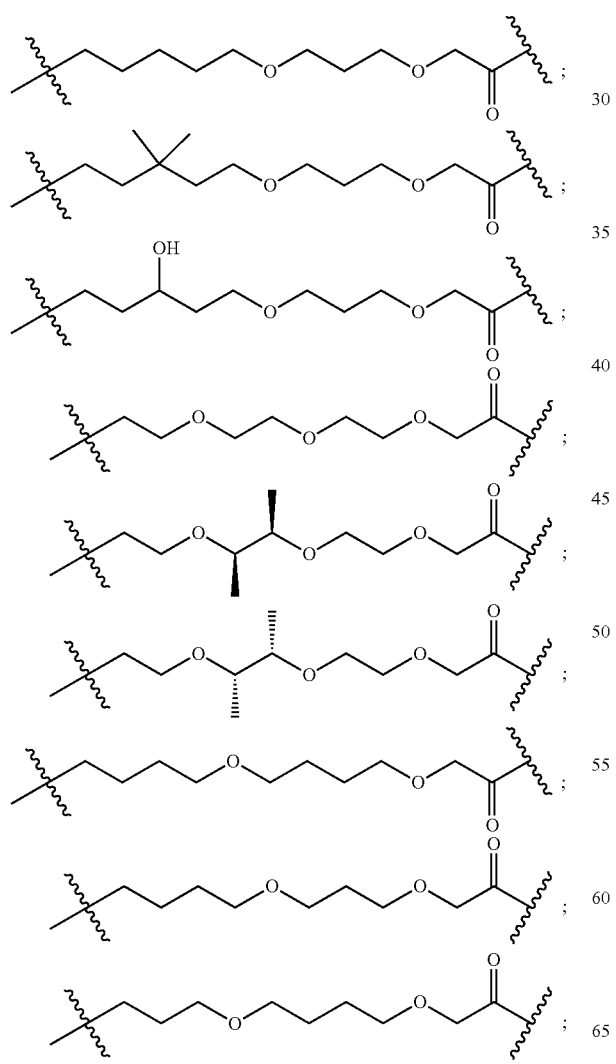

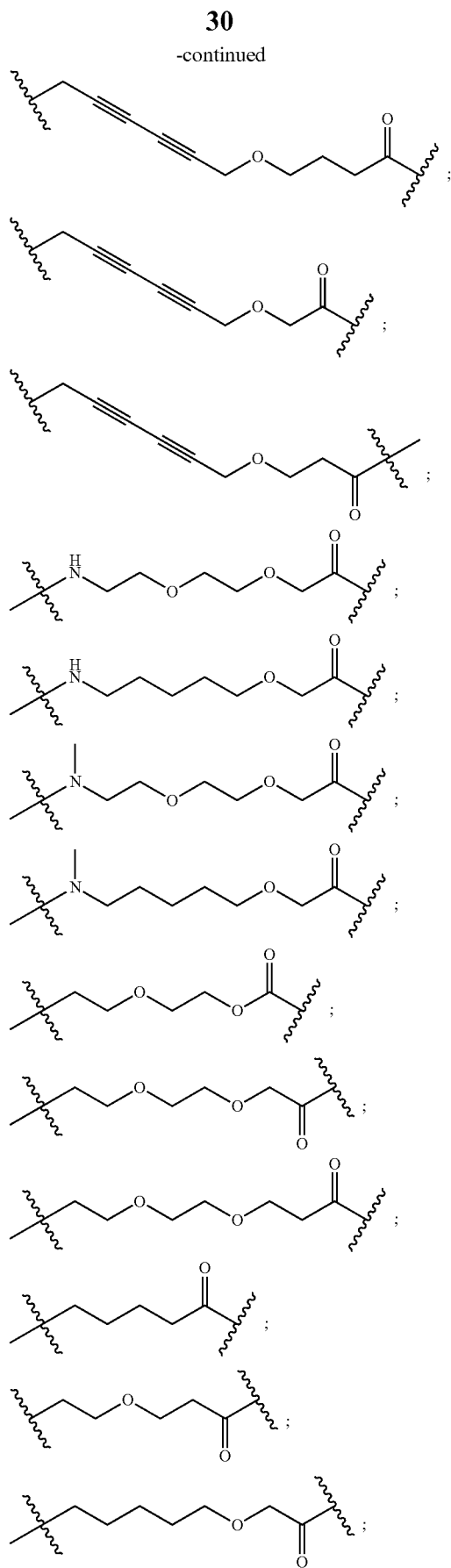

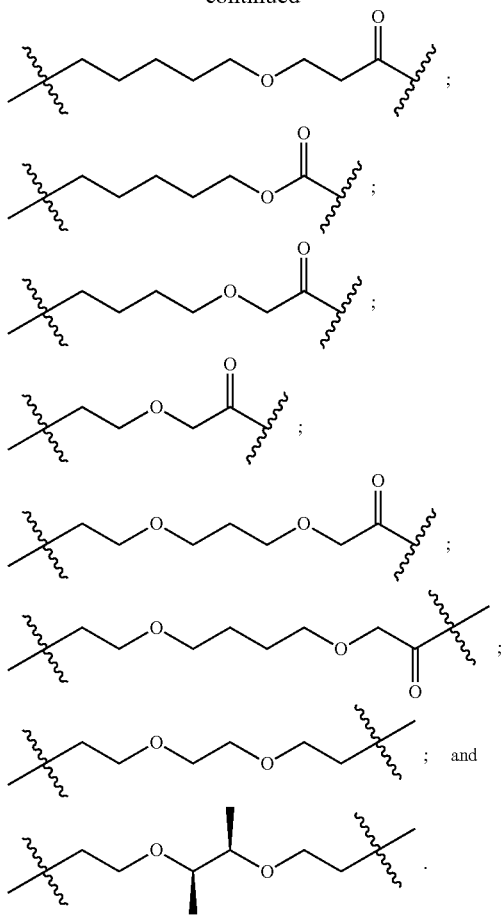

; and

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In another embodiment, the present invention provides a library of compounds. The library comprises more than one compound wherein each compound has a formula of TBM-L-ULM, wherein ULM is a ubiquitin pathway protein binding moiety (preferably, an E3 ubiquitin ligase moiety as otherwise disclosed herein), e.g., a VLM, and TBM is an TBK1 protein binding moiety, wherein TBM is coupled (preferably, through a linker moiety) to ULM, and wherein the ubiquitin pathway protein binding moiety recognizes an ubiquitin pathway protein, in particular, an E3 ubiquitin ligase.

The present description includes, where applicable, the compositions comprising the pharmaceutically acceptable salts, in particular, acid or base addition salts of compounds of the present invention.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention.

The acids which are used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

Compositions

In another aspect, the description provides compositions comprising compounds as described herein, including salts thereof, and a pharmaceutically acceptable carrier. In certain embodiments, the compositions are therapeutic or pharmaceutical compositions comprising an effective amount of a compound as described herein and a pharmaceutally acceptable carrier.

The amount of compound in a pharmaceutical composition of the instant invention that may be combined with the carrier materials to produce a single dosage form will vary depending upon the host and disease treated, the particular mode of administration. Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Modes of Administration

In any of the aspects or embodiments described herein, the therapeutic compositions comprising compounds described herein can be in any suitable dosage form configured to be delivered by any suitable route. For example, the compounds can be administered by any appropriate route, for example, orally, parenterally, intravenously, intradermally, subcutaneously, or topically, including transdermally, in liquid, cream, gel, or solid form, rectally, nasally, buccally, vaginally or via an implanted reservoir or by aerosol form.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The compounds as described herein may be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient.

Administration of compounds as sprays, mists, or aerosols for intra-nasal, intra-tracheal or pulmonary administration may also be used. Compounds as described herein may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Hely or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials are included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds as described herein can be treated by administering to the patient (subject) an effective amount of the compound including pharmaceutically acceptable salts, solvates or polymorphs, thereof optionally in a pharmaceutically acceptable carrier or diluent, either alone, or in combination with other known agents.

Co-Administration

Disease states of conditions which may be treated using compounds or compositions according to the present description include, but not limited to, for example, cancer (e.g., prostate cancer), and Kennedy's disease. In certain embodiments, the therapeutic or pharmaceutical compositions comprise an effective amount of an additional biologically or bioactive active agent, e.g., an agent effective for the treatment of cancer, that is co-administered.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. In certain preferred aspects of the present invention, one or more of the present compounds described above, are coadministered in combination with at least one additional bioactive agent, especially including an anticancer agent. In particularly preferred aspects of the invention, the co-administration of compounds results in synergistic therapeutic, including anticancer therapy.

In another aspect, the description provides a composition comprising an effective amount of two or more of the PROTAC compounds as described herein, and a pharmaceutically acceptable carrier. In certain embodiments, the composition further comprises an effective or synergistic amount of another bioactive agent that is not a PROTAC compound.

Pharmaceutical compositions comprising combinations of an effective amount of at least one bifunctional compound according to the present invention, and one or more of the compounds otherwise described herein, all in effective amounts, in combination with a pharmaceutically effective amount of a carrier, additive or excipient, represents a further aspect of the present invention.

The term "bioactive agent" is used to describe an agent, other than the PROTAC compounds described herein, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents.

The term "additional anti-cancer agent" is used to describe an anti-cancer agent, which may be combined with PROTAC compounds according to the present description to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, an androgen receptor inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t)6, Azgly 10] (pyro-Glu-His-Trp-Ser-Tyr-D-Ser(Bu t)-Leu-Arg-Pro-Azgly-NH$_2$ acetate [$C_{59}H_{84}N_{18}O_{14}$—($C_2H_4O_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

Methods of Treatment

In another aspect, the disclosure provides methods of modulating protein ubiquitination and degradation in a subject, e.g., a cell, a tissue, mammal, or human patient, the method comprising administering an effective amount of a compound as described herein or a composition comprising an effective amount of the same to a subject, wherein the compound or composition comprising the same is effective in modulating protein ubquitination and degration of the protiein in the subject. In certain embodiments, the protein is TBK1.

In certain embodiments, the description provides a method for regulating protein activity of TBK1 in a patient in need comprising administering to said patient an amount of a compound as described herein to a patient.

In still additional embodiments, the description provides a method of treating a disease state or condition in a patient wherein dysregulated protein activity is responsible for said disease state or condition, said method comprising administering to said patient an effective amount of a compound as described herein to said patient in order to regulate said protein activity in said patient. In certain embodiments, the protein is TBK1.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present invention are set forth hereinabove.

In another aspect, the disclosure provides methods of modulating AR protein ubiquitination and degradation in a subject, e.g., a cell, a tissue, mammal, or human patient, the method comprising administering an effective amount of a compound as described herein or a composition comprising an effective amount of the same to a subject, wherein the compound or composition comprising the same is effective in modulating AR protein ubquitination and degration of the protiein in the subject.

In another aspect, the disclosure provides methods of treating or ameliorating a symptom of a disease related to TBK1 activity in a subject, e.g., a cell, a tissue, mammal, or human patient, the method comprising administering an effective amount of a compound as described herein or a composition comprising an effective amount of the same to a subject in need thereof, wherein the compound or composition comprising the same is effective in treating or ameliorating a symptom of a disease related to TBK1 activity in the subject.

In certain embodiments, the disease or disorder is asthma, multiple sclerosis, cancer, prostate cancer, Kenney's disease, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome. In an embodiment, said cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas. In certain embodiments, the disease to be treated is cancer, e.g., prostate cancer, or Kennedy's Disease. In a preferred embodiment, the subject is a human.

In another aspect, the disclosure provides methods of treating or ameliorating a symptom of a disease related to TBK1 activity in a subject, e.g., a cell, a tissue, mammal, or human patient, the method comprising administering an effective amount of a compound as described herein or a composition comprising an effective amount of the same and an effective or synergistic amount of another bioactive agent to a subject in need thereof, wherein the composition comprising the same is effective in treating or ameliorating a symptom of a disease related to TBK1 activity in the subject. In certain embodiments, the disease to be treated is cancer, e.g., prostate cancer, or Kennedy's Disease. In a preferred embodiment, the subject is a human. In certain additional embodiments, the additional bioactive agent is an anti-cancer agent.

In alternative aspects, the present invention relates to a method for treating a disease state by degrading a protein or polypeptide through which a disease state or condition is modulated comprising administering to said patient or subject an effective amount of at least one compound as described hereinabove, optionally in combination with an additional bioactive agent. The method according to the present invention may be used to treat a large number of disease states or conditions including cancer, by virtue of the administration of effective amounts of at least one compound described herein.

In another aspect, the disclosure provides methods for identifying the effects of the degradation of proteins of interest in a biological system using compounds according to the present invention.

Kits

In another aspect, the description provides kits comprising compounds or compositions as described herein. The kit may be promoted, distributed, or sold as a unit for performing the methods of the present invention. In addition, the kits of the present invention may preferably contain instructions which describe a suitable use. Such kits can be conveniently used, e.g., in clinical settings, to treat patients exhibiting symptoms of, e.g., cancer or Kennedy's Disease.

Exemplary TBK1 Binding Moieties (TBMs)

TANK-binding kinase 1 (TBK1) is a serine/threonine kinase and a noncanonical member of the IKK family implicated in antiviral immune response as well as tumor genesis and development and is therefore a target that has attracted considerable attention with regards to the identification of agents that could diminish its activity. Of particular note are the various reports regarding the criticality of TBK1 signaling in KRAS mutant tumors, determined using RNAi.

We embarked on a campaign to assess whether TBK1 was degradable by our technology and if so, whether they replicated the KRAS synthetic lethality reported with TBK1 RNAi.

Figure 2:
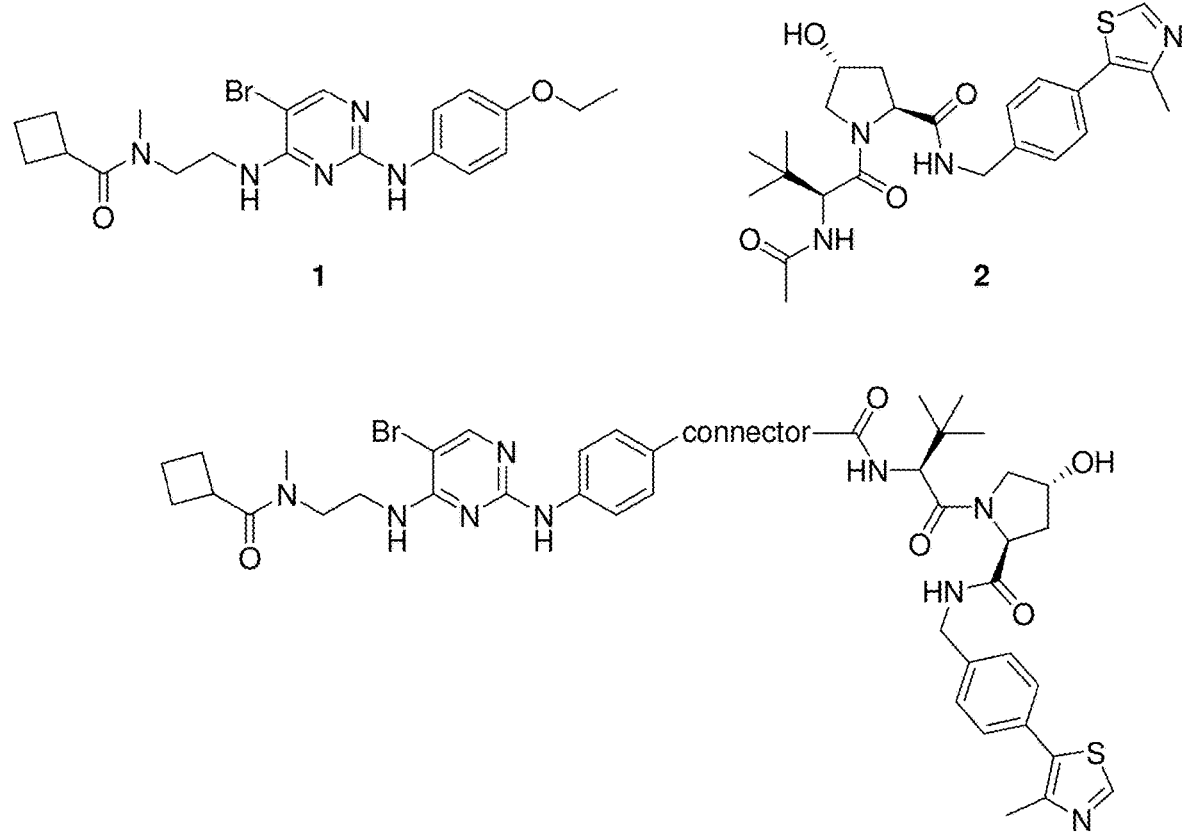
FIG. 2. TBK1 ligand 1 and VHL ligand 2 components selected for inclusion into the TBK1 PROTAC architecture.

For the design of the TBK1 PROTACs we selected the classic kinase aminopyridine chemotype 1 as the ligand for TBK1 ($K_d$ 1.3 nM), and our 4-hydroxyproline derivative 2 as the recruitment ligand for the Von Hippel-Landau (VHL) E3 ligase ($IC_{50}$ 500 nM FP assay) (FIG. 2).

Figure 3:
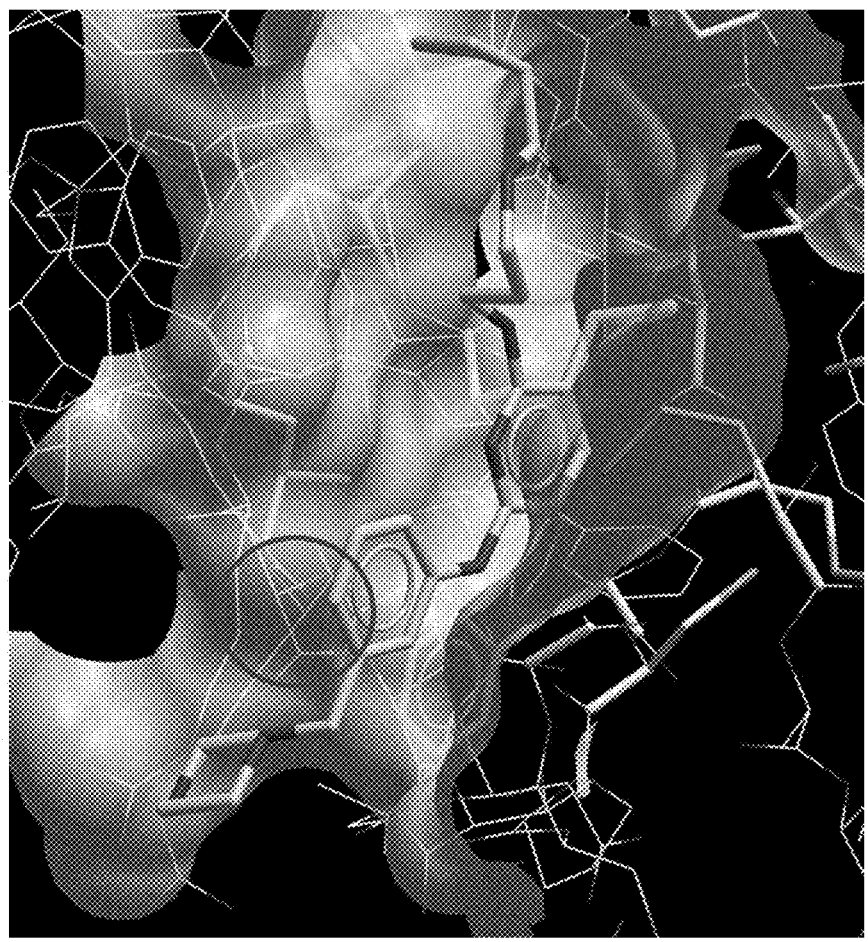
FIG. 3. Snapshot of an aminopyrimidine TBK1 ligand bound to TBK1 (from 4IM0)
Figure 4:
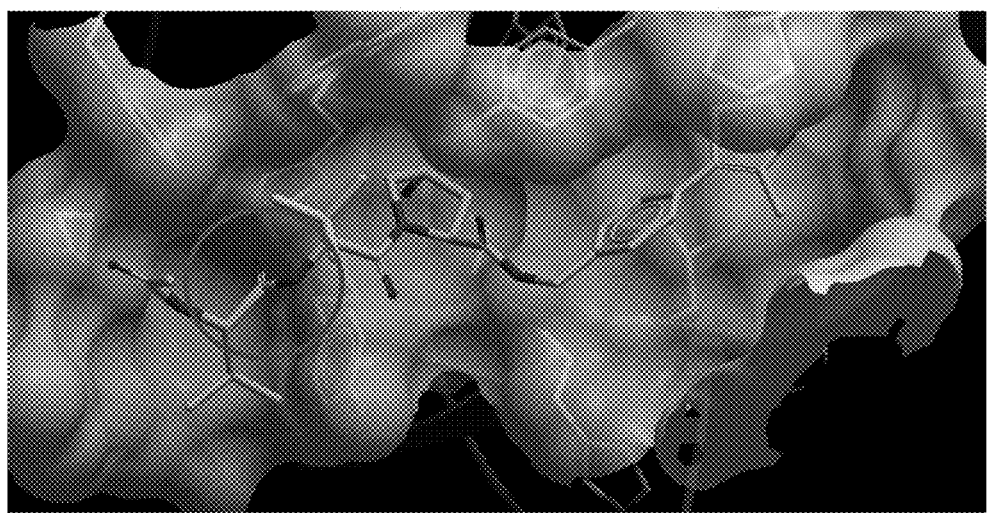
FIG. 4. Snapshot of hydroxyproline VHL ligand chemotype bound to VHL (from 4W9L)

The PROTAC molecule architecture requires that these ligands be separated by a connector component (FIG. 2). FIGS. 3 and 4 show snapshots of the crystal structures of the general VHL and TBK1 ligand chemotypes (PDB codes: 4W9L and 4IM0) and suggest points on these ligands where such a connector could be attached that would allow ready egress from the protein in question without obvious detrimental effects on ligand binding. For the TBK1 ligand we selected the para-position of the pyrimidine 2-aminophenyl moiety; for the VHL ligand we selected the acetamide moiety as the tethering position.

Not knowing a priori what distance the TBK1 and VHL ligands would have to be positioned in the PROTAC to effectively associate their respective proteins, we undertook a systematic survey of connector length using flexible and therefore accommodating alkyl ether chemistries (Table 1).

TABLE 1

Effect of connector length on degradation activity

| Cmpd | Connector | # Connector atoms | $DC_{50}$ (nM) | $D_{max}$ × (%) | PSA (Å2) |
|---|---|---|---|---|---|
| 1 | NA | — | >1000 | ND | 79 |
| 2 | NA | — | NA | NA | 112 |
| 3 | [structure] | 7 | >1000 | ND | 200 |
| 4 | [structure] | 8 | >1000 | ND | 209 |
| 5 | [structure] | 9 | >1000 | ND | 200 |
| 6 | [structure] | 10 | >1000 | ND | 209 |
| 7 | [structure] | 11 | >1000 | ND | 219 |
| 8 | [structure] | 12 | 88 | 79 | 209 |
| 9 | [structure] | 13 | 71 | 86 | 219 |

TABLE 1-continued

Effect of connector length on degradation activity

| Cmpd | Connector | # Connector atoms | $DC_{50}$ (nM) | $D_{max}$ (%) | PSA (Å2) |
|---|---|---|---|---|---|
| 10 | | 14 | 103 | 92 | 228 |
| 11 | | 15 | 32 | 96 | 219 |
| 12 | | 16 | 95 | 90 | 209 |
| 13 | | 17 | 29 | 96 | 237 |
| 14 | | 18 | 6 | 96 | 228 |
| 15 | | 19 | 25 | 96 | 228 |
| 16 | | 20 | 34 | 96 | 246 |
| 17 | | 21 | 3 | 96 | 237 |

NA: not applicable.
ND: not determined.
$DC_{50}$: concentration at which 50% degradation is observed.
$D_{max}$: maximal degradation observed.
Data represent the mean of ≥ 2 determinations.

From this initial library, potent, sub-micromolar TBK1-VHL PROTAC degraders were identified (PROTACs 8-17). The gross SAR clearly indicates a dependence on a minimum connector length with connectors of <12 atoms (ca. 13Å in fully extended form) demonstrating no appreciable degradation activity. Longer connectors appear generally well tolerated despite their higher PSA and possible cell penetrance burden, and the SAR, to the extent it was explored, indicates no obvious maximum tolerated length. These observations are consistent with the concept that the bifunctional PROTAC species mediates the association of the TBK1 and VHL proteins to form a ternary complex, but that a minimum PROTAC length is required to allow the proteins to come together without incurring steric conflicts. It was hypothesized that the very flexible nature of the connector chemistry allows the longer connectors to orient themselves as necessary to allow the two proteins to associate and for ubiquitin to transfer to TBK1. The extent to which the flexibility of each individual connector allows it to organize spatially in order to properly orient the VHL-TBK1 interaction likely governs the efficiency of such transfer and therefore contributes to the subtle degradation SAR seen across PROTACs 8-17, along with differences in cell permeation.

Figure 5:
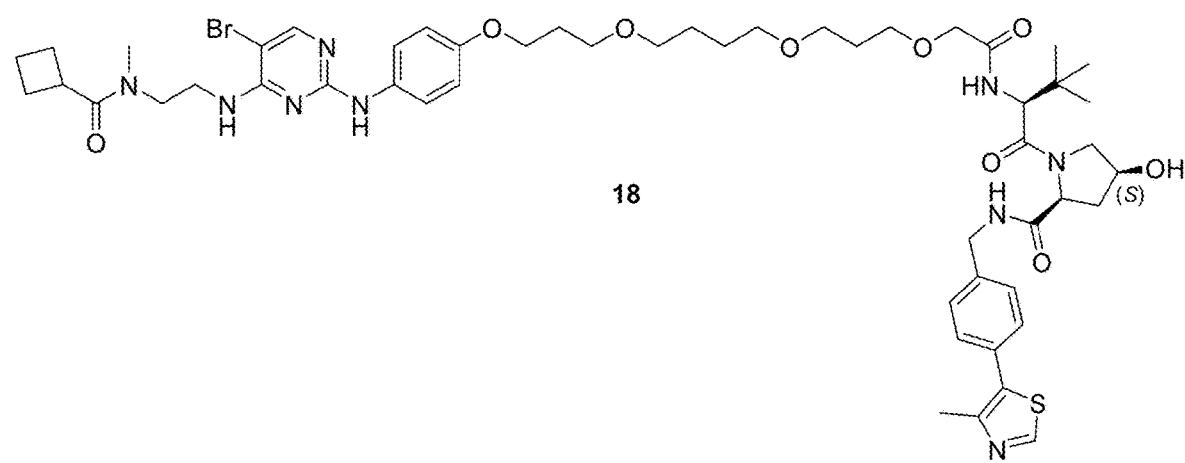
FIG. 5. PROTAC 18 is a VHL incompetent epimer of active TBK1 degrader 11.

To confirm the mechanistic dependence on VHL for TBK1 degradation, we prepared PROTAC 18, an epimer of active PROTAC 11, which by nature of the reversed (S) stereochemistry at the proline 4-position, has no appreciable binding to VHL (FP IC$_{50}$>5 uM) but is identical in all other respects (FIG. 5).

Figure 6:
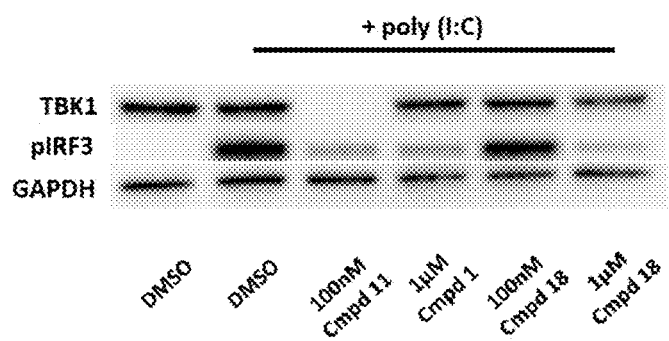
FIG. 6. PROTAC 11 but not its VHL-incompetent epimer 18 nor TBK1 inhibitor 1 effects degradation of TBK1. All 3 display competent intracellular TBK1/pIRF3 activity.

PROTAC 18 showed no significant degradation of TBK1 (FIG. 6), confirming VHL's role in the degradation of TBK1 by PROTAC 11. It was confirmed that PROTAC 18 was not significantly compromised in terms of its TBK1 binding (Kd 5.9 nM), and also assessed the effect on 11 and 18 on the TBK1 downstream marker pIRF3. Both agents as well as the parent TBK1 ligand 1 displayed competent intracellular TBK1 binding as indicated by the inhibition of pIRF3.

Figure 7:
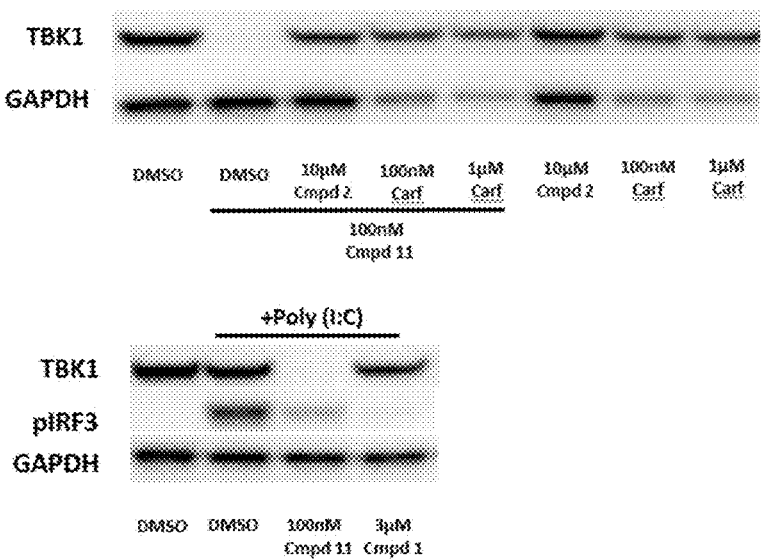
FIG. 7. PROTAC 11 mediated degradation of TBK1 is abrogated in the presence of the proteasome inhibitor carfilzomib.

The involvement of the proteasome in the VHL-mediated degradation of TBK1 by PROTAC 11 was assessed by addition of the proteasome inhibitor carfilzomib (Kyprolis®) to the assay conditions. Pre-treatment with carfilzomib markedly reduced the extent of TBK1 degradation by PROTAC 11 indicating that the 26S proteasome was indeed implicated in the degradation of TBK1 (FIG. 7). Also, the addition of excess VHL ligand 2 to the assay to compete with PROTAC 11 for VHL, also abrogated TBK1's degradation.

With mechanistically specific tool degrader 11 in hand, the impact of TBK1 binding on degradation potency and efficacy was evaluated. In order to minimize the impact of any cell permeation or conformational differences on observed degrader potency, only the 5-position of the pyrimidine TBK1 ligand component was modified and only using functionalities that did not substantially alter the 219 Å$^2$ polar surface area of the set (Table 2).

Maximal efficacy (>90% degradation) was achieved with PROTACs that had TBK1 affinities of ≤245 nM, beyond which degradation begins to drop off although remain significant (70%) even in the case of Compound 22 that has a Kd of 1 μM. That cellular degradation potency shown so high (65 nM) given that the affinities for the component ligands of PROTAC 28 to its TBK1 and VHL proteins be so modest (245 and 800 nM, respectively), is likely due to the ability of the PROTAC to initiate multiple cycles of degradation and drive a process and not an equilibrium mechanism such as traditional inhibition.

Next, the effect of changing the linker and VHL affinity was evaluated on degradation (Table 3 and Table 4). PROTACs 11 and 29-33 differ in the side chain chemistry of the glycine component of the VHL ligand which, as for the TBK1 ligand, do not grossly change the molecular properties of the PROTACs (PSA 219 Å$^2$) yet do alter their VHL affinity. Maximal efficacy was only seen with the parent PROTAC 11 (R=tBu) although, robust degradation (>70%) was seen with PROTAC 31 (R=Et).

TABLE 2

Effect of TBK1 affinity on degradation activity

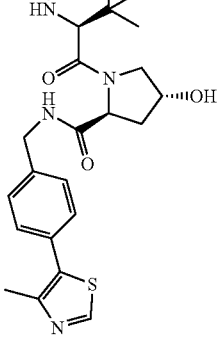

| Cmpd | R$_1$ | TBK1 K$_d$ (nM) | DC$_{50}$ (nM) | D$_{max}$ (%) |
|---|---|---|---|---|
| 19 | H | 725 ± 85 | >1000 | ND |
| 20 | Cl | 10.4 ± 0.6 | 10 | 96 |
| 21 | CF$_3$ | 13 | 29 | 96 |
| 22 | cBu | 1035 ± 165 | 544 | 70 |
| 23 | I | 4 ± 0.4 | 3 | 96 |
| 24 | F | 103.5 ± 6.5 | 282 | 74 |
| 25 | Me | 270 ± 40 | 92 | 89 |
| 26 | Et | 275 ± 35 | 121 | 77 |
| 27 | Vinyl | 130 ± 10 | 48 | 96 |
| 28 | cPr | 245 ± 25 | 65 | 96 |
| 11 | Br | 4.6 ± 1.1 | 12 | 96 |

ND: not determined.
DC$_{50}$: concentration at which 50% degradation is observed.
D$_{max}$: maximal degradation observed.
Data represent the mean of ≥ 2 determinations.

TABLE 3
Effect of VHL affinity on degradation activity
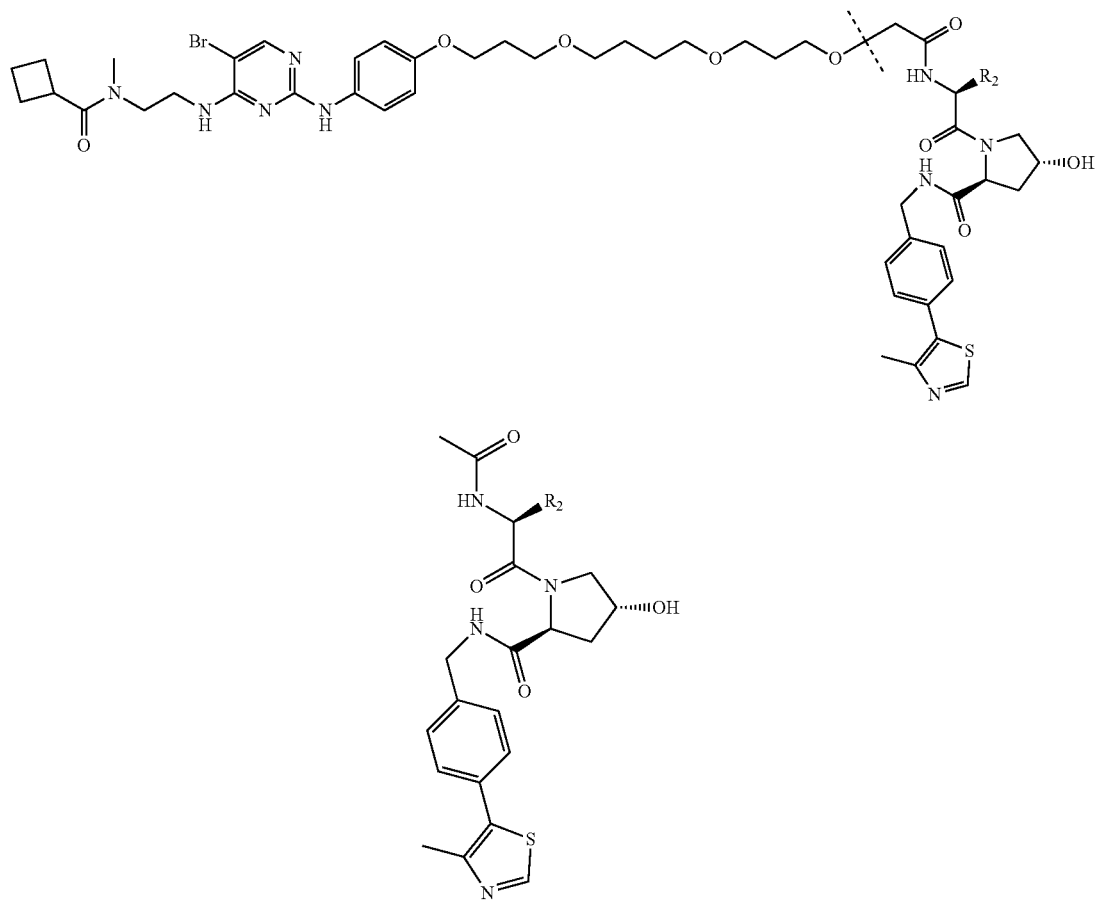
| Cmpd | $R_2$ | VHL Ligand $IC_{50}$ (µM) | $DC_{50}$ (nM) | $D_{max}$ (%) |
|---|---|---|---|---|
| 29 | H | 106 | >1000 | 0 |
| 30 | Me | 23.6 | >1000 | 34 |
| 31 | Et | 70.4 | 864 | 71 |
| 32 | $^n$Pr | 6.2 | 288 | 75 |
| 33 | $^i$Pr | 1.45 | 44 | 88 |
| 11 | $^t$Bu | 0.8 | 12 | 96 |

TABLE 4

Effect of linker and VHL structure on TBK1 degradation

| Compound # | Structure | % TBK1 remaining at 1 uM Cmpd** |
|---|---|---|
| 34 | 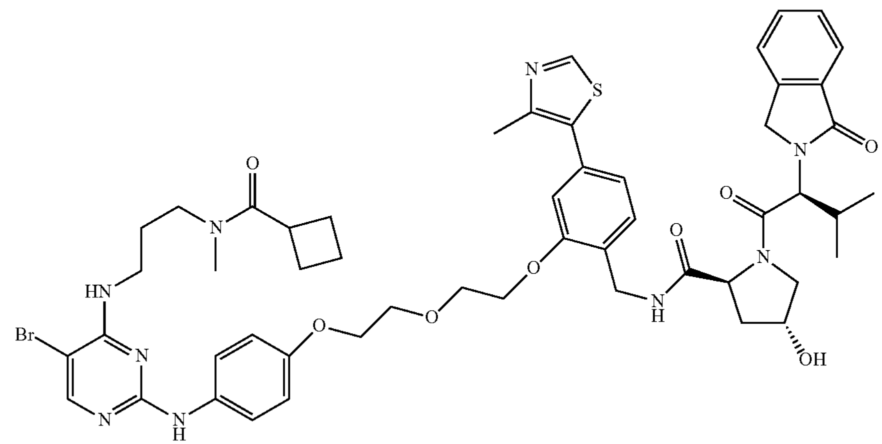 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOc2ccc(Nc3ncc(Br)c(NCCCN(C)C(=O)C4CCC4)n3)cc2)c1] | B |
| 35 | 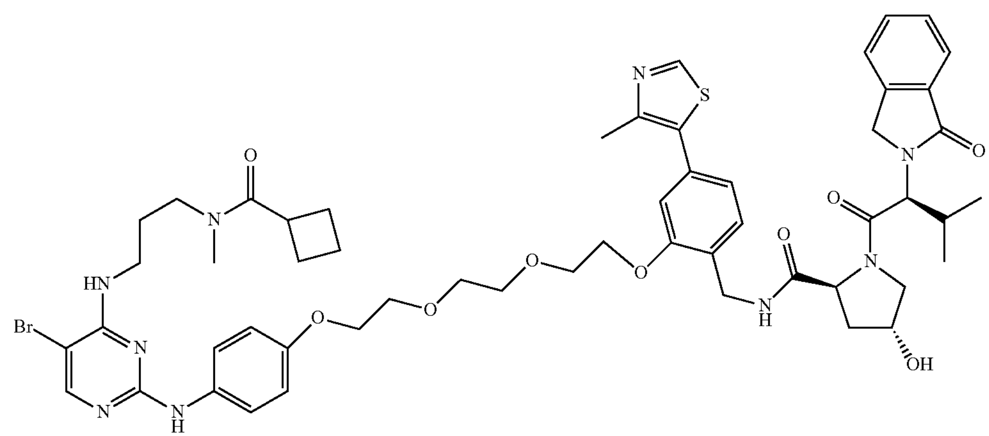 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOc2ccc(Nc3ncc(Br)c(NCCCN(C)C(=O)C4CCC4)n3)cc2)c1] | C |

TABLE 4-continued
Effect of linker and VHL structure on TBK1 degradation
| Compound # | Structure | % TBK1 remaining at 1 uM Crmpd** |
|---|---|---|
| 36 | 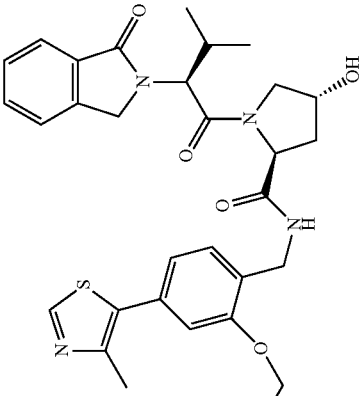 | C |
| 37 | 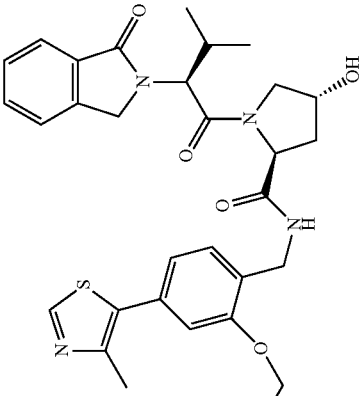 | C |

TABLE 4-continued
Effect of linker and VHL structure on TBK1 degradation
| Compound # | Structure | % TBK1 remaining at 1 uM Cmpd** |
|---|---|---|
| 38 | 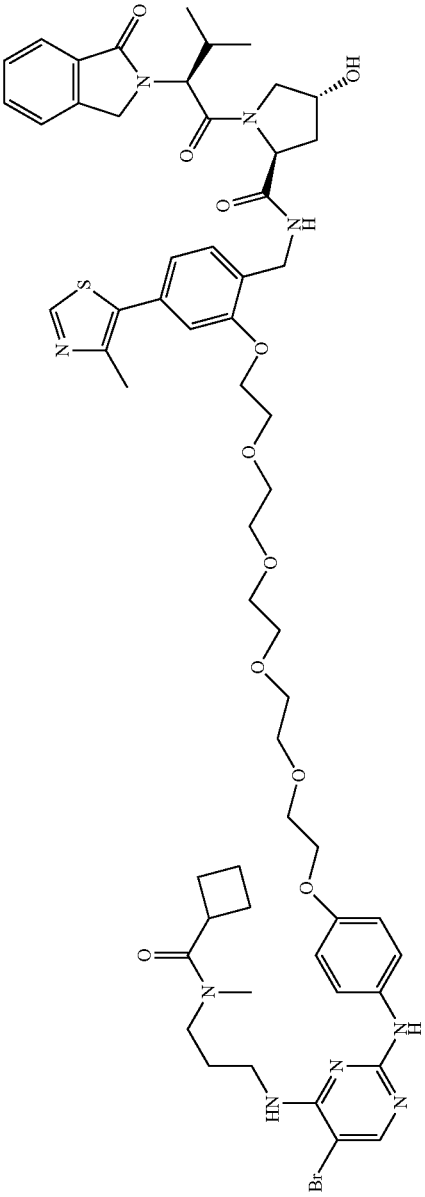 | C |
| 39 | 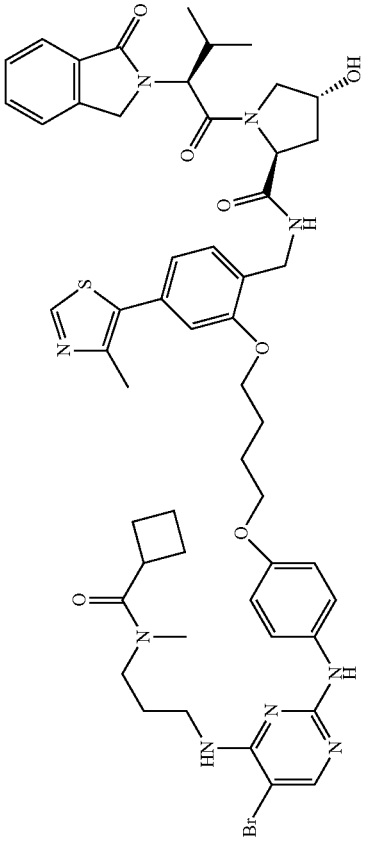 | C |

TABLE 4-continued

Effect of linker and VHL structure on TBK1 degradation

| Compound # | Structure | % TBK1 remaining at 1 uM Cmpd** |
|---|---|---|
| 40 | 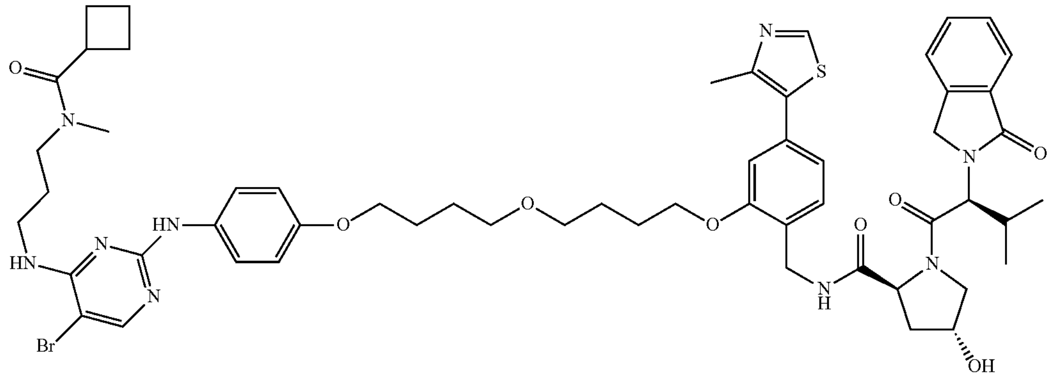 [SMILES: Cc1ncsc1-c1ccc(CNC(=O)[C@@H]2C[C@@H](O)CN2C(=O)[C@H](C(C)C)N2Cc3ccccc3C2=O)c(OCCCCOCCCCOc2ccc(Nc3ncc(Br)c(NCCCN(C)C(=O)C4CCC4)n3)cc2)c1] | C |
| 41 | 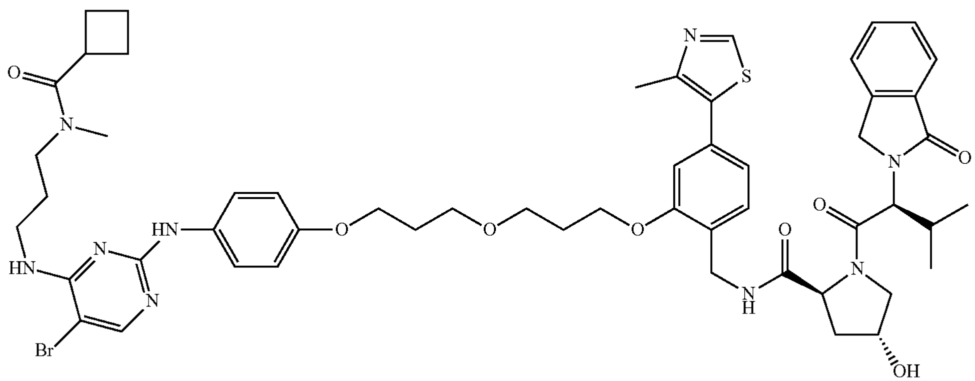 [SMILES: Cc1ncsc1-c1ccc(CNC(=O)[C@@H]2C[C@@H](O)CN2C(=O)[C@H](C(C)C)N2Cc3ccccc3C2=O)c(OCCCOCCCOc2ccc(Nc3ncc(Br)c(NCCCN(C)C(=O)C4CCC4)n3)cc2)c1] | C |

TABLE 4-continued
Effect of linker and VHL structure on TBK1 degradation
| Compound # | Structure | % TBK1 remaining at 1 uM Crmpd** |
|---|---|---|
| 42 | 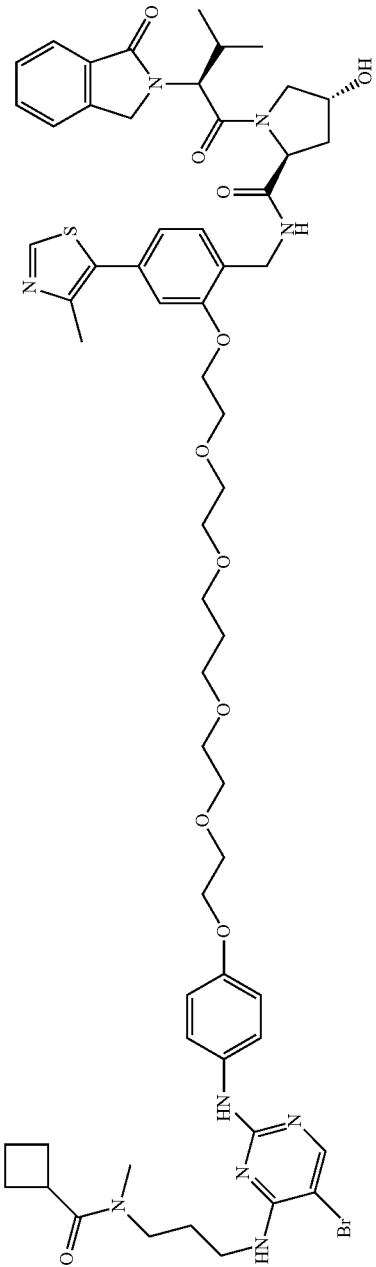 | B |
| 43 | 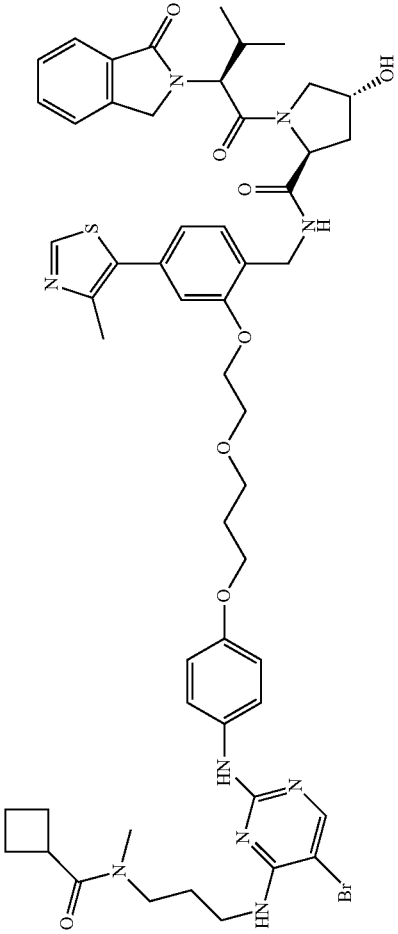 | B |

TABLE 4-continued

Effect of linker and VHL structure on TBK1 degradation

| Compound # | Structure | % TBK1 remaining at 1 uM Crmpd** |
|---|---|---|
| 44 | 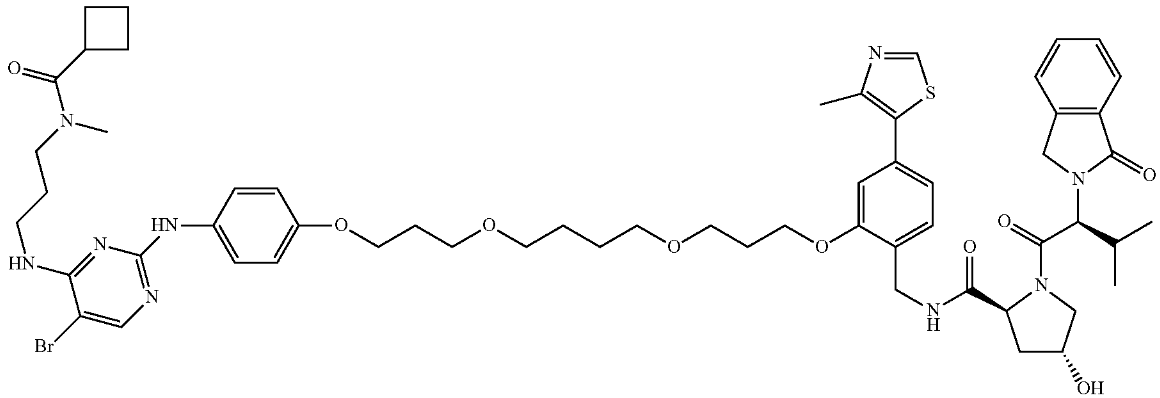 [SMILES: Cc1ncsc1-c1ccc(CNC(=O)[C@@H]2C[C@@H](O)CN2C(=O)[C@H](C(C)C)N2Cc3ccccc3C2=O)c(OCCCOCCCCOCCCOc2ccc(Nc3ncc(Br)c(NCCCN(C)C(=O)C4CCC4)n3)cc2)c1] | B |
| 45 | 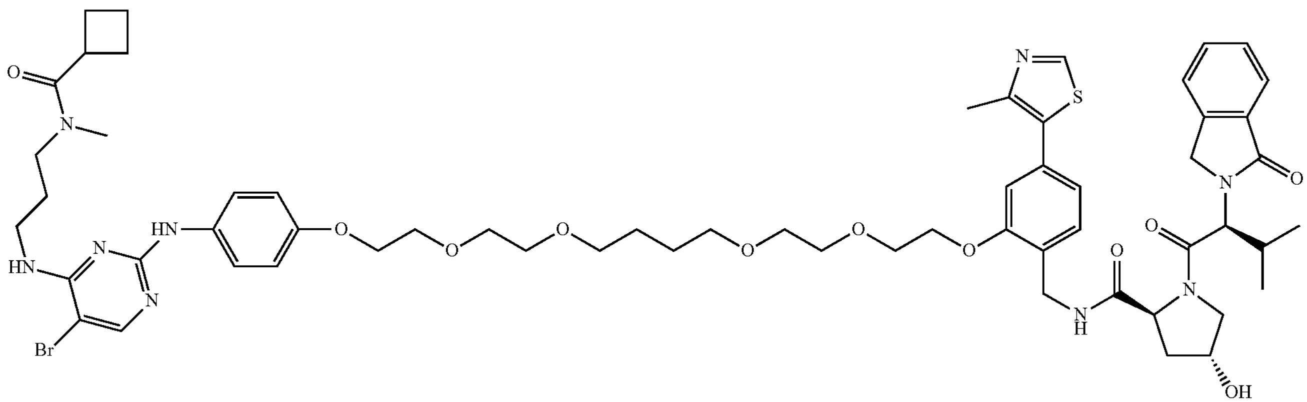 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCCCOCCOCCOc2ccc(Nc3ncc(Br)c(NCCCN(C)C(=O)C4CCC4)n3)cc2)c1] | B |

TABLE 4-continued

Effect of linker and VHL structure on TBK1 degradation

| Compound # | Structure | % TBK1 remaining at 1 uM Crmpd** |
|---|---|---|
| 46 | 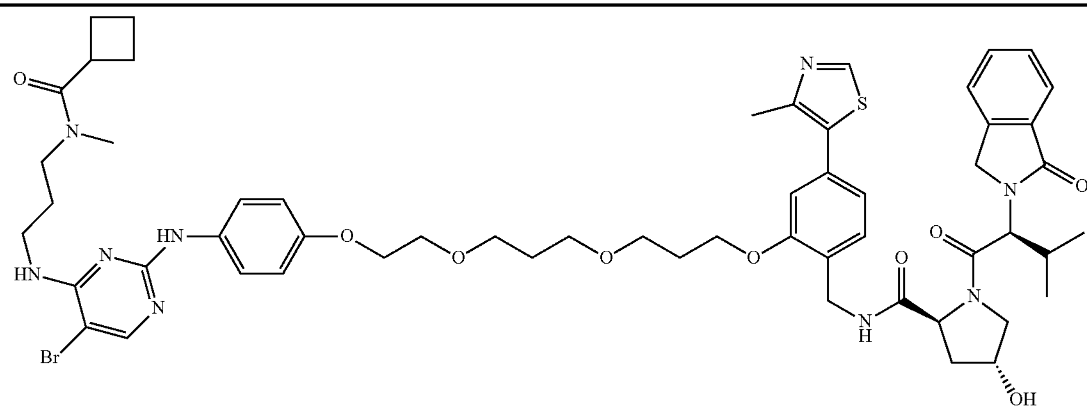 | B |
| 47 | 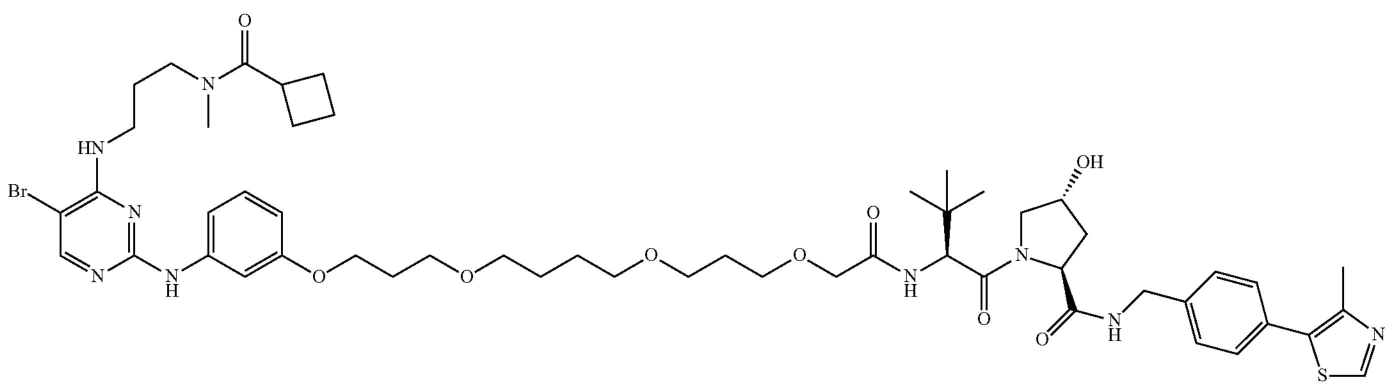 [SMILES: Cc1ncsc1-c1ccc(CNC(=O)[C@@H]2C[C@@H](O)CN2C(=O)[C@@H](NC(=O)COCCCOCCCCOCCCOc2cccc(Nc3ncc(Br)c(NCCCN(C)C(=O)C4CCC4)n3)c2)C(C)(C)C)cc1] | B |

TABLE 4-continued
Effect of linker and VHL structure on TBK1 degradation
| Compound # | Structure | % TBK1 remaining at 1 uM Crmpd** |
|---|---|---|
| 48 | 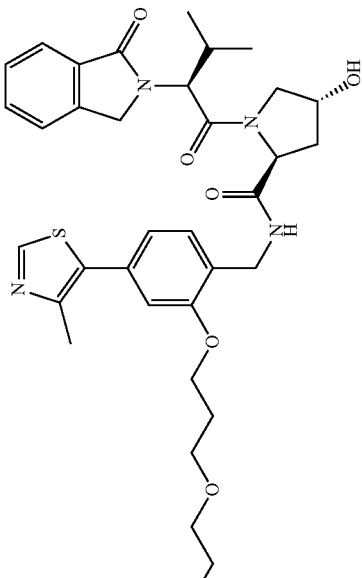 | A |
| 49 | 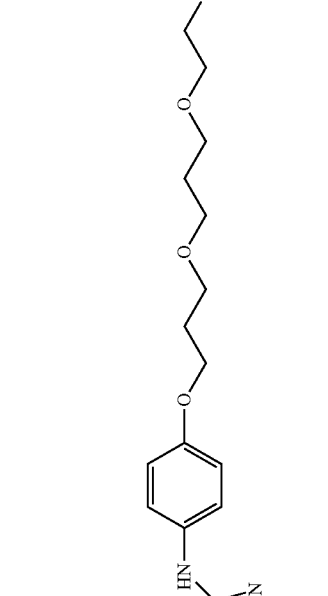 | C |

TABLE 4-continued

Effect of linker and VHL structure on TBK1 degradation

| Compound # | Structure | % TBK1 remaining at 1 uM Crmpd** |
|---|---|---|
| 50 | 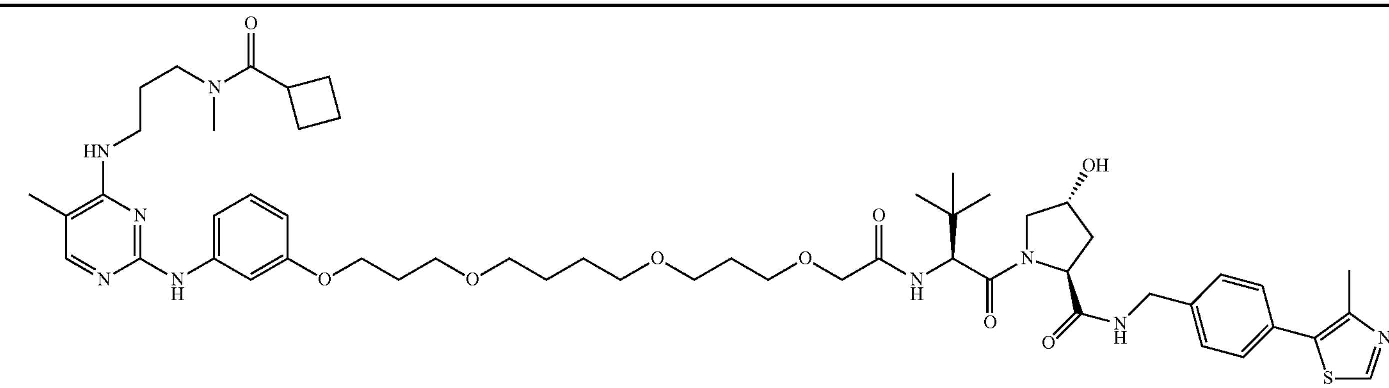 | C |
| 51 | 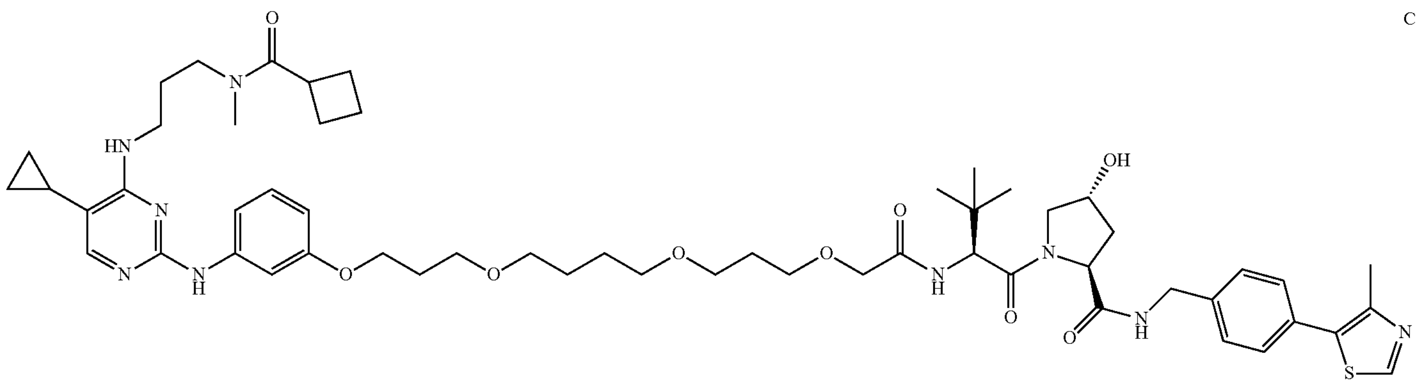 [SMILES: Cc1ncsc1-c1ccc(CNC(=O)[C@@H]2C[C@@H](O)CN2C(=O)[C@@H](NC(=O)COCCCOCCCCOCCCOc2cccc(Nc3ncc(C4CC4)c(NCCCN(C)C(=O)C4CCC4)n3)c2)C(C)(C)C)cc1] | C |

TABLE 4-continued
Effect of linker and VHL structure on TBK1 degradation
| Compound # | Structure | % TBK1 remaining at 1 uM Cmpd** |
|---|---|---|
| 52 | 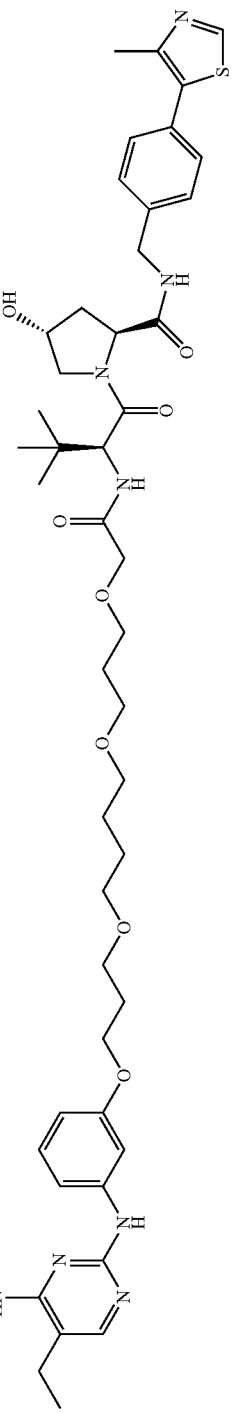 | C |
| 53 | 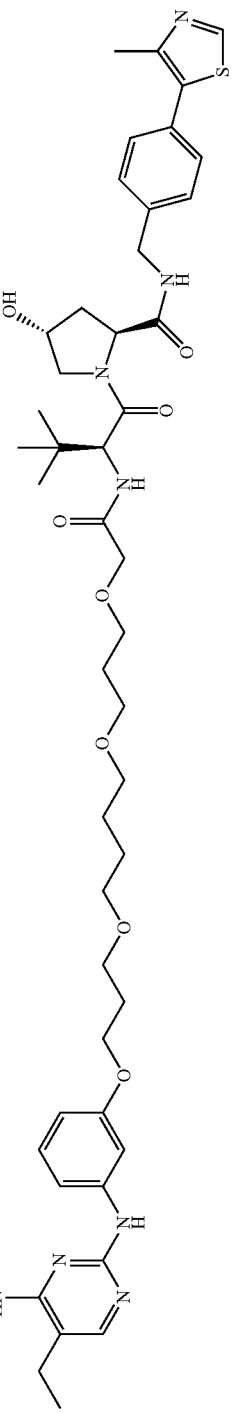 | C |

TABLE 4-continued

Effect of linker and VHL structure on TBK1 degradation

| Compound # | Structure | % TBK1 remaining at 1 uM Cmpd** |
|---|---|---|
| 54 | [structure] | B |

**A: 0-40%
B: 41-80%
C: ≥81%

Figure 8A:
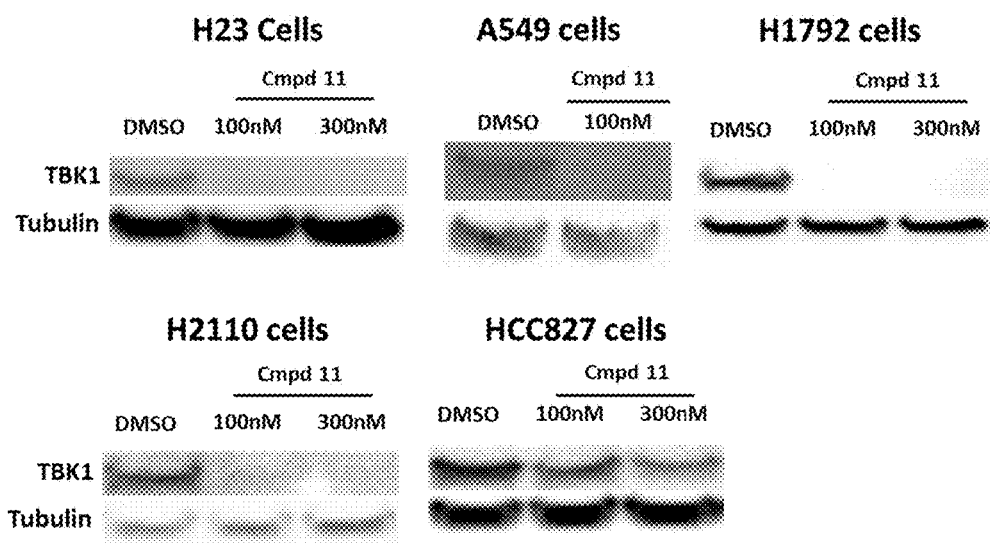
FIG. 8A TBK1 degradation in KRAS mutant and wild type cells.
Figure 8B:
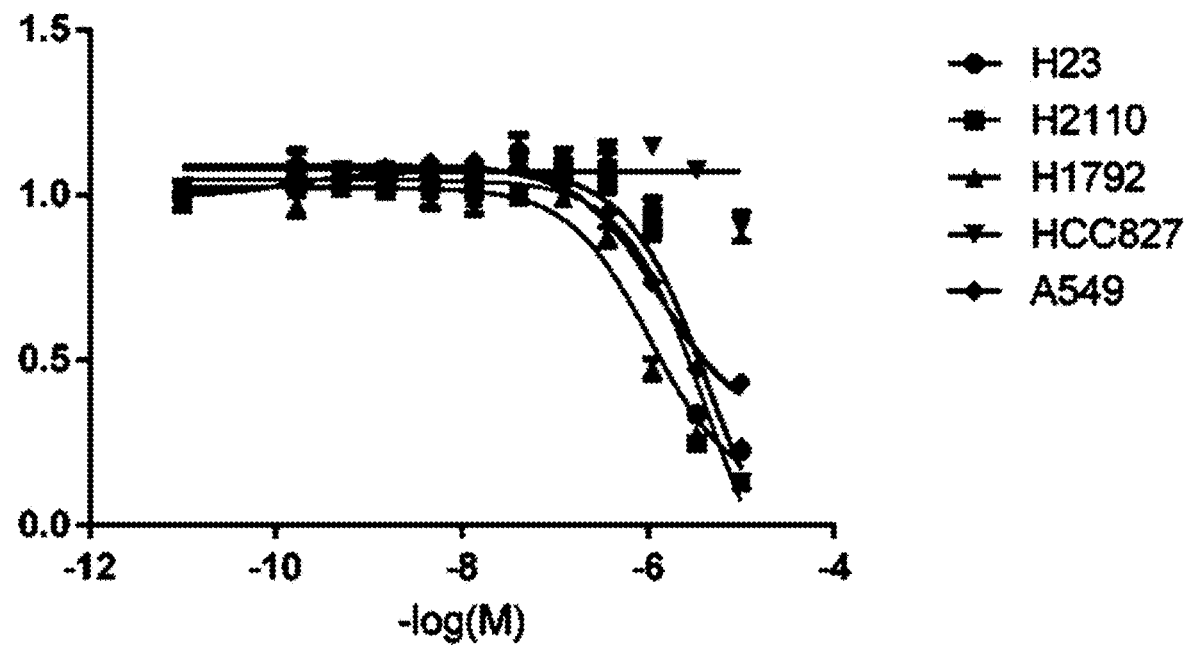
FIG. 8B Antiproliferative effects of TBK1 degrader 11 on KRAS mutant and wild type cells.

The effect of potent TBK1 degrader, PROTAC 11 was also evaluated on cell lines harbouring either wild-type or mutant KRAS. 72 Hour treatment of KRAS mutant cell lines H23, A549 and H1792, and KRAS wild type cell line H2110 with PROTAC 11, while effecting near complete degradation of TBK1, caused no differential effect on the proliferation of these cells, thus supporting the literature reports that TBK1 was not synthetically lethal in KRAS mutant versus wild type cells (FIGS. 8A & 8B).[refs]

Figure 9:
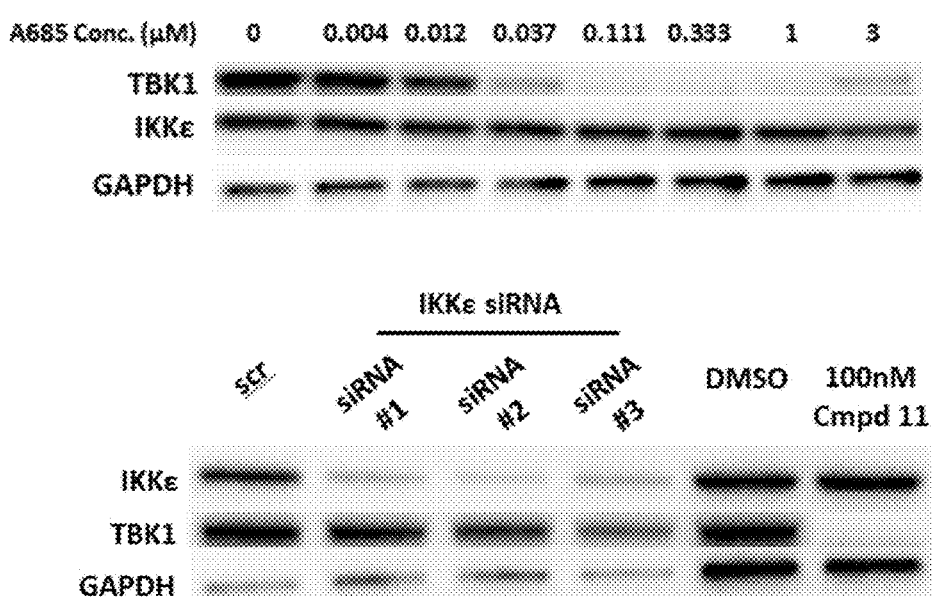
FIG. 9. PROTAC 11 selectively degrades TBK1 over IKKε.

Assessment of the affinity of PROTAC 11 to the closely related kinase IKKε confirmed robust binding with a $K_d$ 70 nM. In the case of TBK1 this is clearly a sufficient level of affinity for degradation (Table 2, e.g. Compound 27), however interestingly was insufficient for IKKε as negligible degradation was observed (FIG. 9).

It was hypothesized that this introduction of degradation selectivity into a relatively unselective ligand may result from a differential presentation of TBK1 and its surface lysines to VHL and its reactive E2-ubiquitin thioester component, as compared to IKKε, and therefore a different efficiency of the transfer of ubiquitin to TBK1 (FIG. 1). Other potential explanations include an increased rate of deubiquitinylation in the case of IKKε, or that IKKε ubiquitinylation leads to compartmentalization versus degradation in the case of IKKε.

In conclusion, a process for the rapid generation of potent, VHL and proteasome-dependent PROTAC degraders of TBK1, through a systematic survey of connector length and ligand affinities has been described. It has been also demonstrated that PROTACs can provide greater degradation potency and selectivity than that anticipated based on the potency and selectivity of the component ligands. In concert with the prevailing literature opinion, it has been also demonstrated that deletion of TBK1 via PROTAC-mediated degradation caused no differential effect on the proliferation between KRAS mutant and KRAS wild type cells.

Assays, Synthetic and Analytical Methods

In vitro degradation assay protocol for compounds 3-33: Panc02.13 cells were purchased from ATCC and cultured in RPMI-1640 (Gibco), supplemented with 15% FBS (ATCC) and 10 Units/mL human recombinant insulin (Gibco). PROTAC treatments were carried out in 12-well plates for 16 h. TLR3 agonist Poly I:C (Invivogen; tlr1-pic) was added for the final 3 h. Cells were harvested, and lysed in RIPA buffer (50 mM Tris pH8, 150 mM NaCl, 1% Tx-100, 0.1% SDS, 0.5% Sodium Deoxycholate) supplemented with protease and phosphatase inhibitors. Lysates were clarified at 16,000 g for 10 minutes, and supernatants were separated by SDS-PAGE. Immunoblotting was performed using standard protocols. The antibodies used were TBK1 (Cell Signaling#3504), pIRF3 (abcam#ab76493), and GAPDH (Cell Signaling#5174).

In Vitro Degradation Assay Protocol for Compounds 34-57

MDA MB 231 cells were purchased from ATCC and cultured in RPMI-1640 (Gibco), supplemented with 10% FBS (Gibco). PROTAC treatments were carried out in 24-well plates for 16 h. Cells were harvested, and lysed in RIPA buffer (50 mM Tris pH8, 150 mM NaCl, 1% Tx-100, 0.1% SDS, 0.5% Sodium Deoxycholate) supplemented with protease and phosphatase inhibitors. Lysates were clarified at 16,000 g for 10 minutes, and supernatants were separated by SDS-PAGE. Immunoblotting was performed using standard protocols. The antibodies used were TBK1 (Cell Signaling#3504) and GAPDH (Cell Signaling#5174).

Representative Experimental Procedure (Compound 11)

Synthetic Scheme:

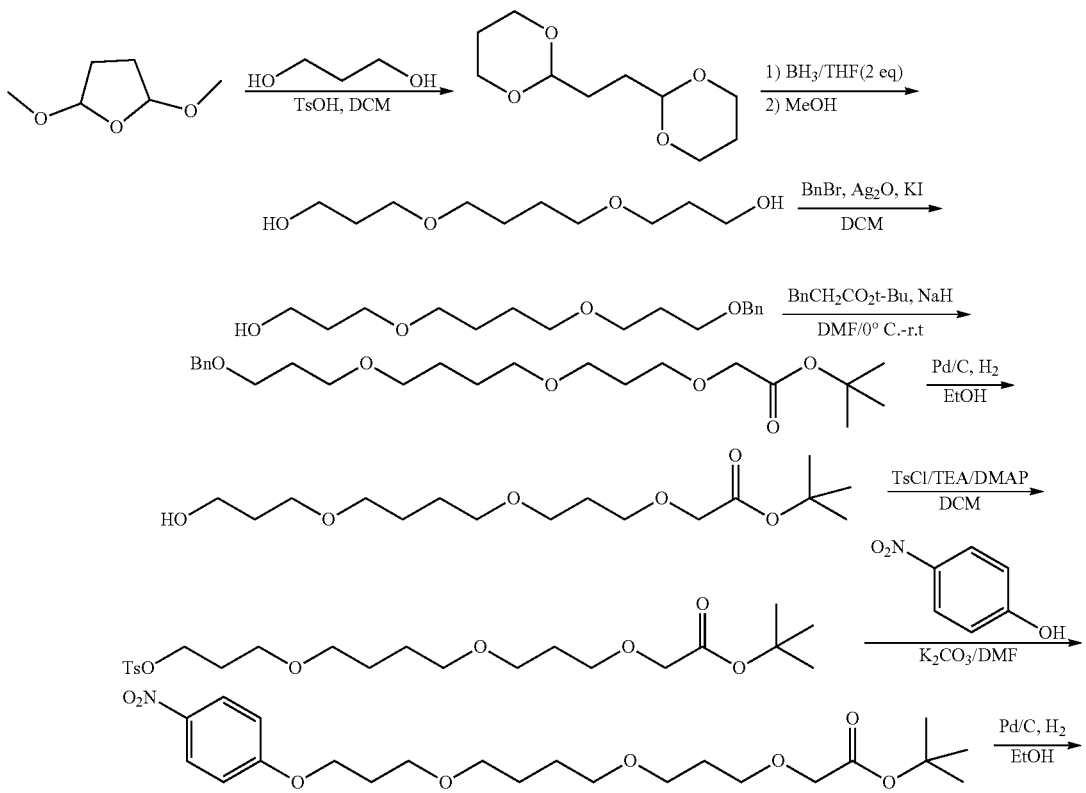

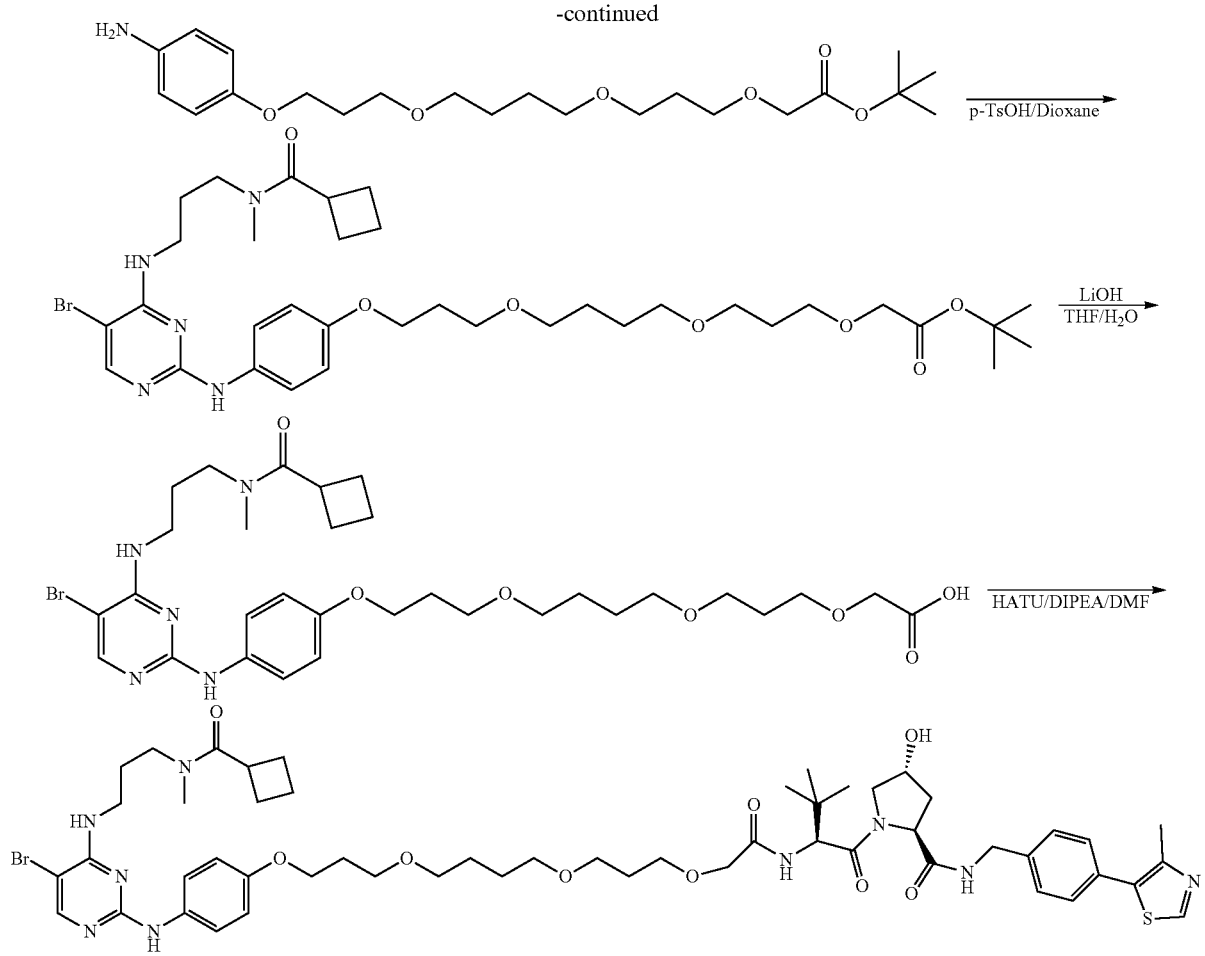

1,2-Di(1,3-dioxan-2-yl)ethane

A mixture of 2,5-dimethoxytetrahydrofuran (20 g, 132 mmol), 1,3-propanediol (120 g, 1.5 mol) and p-TsOH.H$_2$O (2.5 g, 15.1 mmol) in DCM (500 mL) was stirred at 40° C. for 16 h. The reaction was quenched with 1N NaHCO$_3$. The organic phase was washed with water, brine, dried over Na$_2$SO$_4$, filtered and concentrated. The residue was purified by silica gel chromatography eluting with 10-30% EtOAc in hexane to afford 1,2-di(1,3-dioxan-2-yl)ethane (22.5 g, 74%) as white solid. $^1$HNMR (400 MHz, CDCl$_3$): δ 1.30-1.34 (m, 2H), 1.69-1.70 (m, 4H), 2.01-2.11 (m, 2H), 3.71-3.78 (m, 4H), 4.07-4.11 (m, 4H), 4.51-4.55 (m, 2H).

3,3'-(Butane-1,4-diylbis(oxy))bis(propan-1-ol)

To a solution of 1,2-di(1,3-dioxan-2-yl)ethane (22.5 g, 113 mmol) in THF (400 mL) was added BH$_3$ THF complex (1M, 282 mmol, 282 mL) slowly at 0° C. After the addition, the reaction was stirred at reflux for 48 h. TLC showed the reaction was complete. MeOH (40 mL) was carefully added into the reaction mixture at 0° C. and the resulting solution was stirred at room temperature for additional 2 h. The volatiles were evaporated and the residue was purified by silica gel chromatography eluting with 6-8% MeOH in DCM to afford 3,3'-(butane-1,4-diylbis(oxy))bis(propan-1-ol) (7.5 g, 32%) as colorless oil. $^1$HNMR (400 MHz, CDCl$_3$): δ 1.62-1.65 (m, 4H), 1.79-1.85 (m, 4H), 2.79 (br, 2H), 3.45-3.47 (m, 4H), 3.60 (t, J=6.0 Hz, 4H), 3.75 (t, J=5.6 Hz, 4H).

3-(4-(3-(Benzyloxy)propoxy)butoxy)propan-1-ol

To a mixture of 3,3'-(butane-1,4-diylbis(oxy))bis(propan-1-ol) (14 g, 68 mmol), Ag$_2$O (23.6 g, 102 mmol) and KI (4.5 g, 27 mmol) in DCM (120 mL) was added benzyl bromide (12.8 g, 74.7 mmol) dropwise at room temperature. The resulting mixture was stirred at room temperature for 12 h. The solid was removed by filtration and washed with DCM. The combined organic solution was concentrated and the residue was purified by silica gel chromatography eluting with 20% EtOAc in hexane to afford 3-(4-(3-(benzyloxy)propoxy)butoxy)propan-1-ol (7.8 g, 39%) as colorless oil. LCMS: 297.3 [M+1]$^+$. $^1$HNMR (400 MHz, CDCl$_3$): δ 1.60-1.63 (m, 4H), 1.80-1.89 (m, 4H), 2.52 (t, J=5.6 Hz, 1H), 3.40-3.46 (m, 4H), 3.49-3.62 (m, 6H), 3.74-3.78 (m, 2H), 4.50 (s, 2H), 7.27-7.34 (m, 5H).

$^t$Butyl 1-phenyl-2,6,11,15-tetraoxaheptadecan-17-oate

To a mixture of 3-(4-(3-(benzyloxy)propoxy)butoxy)propan-1-ol (7.8 g, 26.3 mmol) in dry DMF (75 mL) was added NaH (60%, 1.9 g, 47.3 mmol) at 0° C. slowly, and the resulting mixture was stirred at room temperature for 1.5 h.

t-Butyl bromoacetate (12.7 g, 65.8 mmol) was added into the reaction mixture at 0° C. dropwise and the resulting mixture was allowed to stir at room temperature for 15 h. The mixture was carefully quenched with water with ice-water cooling and extracted with EtOAc. The organic phase was washed with brine, dried over anhydrous $Na_2SO_4$, filtered and concentrated. The residue was purified by silica gel chromatography eluting with 20-50% EtOAc in hexane to afford the title compound (2.4 g, 22%). LCMS: 469.4 [M+1]$^+$. $^1$HNMR (400 MHz, CDCl$_3$): δ 1.47 (s, 9H), 1.59-1.62 (m, 4H), 1.86-1.91 (m, 4H),3.40-3.43 (m, 4H), 3.49-3.57 (m, 6H), 3.64 (t, J=6.4 Hz, 2H), 4.18 (s, 2H), 4.50 (s, 2H), 4.56 (s, 2H), 7.27-7.36 (m, 5H).

$^t$Butyl 2-(3-(4-(3-hydroxypropoxy)butoxy)propoxy)acetate

A solution of tert-butyl 1-phenyl-2,6,11,15-tetraoxaheptadecan-17-oate (2.4 g, 5.1 mmol), Pd/C (10%, 100 mg) in EtOH (50 mL) was stirred at room temperature 16 h under $H_2$ atmosphere. Pd/C was removed by filtration and washed with EtOH. The combined organic phase was concentrated to afford the title compound (1.8 g, 93%) as brown oil. It was used in next step without further purification.
$^1$HNMR (400 MHz, CDCl$_3$): δ 1.48 (s, 9H), 1.62-1.63 (m, 4H), 1.81-1.91 (m, 4H),2.55 (br, 1H), 1.86-1.91 (m, 4H), 3.41-3.47 (m, 4H), 3.51 (t, J=6.4 Hz, 2H), 3.60-3.66 (m, 4H), 3.77 (t, J=5.4 Hz, 2H), 4.19 (s, 2H), 4.57 (s, 2H).

$^t$Butyl 2-(3-(4-(3-(tosyloxy)propoxy)butoxy) propoxy)acetate

A mixture of tert-butyl 2-(3-(4-(3-hydroxypropoxy)butoxy)propoxy)acetate (800 mg, 2.11 mmol), TsCl (420 mg, 2.54 mmol), TEA (260 mmol, 2.54 mmol) and DMAP (10 mg) in DCM (15 mL) was stirred at room temperature for 8 h. The reaction mixture was diluted with DCM and washed with water and brine. The organic layer was dried over $Na_2SO_4$, filtered and concentrated. The residue was purified by silica gel chromatography eluting with 10-15% EtOAc in hexane to afford the title compound (850 mg, 73%) as colorless oil. LCMS: 533.3[M+1]$^+$. $^1$HNMR (400 MHz, CDCl$_3$): δ 1.48 (s, 9H), 1.53-1.55 (m, 4H), 1.86-1.92 (m, 4H), 2.45 (s, 3H), 3.31-3.34 (m, 2H), 3.39-3.43 (m, 4H), 3.50 (t, J=6.2 Hz, 2H), 3.64 (t, J=6.4 Hz, 2H), 4.13 (t, J=6.2 Hz, 2H), 4.18 (s, 2H), 4.57 (s, 2H),7.34 (d, J=8.0 Hz, 2H), 7.80 (d, J=8.4 Hz, 2H).

$^t$Butyl 2-(3-(4-(3-(4-nitrophenoxy)propoxy)butoxy) propoxy)acetate

A mixture of tert-butyl 2-(3-(4-(3-(tosyloxy)propoxy)butoxy)propoxy)acetate (850 mg, 1.6 mmol), $K_2CO_3$ (552 mg, 4 mmol) and 4-nitrophenol (244 mg, 1.76 mmol) in DMF (5 mL) was stirred at 70° C. for 16 h. The mixture was partitioned between EtOAc and water. The organic phase was washed with brine, dried over anhydrous $Na_2SO_4$, filtered and concentrated. The residue was purified by silica gel chromatography eluting with 20-50% EtOAc in hexane to afford the title compound (650 mg, 81%) as light yellow solid. $^1$H NMR (400 MHz, CDCl$_3$): δ 1.47 (s, 9H), 1.61-1.63 (m, 4H), 1.85-1.91 (m, 2H), 2.06-2.09 (m, 2H), 3.41-3.52 (m, 6H), 3.57-3.65 (m, 4H), 4.18 (s, 2H), 4.57 (s, 2H), 6.96(d, J=9.2 Hz, 2H), 8.20(d, J=9.2 Hz, 2H).

$^t$Butyl 2-(3-(4-(3-(4-aminophenoxy)propoxy)butoxy) propoxy)acetate

A solution of tert-butyl 2-(3-(4-(3-(4-nitrophenoxy)propoxy)butoxy)propoxy)acetate (200 mg, 0.4 mmol), Pd/C (10%, 20 mg) in EtOH (20 mL) was stirred at room temperature under $H_2$ atmosphere. Pd/C was removed by filtration and washed with EtOH. The combined organic phase was concentrated to afford the title compound (120 mg, 64%) as brown oil. The crude product was used directly without purification. $^1$H NMR (400 MHz, CDCl$_3$): δ 1.47 (s, 9H), 1.56-1.63 (m, 4H), 1.87-1.90 (m, 2H), 1.97-2.03 (m, 2H), 3.40-3.45 (m, 4H), 3.50 (t, J=6.4 Hz, 2H), 3.57 (t, J=6.2 Hz, 2H), 3.64 (t, J=6.4 Hz, 2H), 3.98 (t, J=6.4 Hz, 2H), 4.18 (s, 2H), 4.57 (s, 2H), 6.64(d, J=8.8 Hz, 2H), 6.74(d, J=8.8Hz, 2H).

$^t$Butyl2-(3-(4-(3-(4-((5-bromo-4-43-(N-methylcyclobutanecarboxamido)-propyl)-amino)pyrimidin-2-yl)amino)phenoxy)propoxy)butoxy)propoxy)acetate A mixture of tert-butyl 2-(3-(4-(3-(4-aminophenoxy) propoxy)butoxy)propoxy)acetate (120 mg, 0.26 mmol), N-[3-[(5-bromo-2-chloropyrimidin-4-yl)amino]propyl]-N-methylcyclo-butanecarboxamide (96 mg. 0.26 mmol) and TsOH $H_2O$ (23 mg, 0.12 mmol) in dioxane (3 mL) was stirred at 100° C. for 16 h. The reaction mixture was cooled to room temperature, and partitioned between EtOAc and 1N NaHCO$_3$. The organic phase was washed with water, brine, dried over anhydrous $Na_2SO_4$, concentrated. The residue was purified by silica gel chromatography eluting with 2%-5% MeOH in DCM to afford the title compound (120 mg, 58%) as yellow oil. LCMS: 796.3 [M+1]$^+$.

2-(3-(4-(3-(4-((5-Bromo-4-((3-(N-methylcyclobutanecarboxamido)-propyl)amino)pyrimidin-2-yl)amino) phenoxy)propoxy)butoxy)propoxy)acetic acid A mixture of tert-butyl 2-(3-(4-(3-(4-((5-bromo-4-((3-(N-methylcyclobutanecarboxamido)-propyl)amino)pyrimidin-2-yl)amino)phenoxy)propoxy)butoxy)propoxy)acetate (120 mg, 0.15 mmol) and LiOH $H_2O$ (17 mg, 0.4 mmol) in THF (2 mL) and water (0.5 mL) was stirred at room temperature for 2 h. TLC showed the reaction was complete. The reaction mixture was acidified to pH 3-4 with 1M HCl, and the mixture was extracted with DCM, dried over anhydrous $Na_2SO_4$, filtered and concentrated to afford the title compound (100 mg, 98%) as yellow oil which was used in the next step without further purification. LCMS: 682.3 [M+1]$^+$.

(2S,4R)-1-((S)-18-(4-((5-Bromo-4-((3-(N-methylcyclobutanecarboxamido)-propyl) amino)pyrimidin-2-yl)amino)phenoxy)-2-(tert-butyl)-4-oxo-6,10,15-trioxa-3-azaoctadecan-1-oyl)-4-hydroxy-N-(4-(4-methylthiazol-5-yl)benzyl)pyrrolidine-2-carboxamide To a mixture of 2-(3-(4-(3-(4-((5-bromo-4-((3-(N-methylcyclobutanecarboxamido)-propyl)amino)pyrimidin-2-yl) amino)phenoxy)propoxy)butoxy)propoxy)acetic acid (100 mg, 0.147 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (68 mg, 0.147 mmol), and DIPEA (77 mg, 0.6 mmol) in dry DMF (3 mL) was added HATU (114 mg, 0.3 mmol) at 0° C. The resulting mixture was allowed to stir at room temperature for 0.5 h. TLC showed the reaction was complete. The mixture was partitioned between EtOAc and water. The organic phase was washed with water, brine and dried over anhydrous $Na_2SO_4$, filtered and concentrated. The residue was purified by preparative TLC to afford the title compound as white solid (22.5 mg, 15%). LCMS: 1094.4 [M+1]$^+$. $^1$H NMR (400 MHz, CD$_3$OD): δ 1.05 (s, 9H), 1.60-1.64 (m, 4H), 1.80-2.26 (m, 15H), 2.48 (s, 3H), 2.86-2.91 (m, 3H), 3.26-3.28 (m, 1H), 3.40-3.54 (m, 9H), 3.59-3.64 (m, 4H), 3.83-3.88 (m, 2H), 3.97-4.06 (m, 4H), 4.34-4.38 (m, 1H), 4.52-4.61 (m, 3H), 4.71-4.72 (m, 1H), 6.87-6.90 (m, 2H), 7.41-7.49 (m, 6H), 7.87-7.90 (m, 1H), 8.88 (s, 1H).

N-[3-[(5-Bromo-2-chloropyrimidin-4-yl)amino]propyl]-N-methylcyclobutanecarboxamide

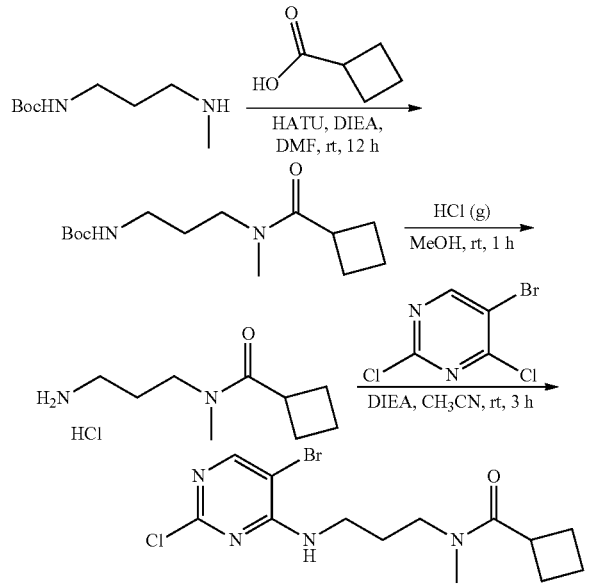

'Butyl N-[3-(1-cyclobutyl-N-methylformamido)propyl]carbamate

Into a 250-mL round-bottom flask purged and maintained with an inert atmosphere of nitrogen, was placed a solution of cyclobutanecarboxylic acid (2.66 g, 26.6 mmol, 1.00 equiv) in N,N-dimethylformamide (100 mL), and DIEA (6.86 g, 53.1 mmol, 2.00 equiv). This was followed by the addition of HATU (12.13 g, 31.9 mmol, 1.20 equiv). The mixture was stirred for 30 min at 0-10° C. To this was added tert-butyl N-[3-(methylamino)propyl]carbamate (5 g, 26.6 mmol, 1.00 equiv). The resulting solution was stirred for 12 h at room temperature. The reaction was then quenched by the addition of 500 mL of water. The resulting solution was extracted with 3×100 mL of ethyl acetate and the organic layers combined. The extracts were washed with 1×100 mL of water and 1×100 mL of brine. The mixture was dried over anhydrous sodium sulfate and concentrated in vacuo. The residue was purified by silica gel chromatography eluting with ethyl acetate/petroleum ether (1:1). This resulted in 5.9 g (82%) of tert-butyl N-[3-(1-cyclobutyl-N-methylformamido)propyl]carbamate as colorless oil. LC-MS (ES$^+$): m/z 271.05[MH$^+$], t$_R$=0.98 min.

N-(3-Aminopropyl)-N-methylcyclobutanecarboxamide hydrochloride

Into a 250-mL round-bottom flask, was placed a solution of tert-butyl N-[3-(1-cyclobutyl-N-methylformamido)propyl]carbamate (13 g, 48.1 mmol, 1.00 equiv) in methanol/HCl (g) (200 mL). The resulting solution was stirred for 1 h at room temperature. The resulting mixture was concentrated under vacuum. This resulted in 9.6 g (97%) of N-(3-aminopropyl)-N-methylcyclobutanecarboxamide hydrochloride as a white solid. LC-MS (ES$^+$): m/z 171.00 [MH$^+$], t$_R$=0.34 min.

N-[3-[(5-Bromo-2-chloropyrimidin-4-yl)amino]propyl]-N-methylcyclobutanecarboxamide Into a 500-mL 3-necked round-bottom flask purged and maintained with an inert atmosphere of nitrogen, was placed a solution of 5-bromo-2,4-dichloropyrimidine (10.55 g, 46.3 mmol, 1.00 equiv) in CH$_3$CN (250 mL). This solution was cooled to 0° C. and treated with dropwise DIEA (18 g, 139.3 mmol, 3.00 equiv) and then N-(3-aminopropyl)-N-methylcyclobutanecarboxamide hydrochloride (9.6 g, 46.4 mmol, 1.00 equiv) batchwise. The resulting solution was stirred for 3 h at room temperature then quenched by the addition of 50 mL of water. The CH$_3$CN was removed in vacuo and the resulting solution further diluted with 100 mL of water. This mixture was extracted with 3×100 mL of ethyl acetate and the organic layers combined, washed with 1×100 mL of brine and dried over anhydrous sodium sulfate, and concentrated in vacuo. The resulting residue was washed with 2×100 mL of ethyl acetate/petroleum ether (1/5) and the solids collected by filtration. This resulted in 11.3 g (67%) of N-[3-[(5-bromo-2-chloropyrimidin-4-yl)amino]propyl]-N-methylcyclobutanecarboxamide as a white solid. $^1$H NMR (400 MHz, CDCl$_3$) δ 8.09 (s, 1H), 7.20 (b, 1H), 3.49-3.47 (m, 4H), 3.46-3.28 (m, 2H), 2.41-2.31 (m, 2H), 2.24-2.16 (m, 2H), 2.05-1.80 (m, 2H), 1.80-1.70 (m, 2H); LC-MS (ES$^+$): m/z 362.90, 364.90 [MH+], t$_R$=2.85 min.
Analytical Characterization of TBK1 Compounds:

| Compound # | MH+ (1) | MH+ (2) |
|---|---|---|
| 7 | 1038.37 | 1040.37 |
| 34 | 1054.35 | 1056.35 |
| 16 | 1170.46 | 1172.46 |
| 3 | 978.37 | 980.37 |
| 35 | 1098.39 | 1100.39 |
| 36 | 1142.41 | 1144.42 |
| 37 | 1230.47 | 1232.47 |
| 4 | 994.36 | 996.36 |
| 13 | 1126.44 | 1128.44 |
| 38 | 1186.44 | 1188.44 |
| 39 | 1038.36 | 1040.37 |
| 40 | 1110.51 | 1112.51 |
| 6 | 1022.47 | 1024.47 |
| 11 | 1094.53 | 1096.54 |
| 5 | 1006.46 | 1008.46 |
| 8 | 1050.49 | 1052.49 |
| 41 | 1082.46 | 1084.46 |
| 42 | 1200.52 | 1202.53 |
| 10 | 1082.48 | 1084.48 |
| 43 | 1068.45 | 1070.45 |
| 44 | 1154.53 | 1156.53 |
| 45 | 1214.55 | 1216.55 |
| 9 | 1066.50 | 1068.50 |
| 12 | 1106.57 | 1108.57 |
| 14 | 1138.56 | 1140.56 |
| 17 | 1182.59 | 1184.59 |
| 46 | 1126.50 | 1128.51 |
| 15 | 1152.57 | 1154.58 |
| 47 | 1168.57 | 1170.57 |
| 48 | 1242.61 | 1244.61 |
| 49 | 1094.45 | 1096.46 |
| 50 | 1028.57 | — |
| 51 | 1054.58 | — |
| 28 | 1054.58 | — |
| 25 | 1028.56 | — |

-continued

| Compound # | MH+ (1) | MH+ (2) |
|---|---|---|
| 26 | 1042.58 | — |
| 52 | 1042.58 | — |
| 27 | 1040.56 | — |
| 53 | 1041.06 | — |
| 54 | 1040.56 | — |
| 18 | 1094.43 | 1096.44 |
| 19 | 1014.52 | — |
| 20 | 1048.42 | 1050.42 |
| 21 | 1082.42 | — |
| 24 | 1032.43 | — |
| 23 | 1140.33 | — |
| 22 | 1068.47 | — |
| 29 | 1038.27 | 1040.28 |
| 30 | 1052.29 | 1054.29 |
| 31 | 1066.30 | 1068.30 |
| 32 | 1080.32 | 1082.32 |
| 33 | 1080.32 | 1082.32 |
| 55 | 1210.41 | 1212.41 |
| 56 | 1238.44 | 1240.44 |
| 57 | 1294.50 | 1296.50 |

Method to synthesize novel bifunctional molecules, which contains a TBK1 recruiting moiety and an E3 Ligase recruiting moiety, through PROTAC technology is described. PROTAC mediated protein degradation provides a promising strategy in targeting the "undruggable" pathological proteins by traditional approaches.

As described herein, in one aspect the disclosure provides bifunctional compounds comprising the chemical structure: TBM-L-ULM, wherein TBM is a TBK1 binding moiety; L is absent (a bond) or a chemical linker; and ULM is an E3 ubiquitin ligase binding moiety.

In any of the aspects or embodiments described herein, the TBM has the structure:

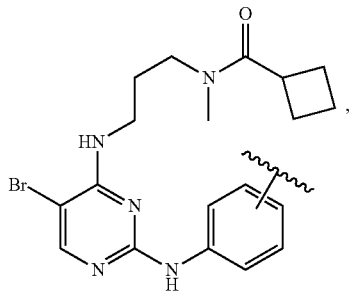

wherein the TBM is covalently coupled to an ULM via an L group.

In any of the aspects or embodiments described herein, the ULM is a moiety that binds an E3 ubiquitin ligase selected from the group consisting of Von Hippel-Lindau (VHL) E3 ubiquitin ligase, IAP, cereblon, and MDM2 as described herein.

In any of the aspects or embodiments described herein, the bifunctional compound comprise a linker (L) group having the structure: -$A_1$ ... $A_q$-, wherein $A_1$ is coupled to the ULM and TBM moiety; and q is an integer greater than or equal to 0.

In any of the aspects or embodiments described herein, each A unit (i.e., $A_1$ to $A_q$) is each independently, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{3-11}$heteocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, wherein $R^{L1}$ or $R^L_2$, each independently, can be linked to other A groups to form cycloalkyl and/or heterocyclyl moiety which can be further substituted with 0-4 $R^{L5}$ groups; and wherein $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$alkyl, $P(O)(OC_{1-8}$alkyl)($C_{1-8}$alkyl), $P(O)(OC_{1-8}$alkyl$)_2$, CC—$C_{1-8}$alkyl, CCH, CH=CH($C_{1-8}$alkyl), C($C_{1-8}$alkyl)×CH($C_{1-8}$alkyl), C($C_{1-8}$alkyl)=C($C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl)CONH($C_{1-8}$ alkyl), $N(C_{1-8}$alkyl)CON($C_{1-8}$alkyl$)_2$, $NHCONH(C_{1-8}$alkyl), $NHCON(C_{1-8}$alkyl$)_2$, $NHCONH_2$, $N(C_{1-8}$alkyl)$SO_2NH(C_{1-8}$alkyl), $N(C_{1-8}$alkyl) $SO_2N(C_{1-8}$alkyl$)_2$, $NHSO_2NH(C_{1-8}$alkyl), $NHSO_2N(C_{1-8}$alkyl$)_2$, or $NHSO_2NH_2$.

In any of the aspects or embodiments described herein, the linker (L) is selected from the group consisting of:

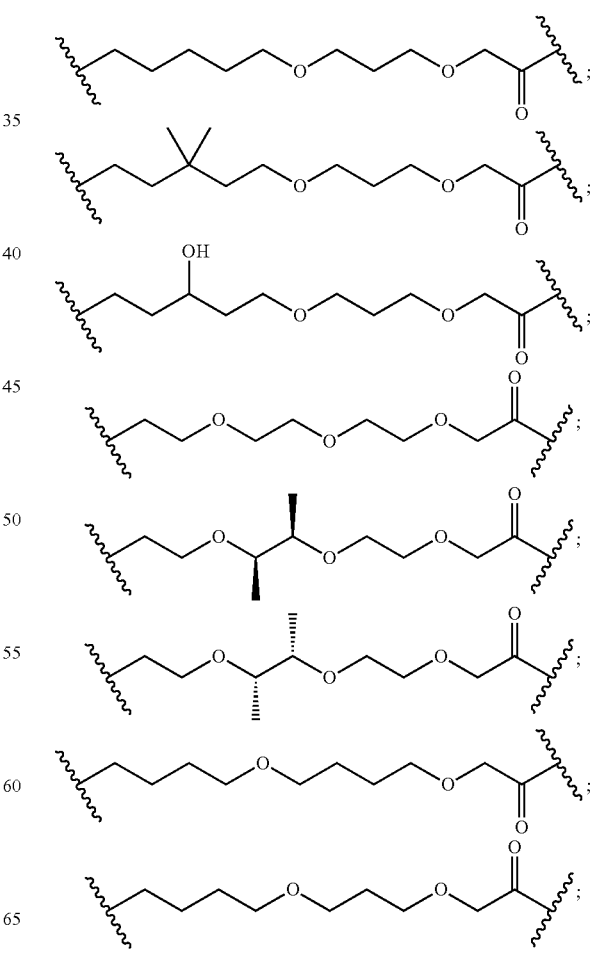

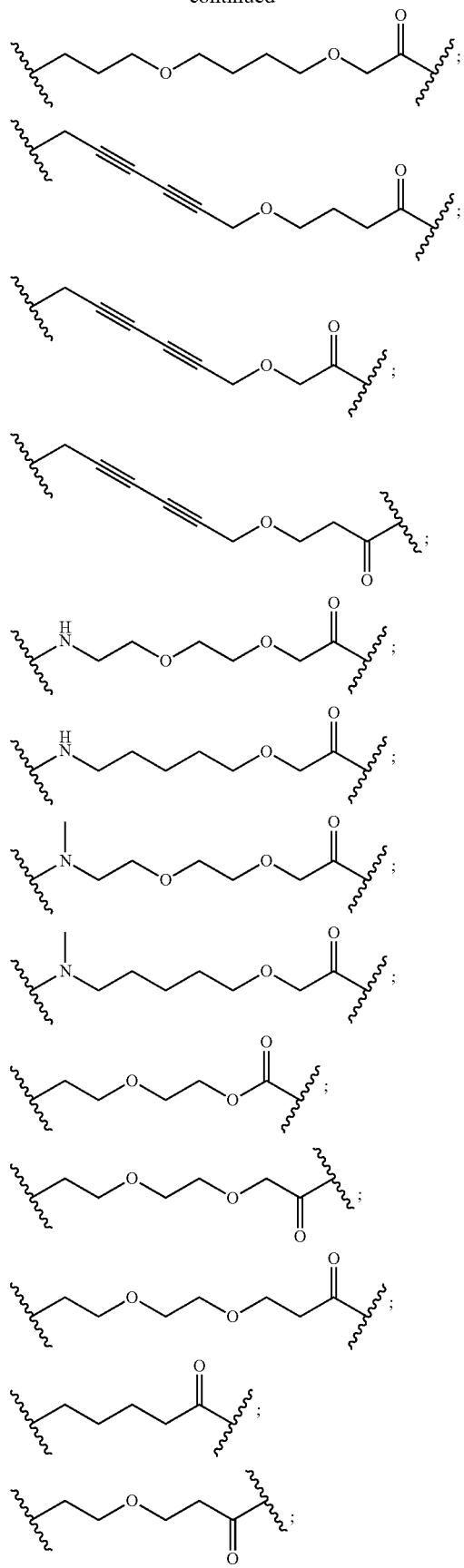
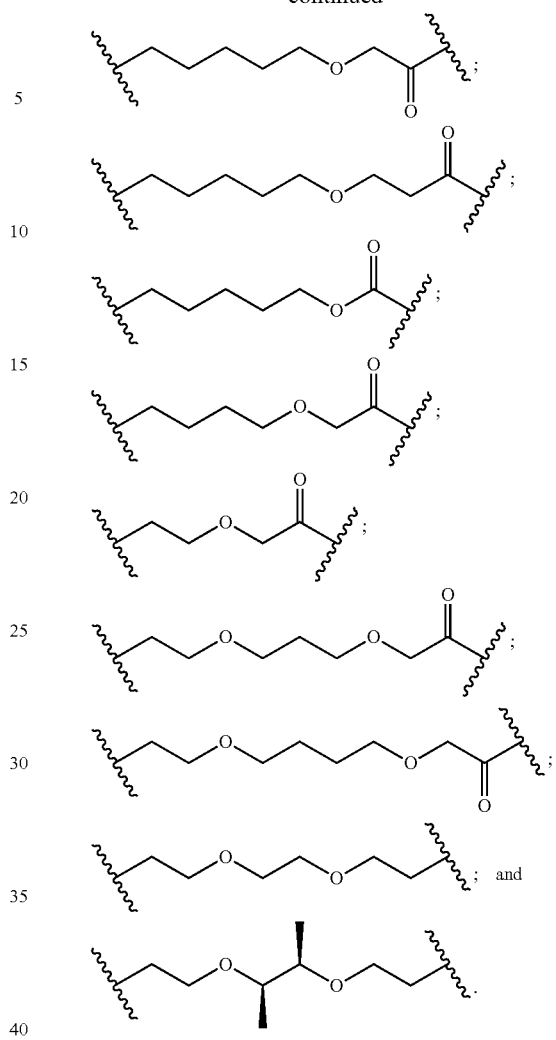

In an additional aspects, the disclosure provides compositions comprising an effective amount of the bifunctional compound as described herein, and a pharmaceutically acceptable carrier.

In any of the aspects or embodiments described herein, the composition can further comprise at least one additional bioactive agent. In any of the aspects or embodiments described herein, the bioactive agent is an anti-cancer agent. In any of the aspects or embodiments described herein, the additional anti-cancer agent is selected from the group consisting of: everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, an androgen receptor inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR₁ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo [2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(But)6, Azgly 10] (pyro-Glu-His-Trp-Ser-Tyr-D-Ser(But)-Leu-Arg-Pro-Azgly-NH₂ acetate [$C_{59}H_{84}N_{18}O_{14}$—($C_2H_4O_2$)x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In any of the aspects or embodiments described herein, the composition can comprise an effective amount of at least two different bifunctional compounds as described herein.

In any of the aspects or embodiments described herein, the compound as described herein can be selected from the group consisting of:

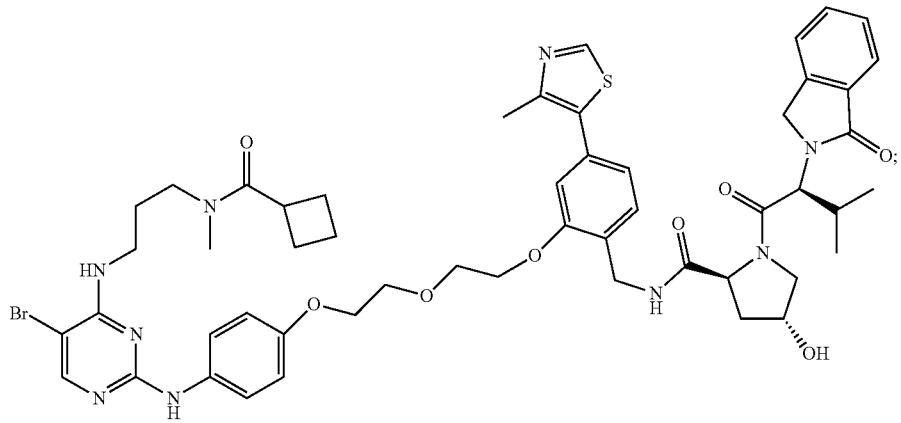

85 86
-continued
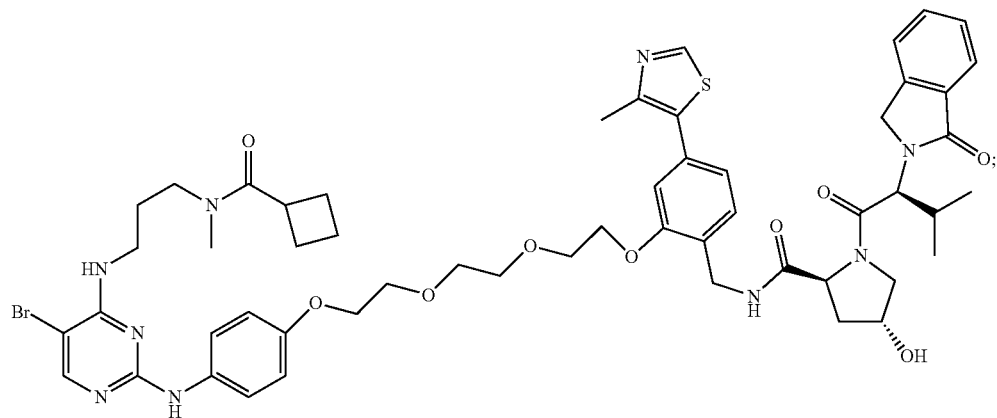
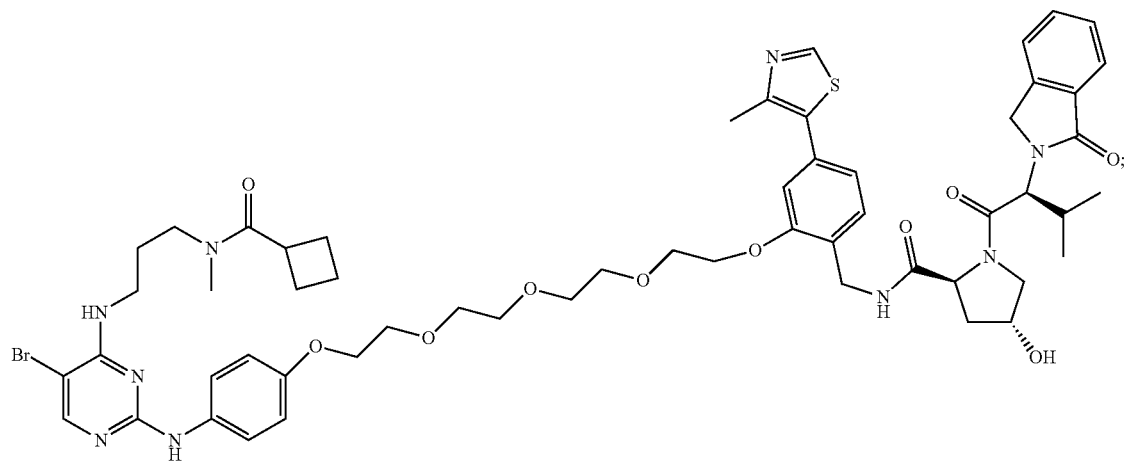
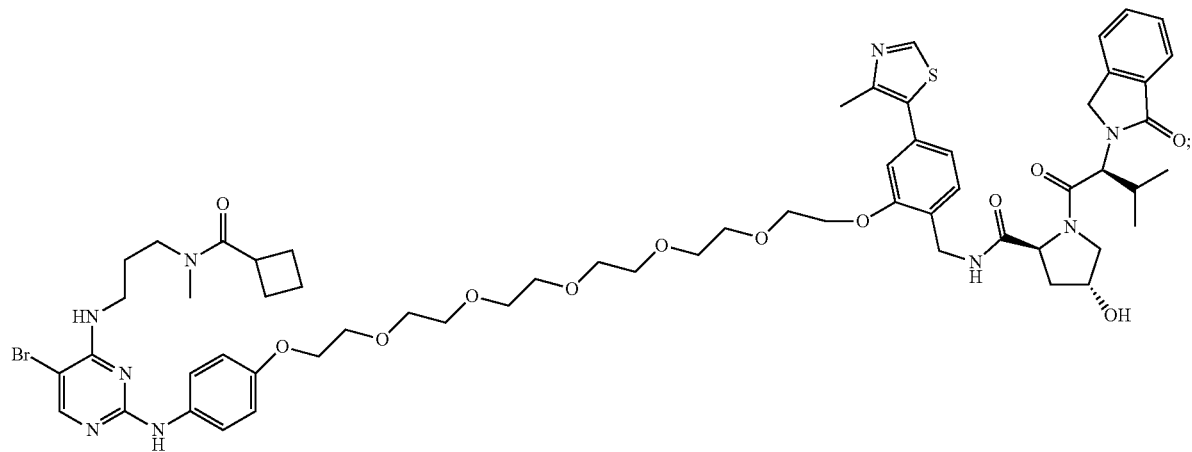

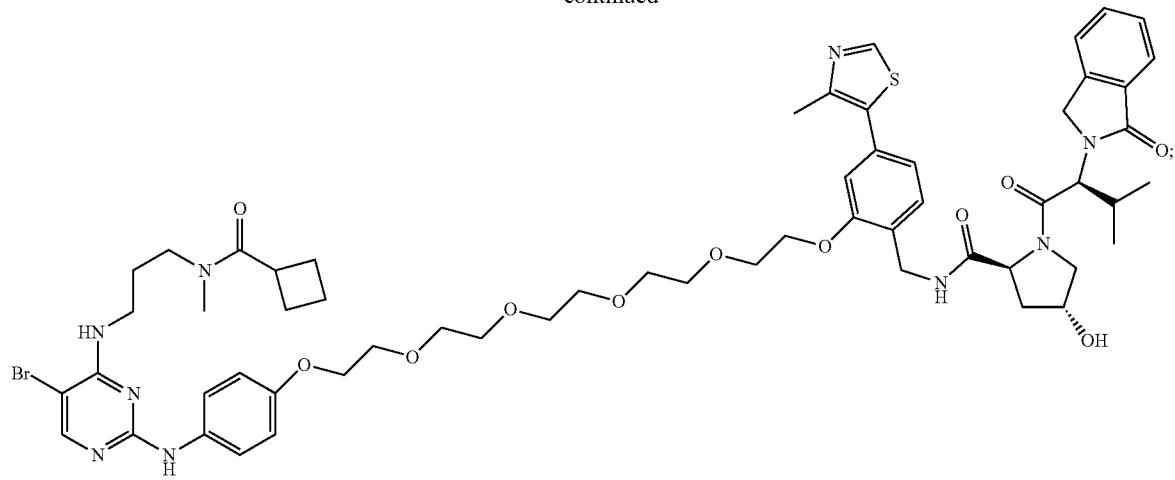
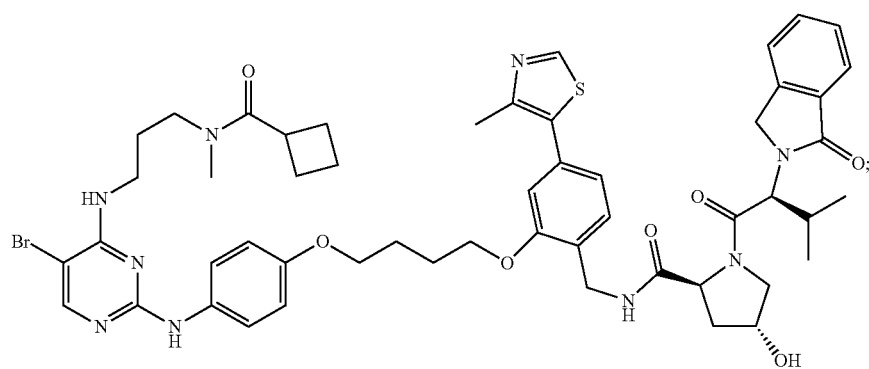
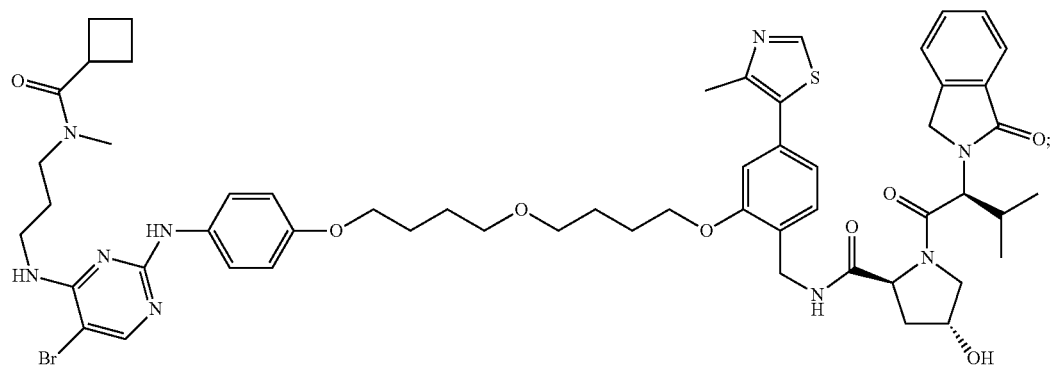
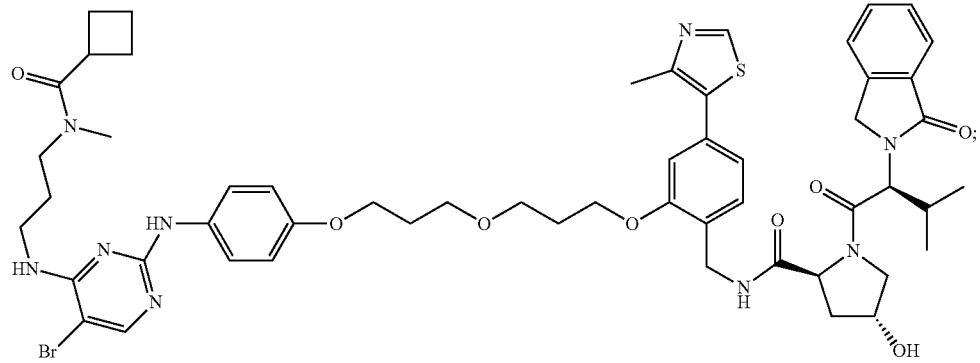

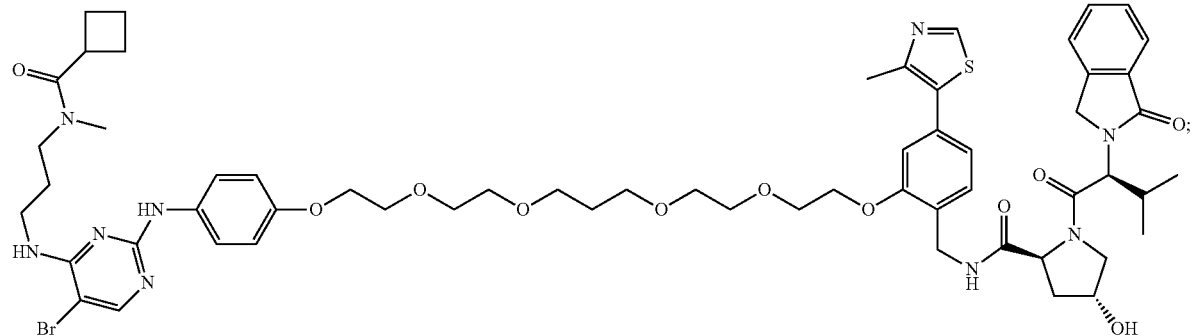
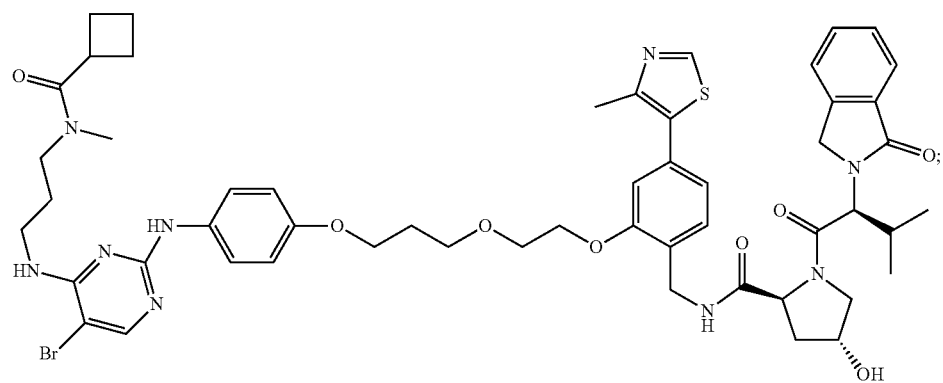
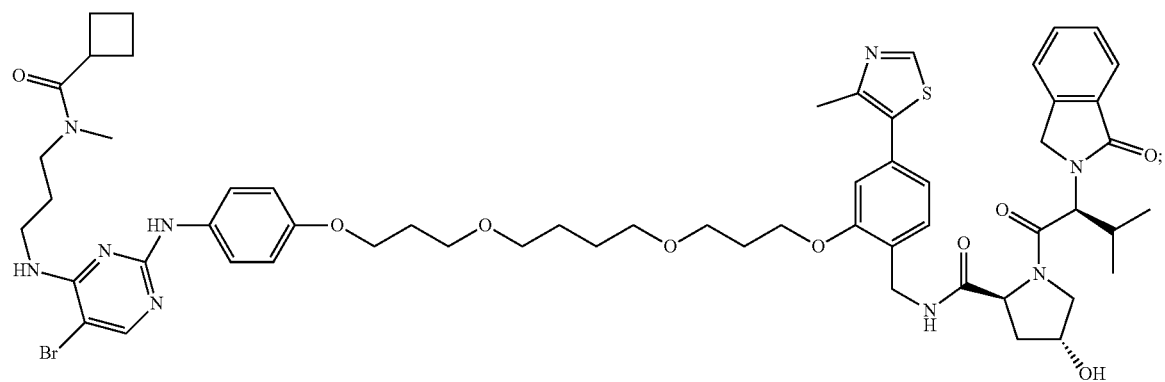
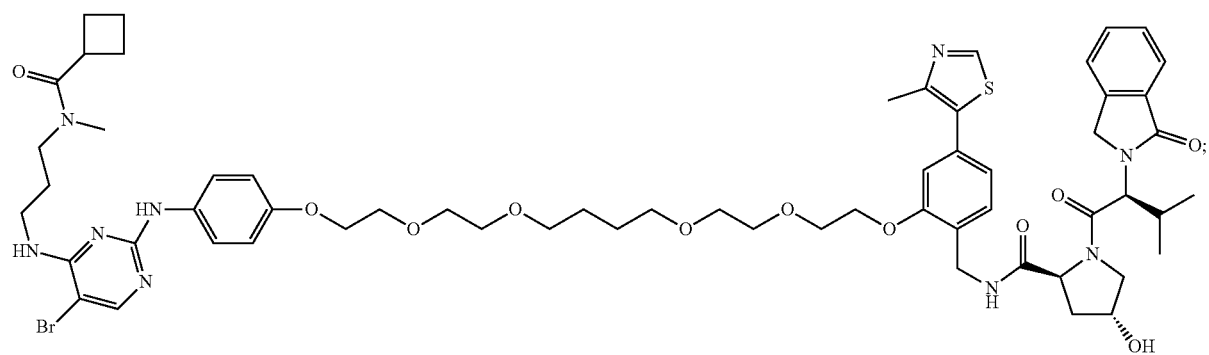

-continued
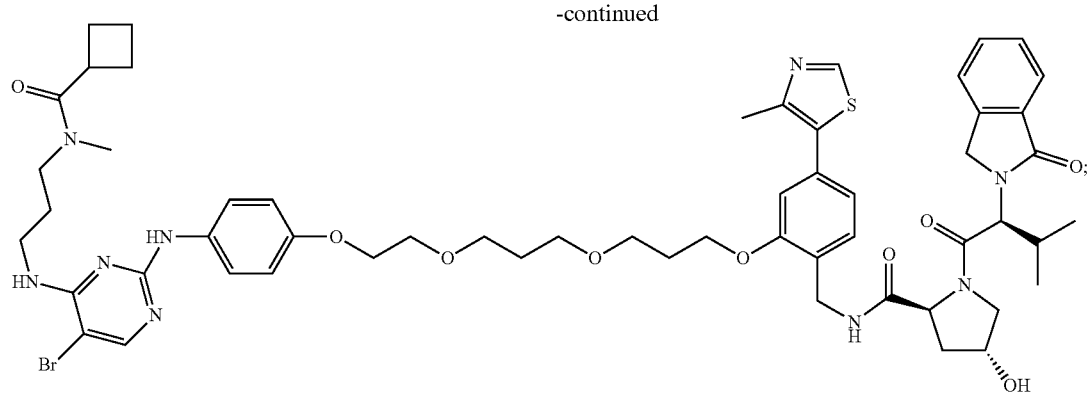
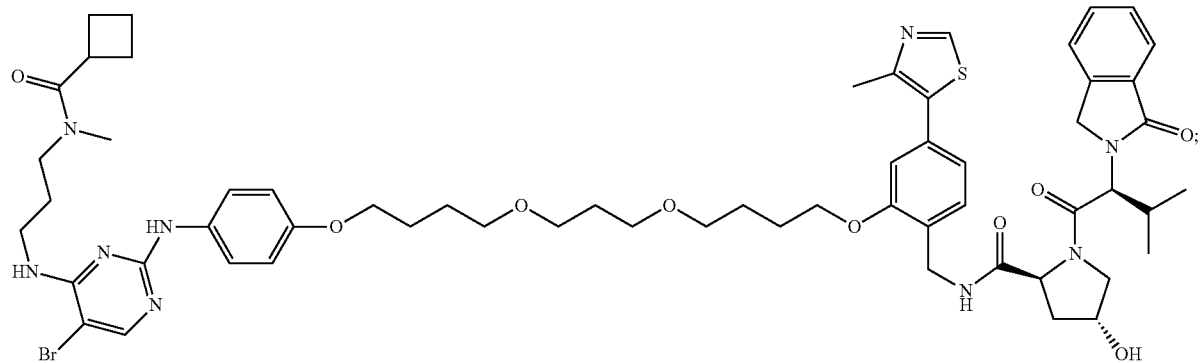
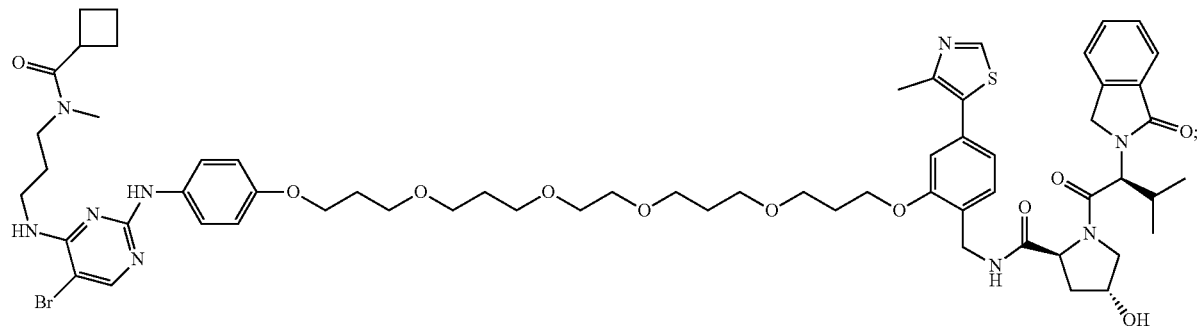
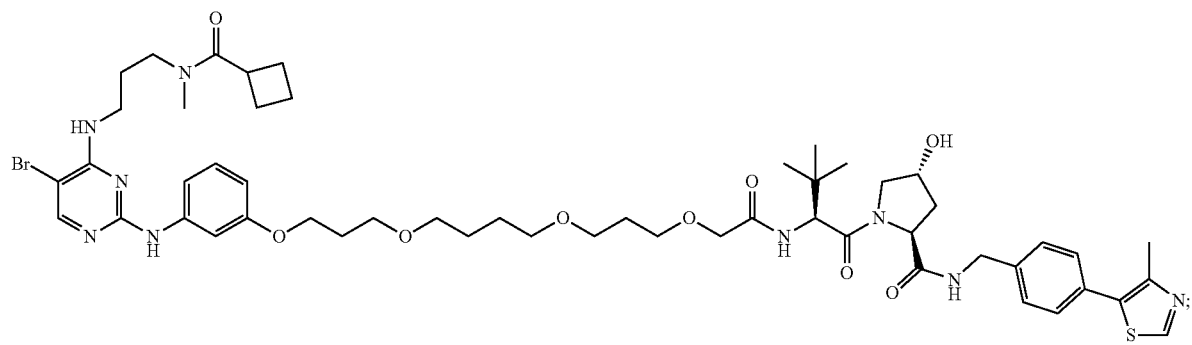

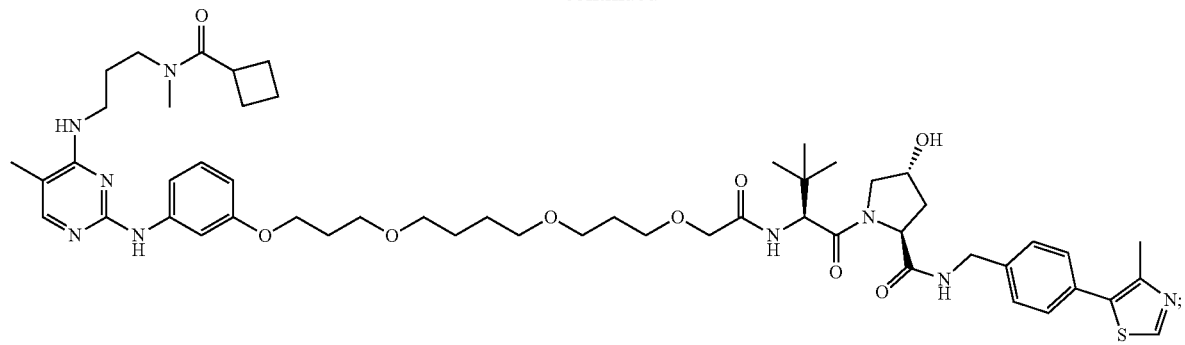
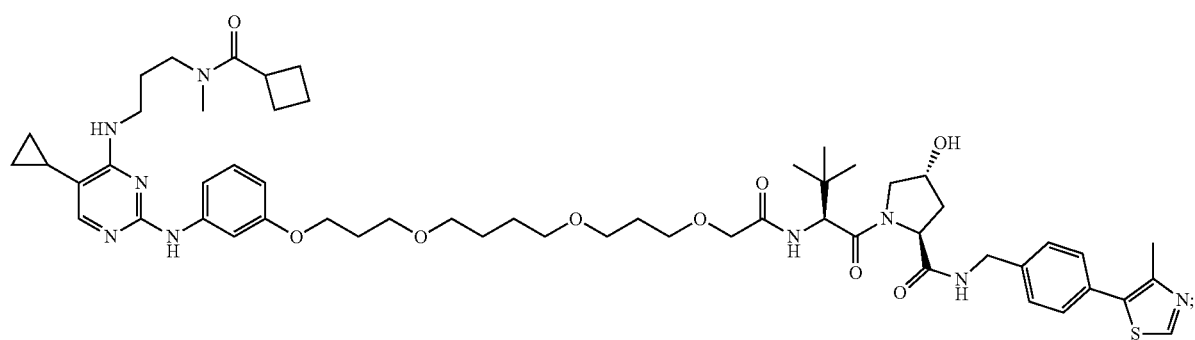
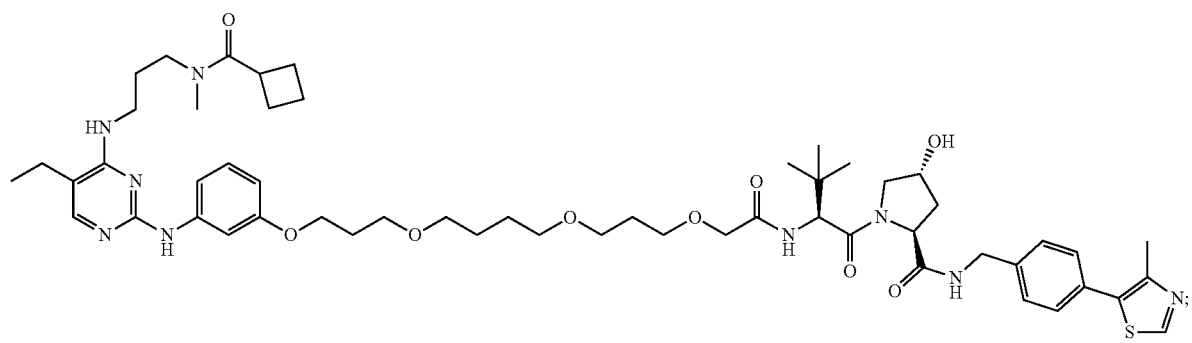
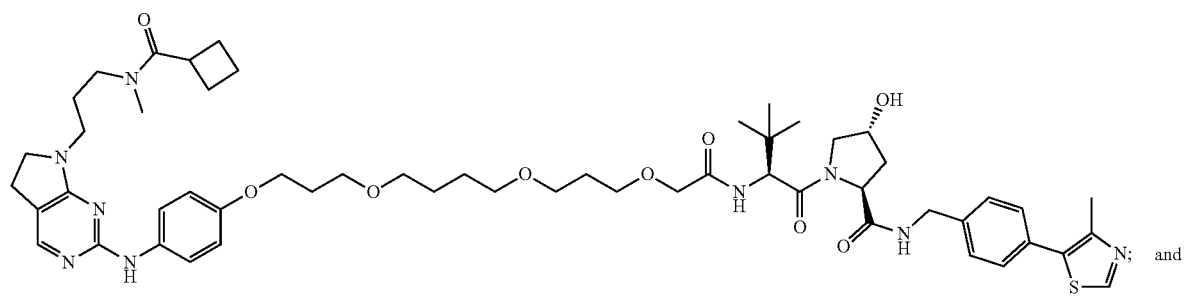
and

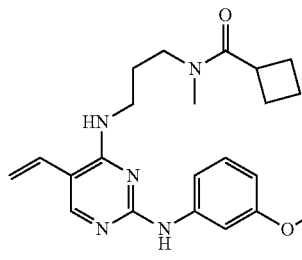

and combinations thereof.

In any of the aspects or embodiments described herein, the disclosure includes compositions comprising one or more of the above-referenced compounds, including effective amounts of the same. In any of the aspects or embodiments, the compositions can further include a pharmaceutically acceptable carrier.

In an additional aspect, the description provides compositions for use in methods of treating a disease or disorder in a subject comprising the steps of administering a composition comprising a pharmaceutically acceptable carrier and an effective amount of a compound as described herein to a subject in need thereof, wherein the compound is effective in treating or ameliorating at least one symptom of the disease or disorder. In any of the aspects or embodiments, the disease or disorder is at least one of cancer, an inflammatory disease, an autoimmune disease, septic shock, or viral infection.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A bifunctional compound comprising the chemical structure:

TBM-L-ULM, wherein:
TBM is a TBK1 binding moiety;
L is a bond or a chemical linker that covalently couples the TBM and the ULM; and
ULM is an E3 ubiquitin ligase binding moiety.

2. The compound of claim 1, wherein the TBM has the structure:

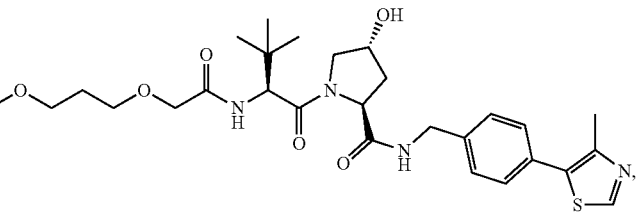

or

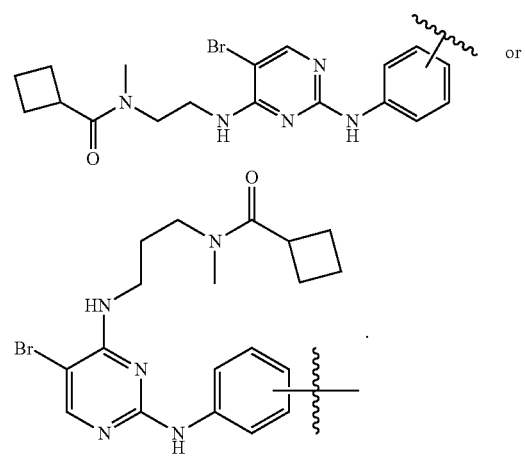

3. The bifunctional compound of claim 1, wherein ULM is a moiety that binds an E3 ubiquitin ligase selected from the group consisting of Von Hippel-Lindau (VHL) E3 ubiquitin ligase, IAP, cereblon, and MDM2.

4. The bifunctional compound of claim 1, wherein the chemical linker (L) is a group having the structure:

-(A')$_q$-, wherein:
-(A')$_q$- is coupled to the ULM and TBM moiety; and
q is an integer greater than or equal to 0.

5. The bifunctional compound of claim 4, wherein each A is independently, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, P(O)$R^{L1}$, P(O)O$R^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{3-11}$heterocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, wherein $R^{L1}$ or $R^{L}{}_2$, each independently, can be linked to other A groups to form cycloalkyl and/or heterocyclyl moeity which can be further substituted with 0-4 $R^{L5}$ groups; and wherein $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$ cycloalkyl$)(C_{1-8}$alkyl$)$, OH, $NH_2$, SH, $SO_2C_{1-8}$ alkyl, $P(O)(OC_{1-8}$alkyl$)(C_{1-8}$alkyl$)$, $P(O)(OC_{1-8}$alkyl$)_2$, CC—$C_{1-8}$alkyl, CCH, CH=CH($C_{1-8}$alkyl), $C(C_{1-8}$alkyl)=CH($C_{1-8}$alkyl), $C(C_{1-8}$alkyl)=$C(C_{1-8}$alkyl$)_2$, $Si(OH)_3$, $Si(C_{1-8}$alkyl$)_3$, $Si(OH)(C_{1-8}$alkyl$)_2$, $COC_{1-8}$ alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl$)CONH(C_{1-8}$alkyl$)$, $N(C_{1-8}$alkyl$)CON(C_{1-8}$alkyl$)_2$, $NHCONH(C_{1-8}$alkyl$)$, $NHCON(C_{1-8}$ alkyl$)_2$, $NHCONH_2$, $N(C_{1-8}$alkyl$)SO_2NH(C_{1-8}$ alkyl$)$, $N(C_{1-8}$alkyl$)SO_2N(C_{1-8}$alkyl$)_2$, $NHSO_2NH(C_{1-8}$ alkyl$)$, $NHSO_2N(C_{1-8}$alkyl$)_2$, $NHSO_2NH_2$.

6. The bifunctional compound of claim 1, wherein the linker (L) is selected from the group consisting of:

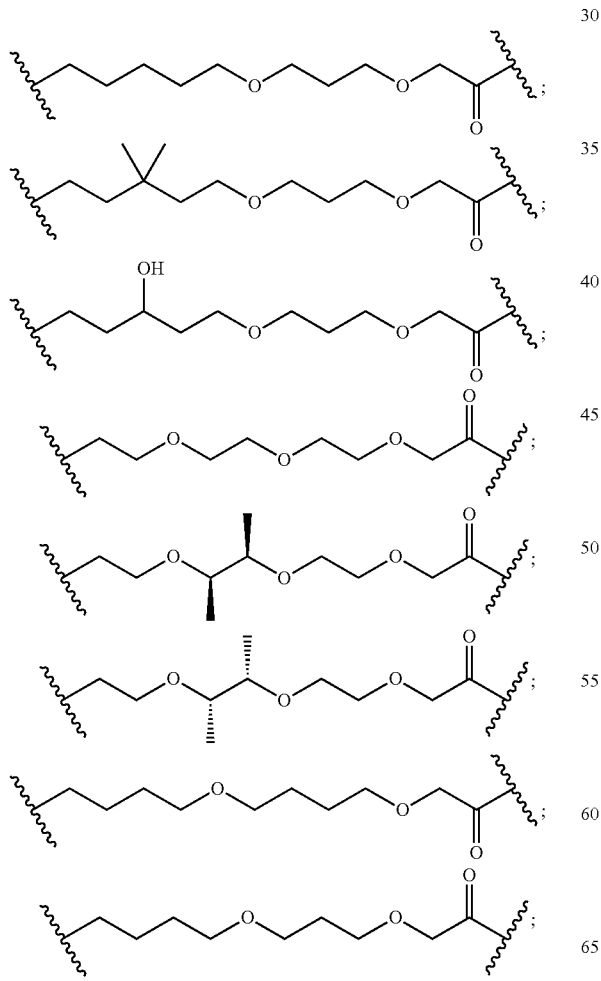
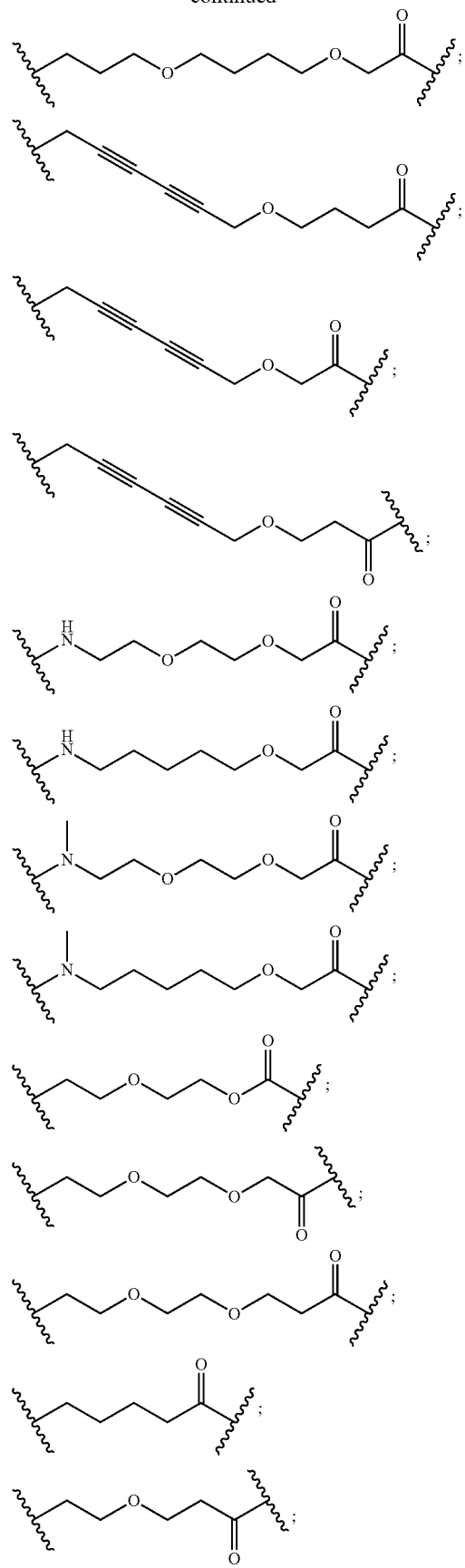

-continued

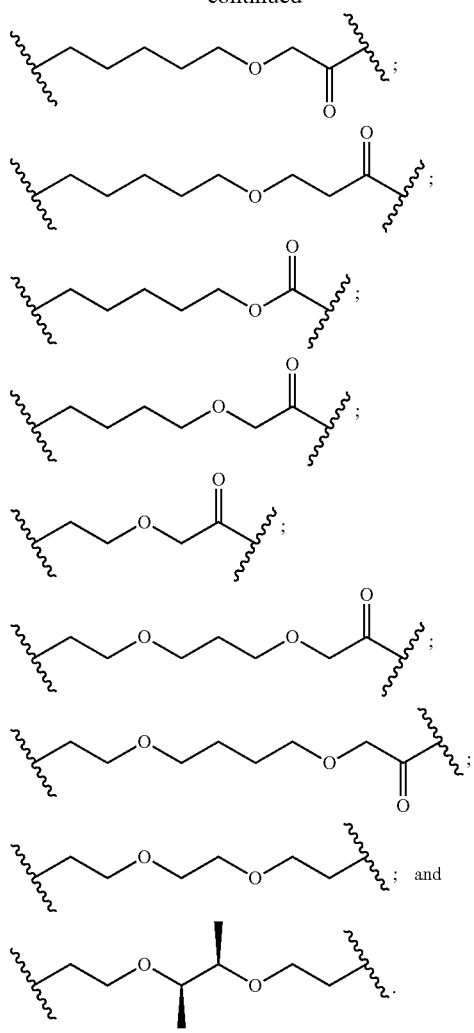

7. A composition comprising an effective amount of the bifunctional compound of claim 1, and a pharmaceutically acceptable carrier.

8. The composition of claim 7, wherein the composition further comprises at least one additional bioactive agent.

9. The composition of claim 8, wherein the bioactive agent is an anti-cancer agent.

10. The bifunctional compound of claim 3, wherein the ULM has the chemical structure:

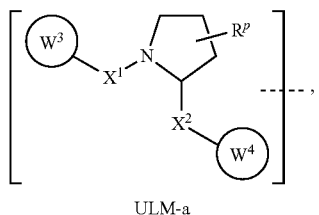

ULM-a wherein:
a dashed line indicates the attachment of the ULM to the chemical linker group or the TBM;
$X^1$, $X^2$ are each independently a bond, O, $NR^{Y3}$, $CR^{Y3}R^{Y4}$, C=O, C=S, SO, $SO_2$;

$R^{Y3}$, $R^{Y4}$ are each independently: H; or linear or branched $C_{1-6}$ alkyl optionally substituted by 1 or more halo or $C_{1-6}$;

$R^P$ is 0, 1, 2, or 3 groups in the pyrrolidine moiety, wherein each $R^P$ is independently H, halo, —OH, $C_{1-3}$ alkyl;

$W^3$ is an optionally substituted —T-N($R^{1a}R^{1b}$), —T-Aryl, an optionally substituted —T-Heteroaryl, an optionally substituted —T-Heterocycle, an optionally substituted —$NR^1$-T-Aryl, an optionally substituted -$NR^1$-T-Heteroaryl or an optionally substituted -$NR^1$-T-Heterocycle, where T is covalently bonded to $X^1$;

each $R^1$, $R^{1a}$, $R^{1b}$ is independently: H, a linear or branched $C_1$-$C_6$ alkyl group optionally substituted by 1 or more halo, or —OH; $R^{Y3}$C=O; $R^{Y3}$C=S; $R^{Y3}$SO; $R^{Y3}SO_2$; N($R^{Y3}R^{Y4}$)C=O; N($R^{Y3}R^{Y4}$)C=S; N($R^{Y3}R^{Y4}$)$SO_2$;

T is an optionally substituted —$(CH_2)_n$-group, wherein each one of the methylene groups may be optionally substituted with one or two substituents, selected from: halogen; a linear or branched Ci-C6 alkyl group optionally substituted by 1 or more halogen or OH; or the sidechain of an amino acid, which may be optionally substituted;

n is 0 to 6;
$W^4$ is

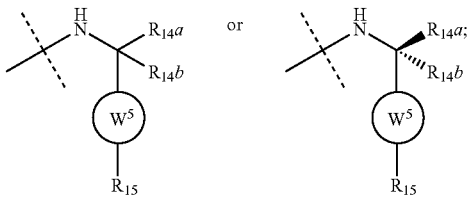

$R_{14a}$, $R_{14b}$, is each independently H, haloalkyl, or optionally substituted alkyl;
$W^5$ is a phenyl or a 5-10 membered heteroaryl; and
$R_{15}$ is H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, cycloheteroalkyl;.

11. The bifunctional compound of claim 1, wherein the compound has the chemical structure:

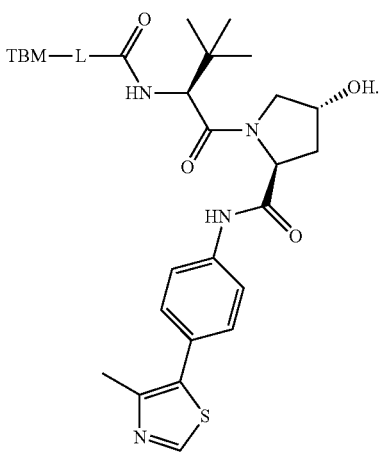

12. The bifunctional compound of claim 1, wherein the compound has the chemical structure:
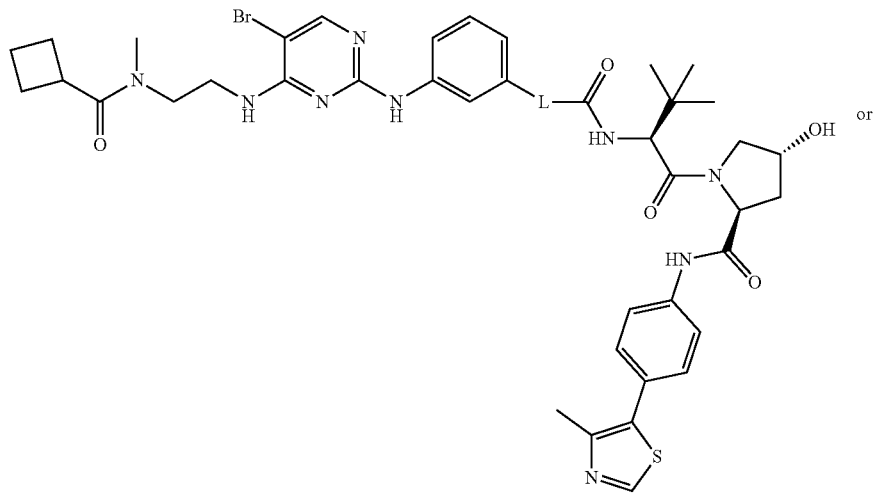
or
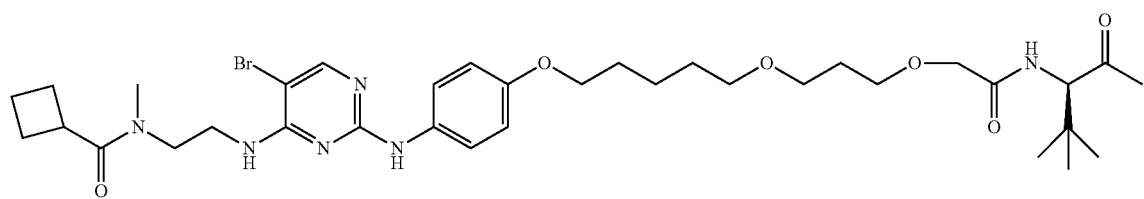
13. The bifunctional compound of claim 1, wherein the compound is selected from the group consisting of:

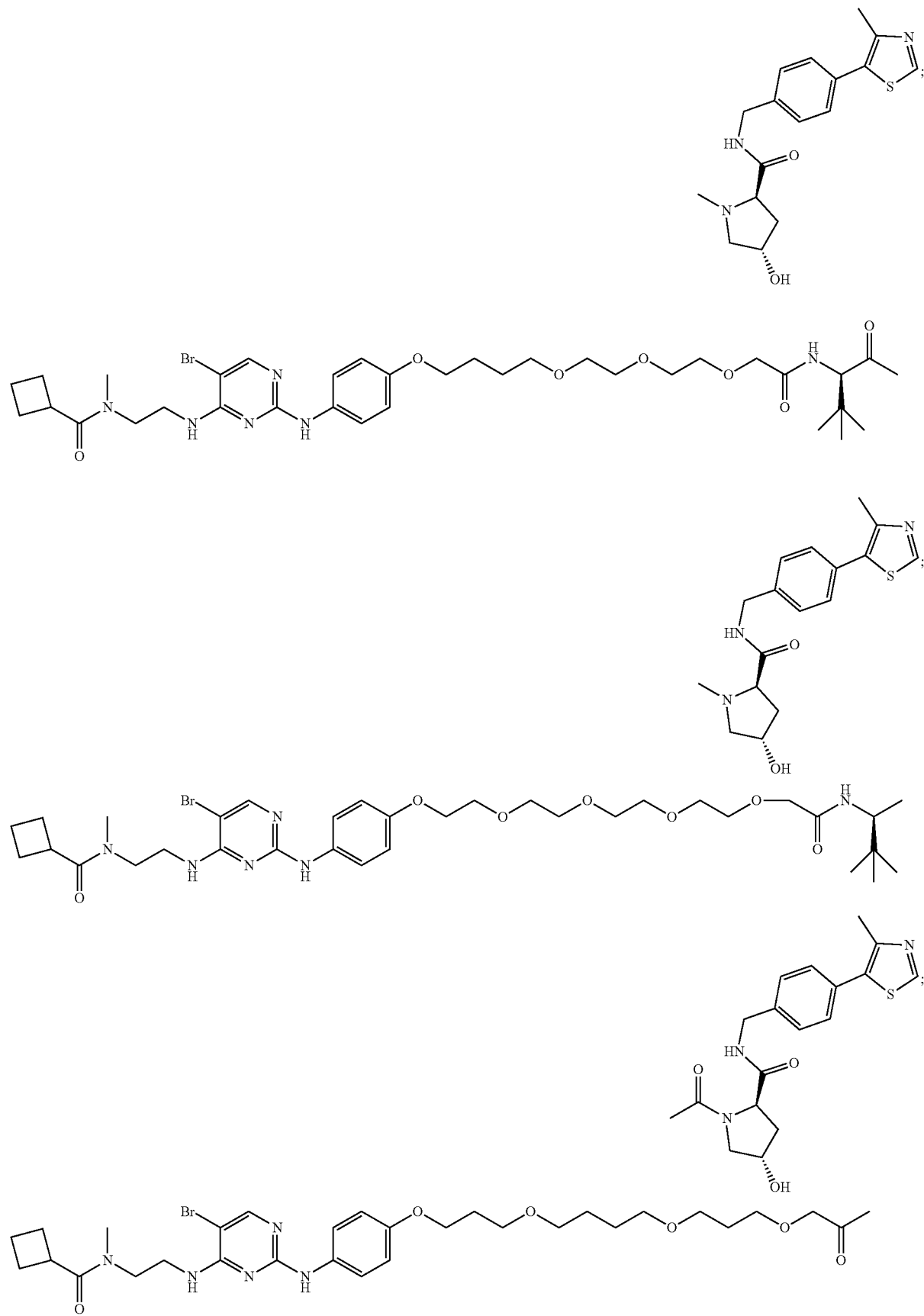

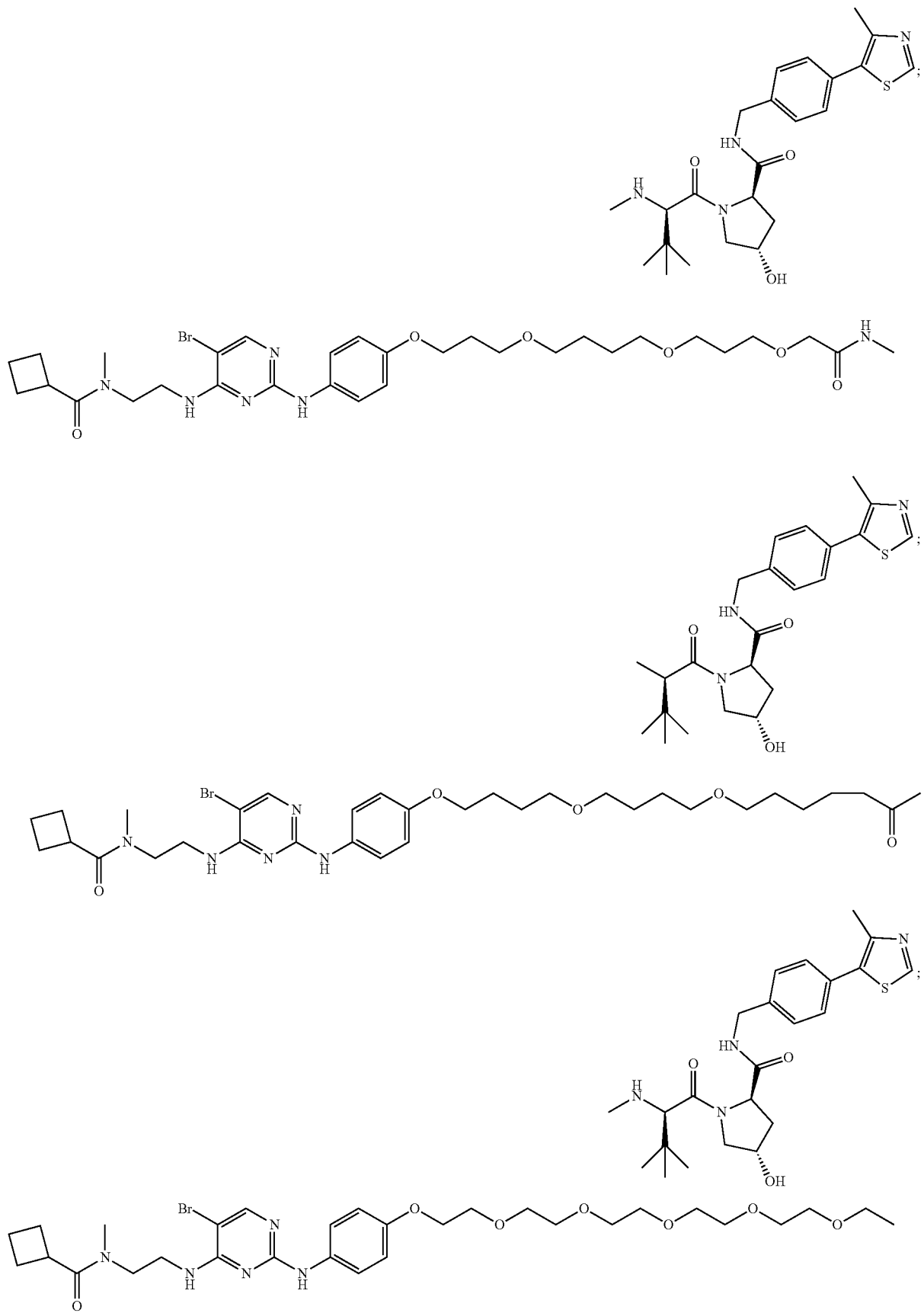

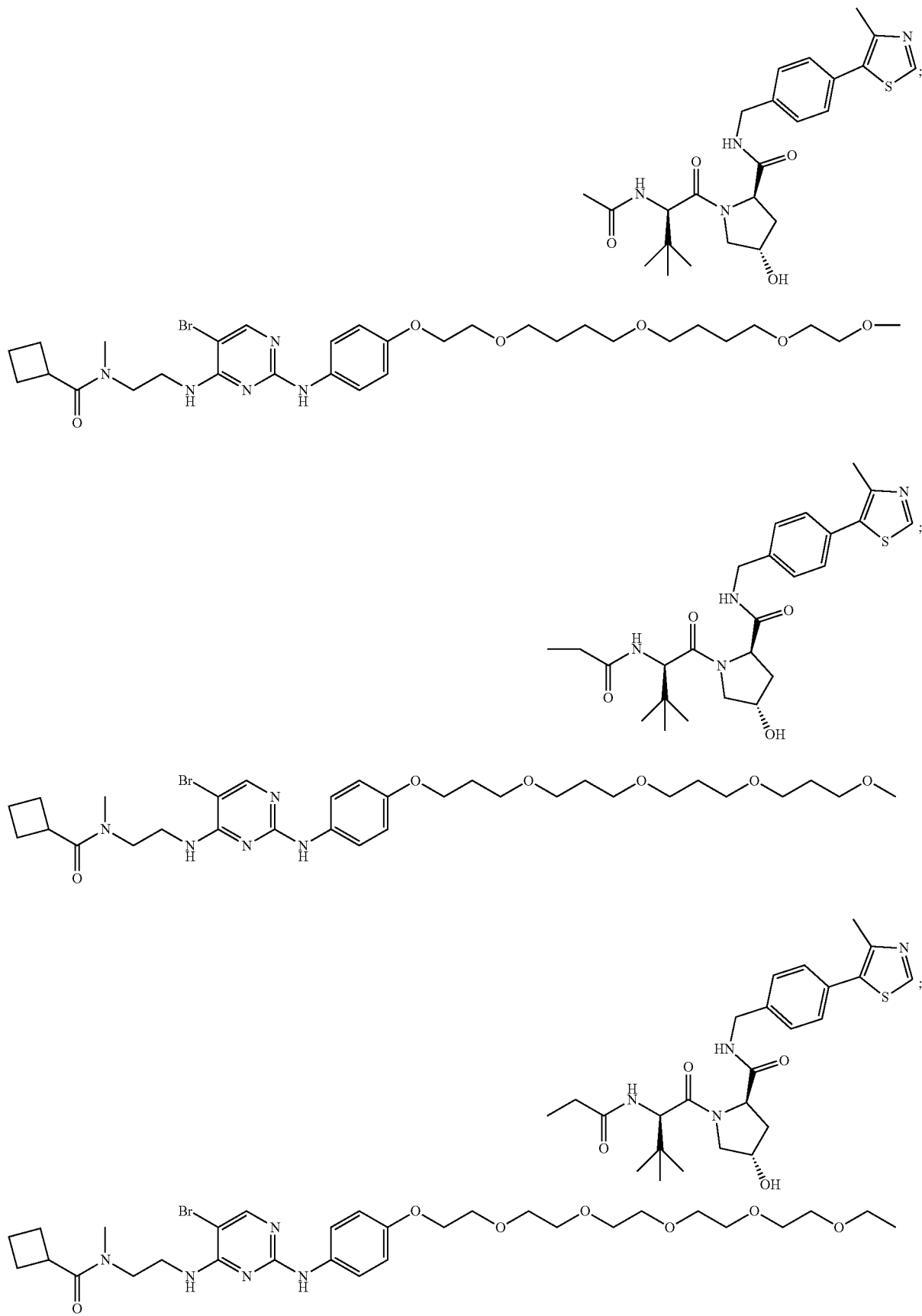

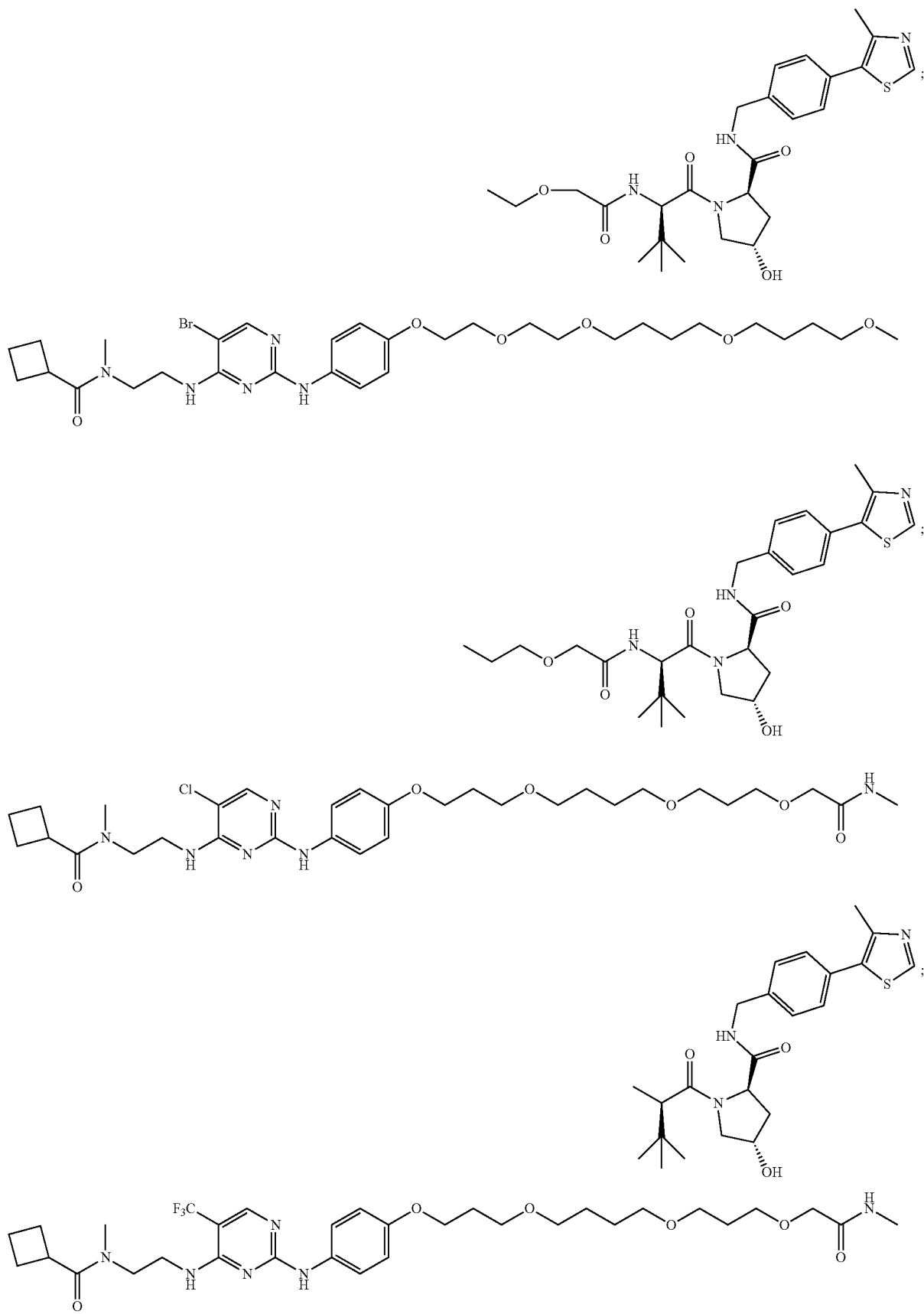

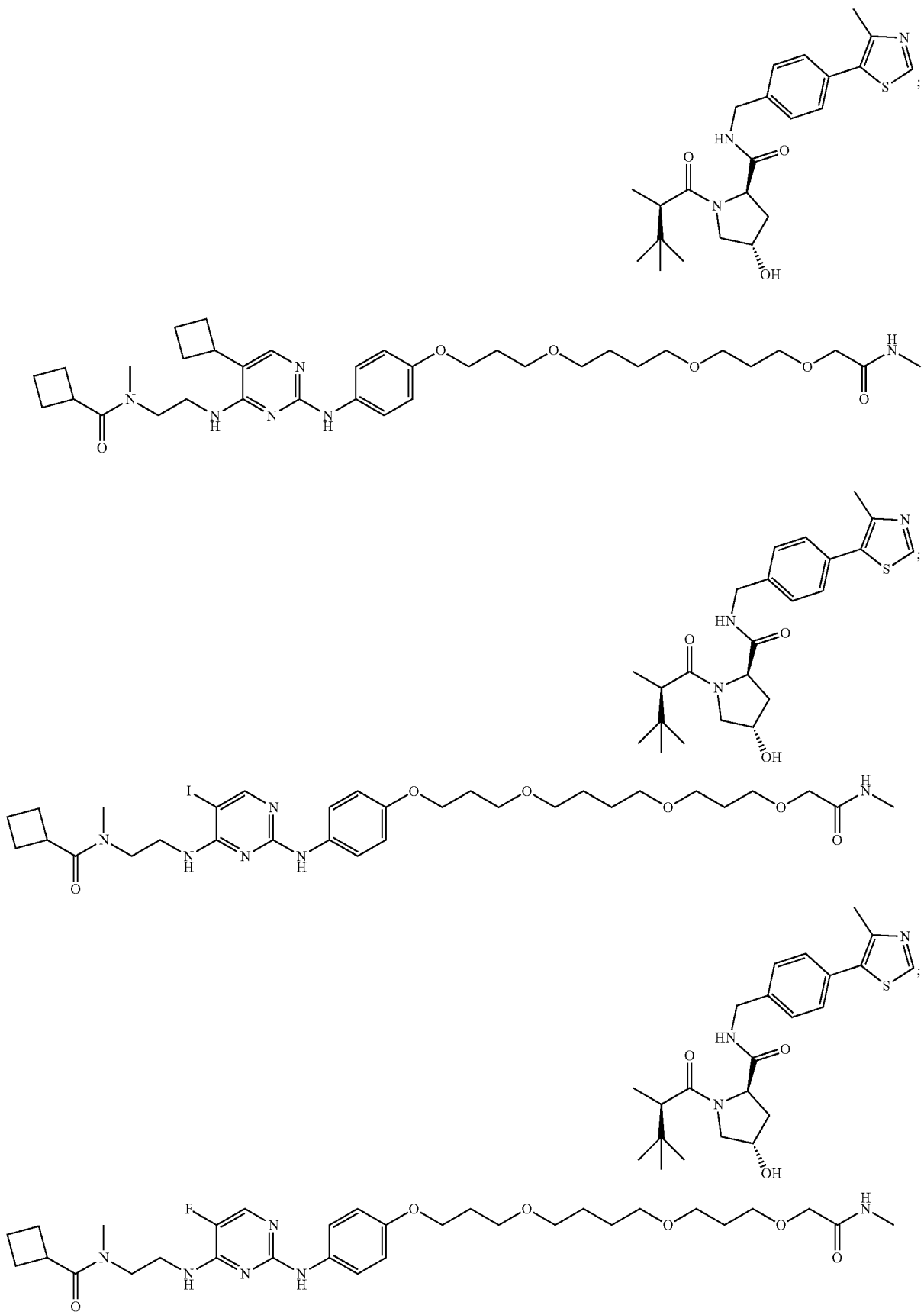

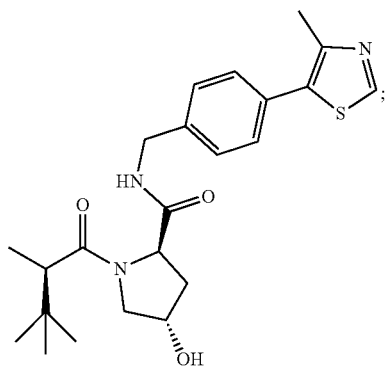
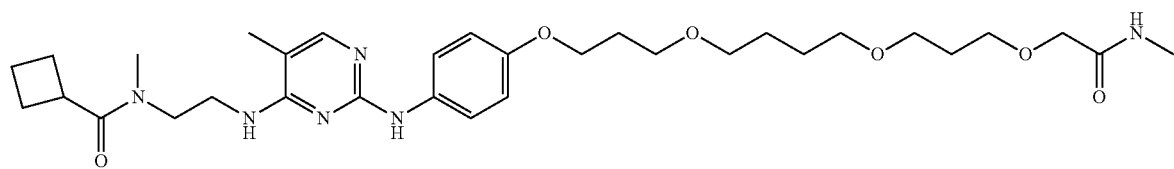
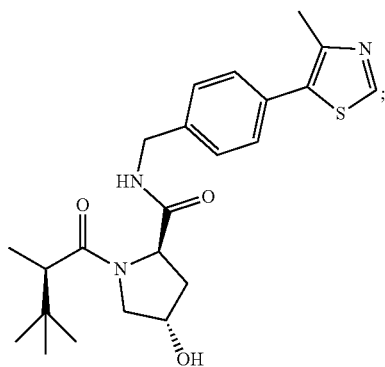
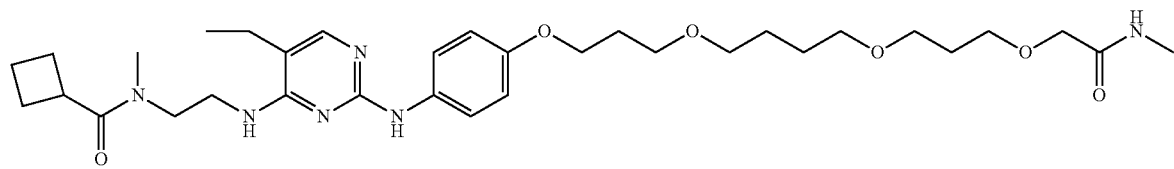
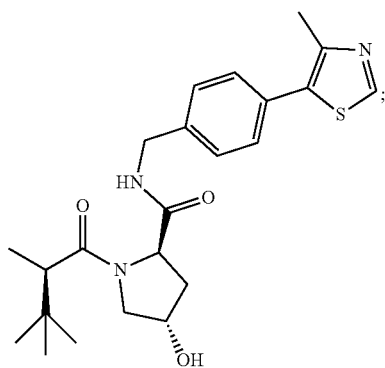
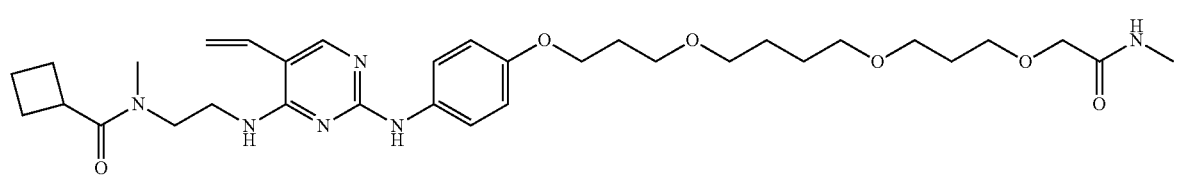

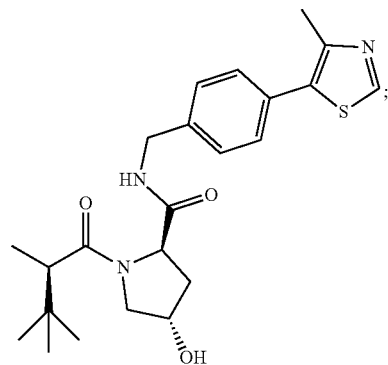
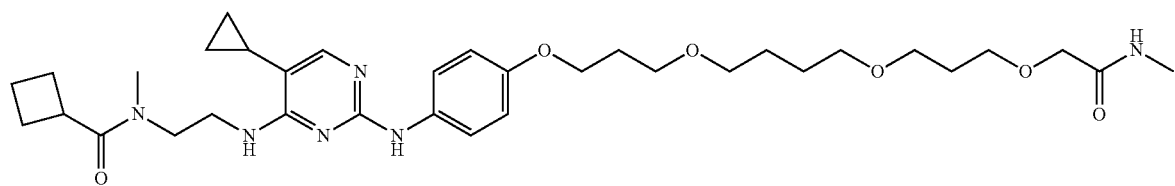
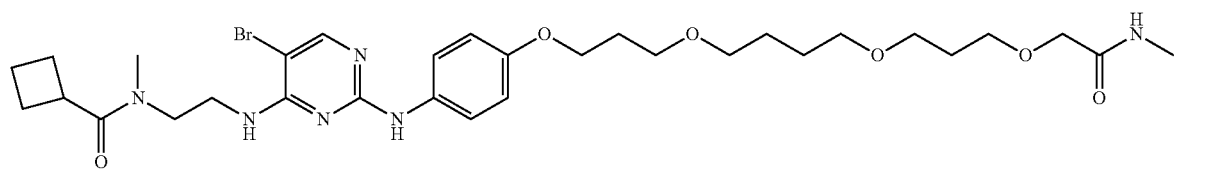
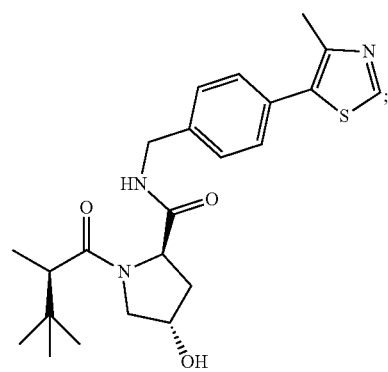

117
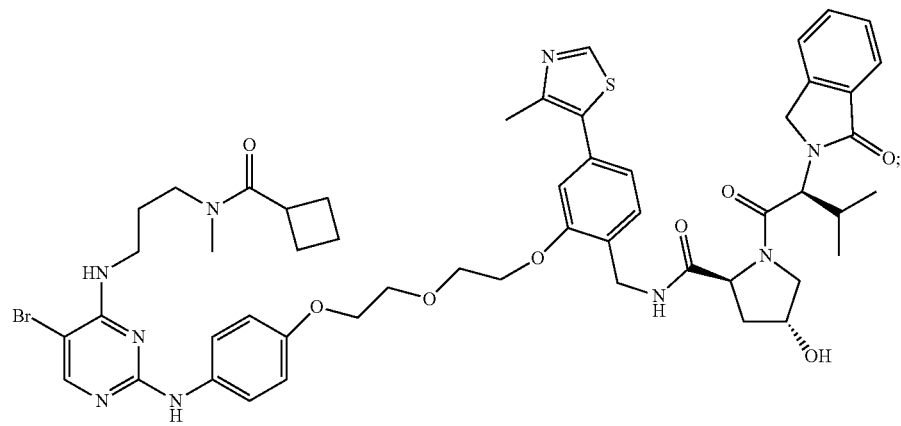
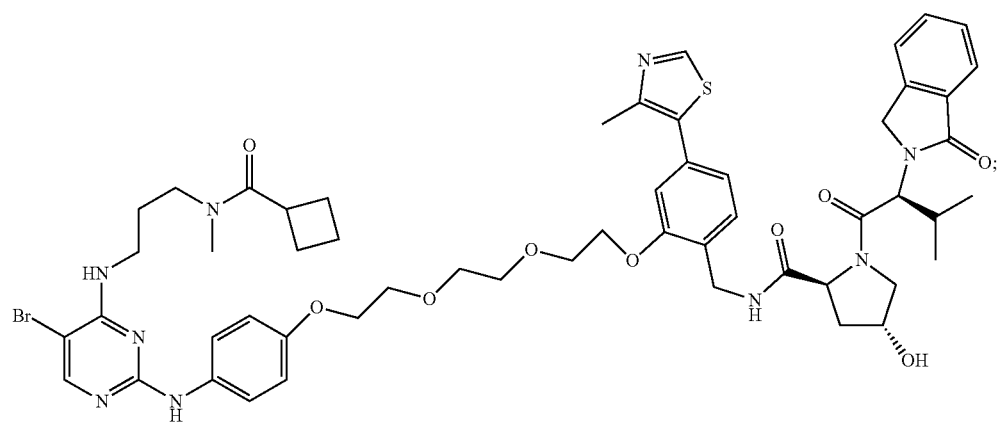
118
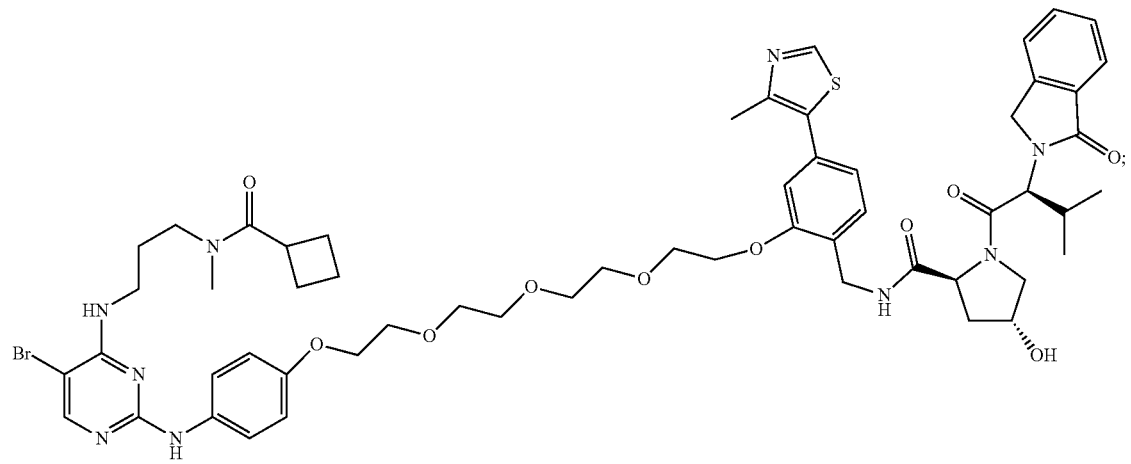

-continued
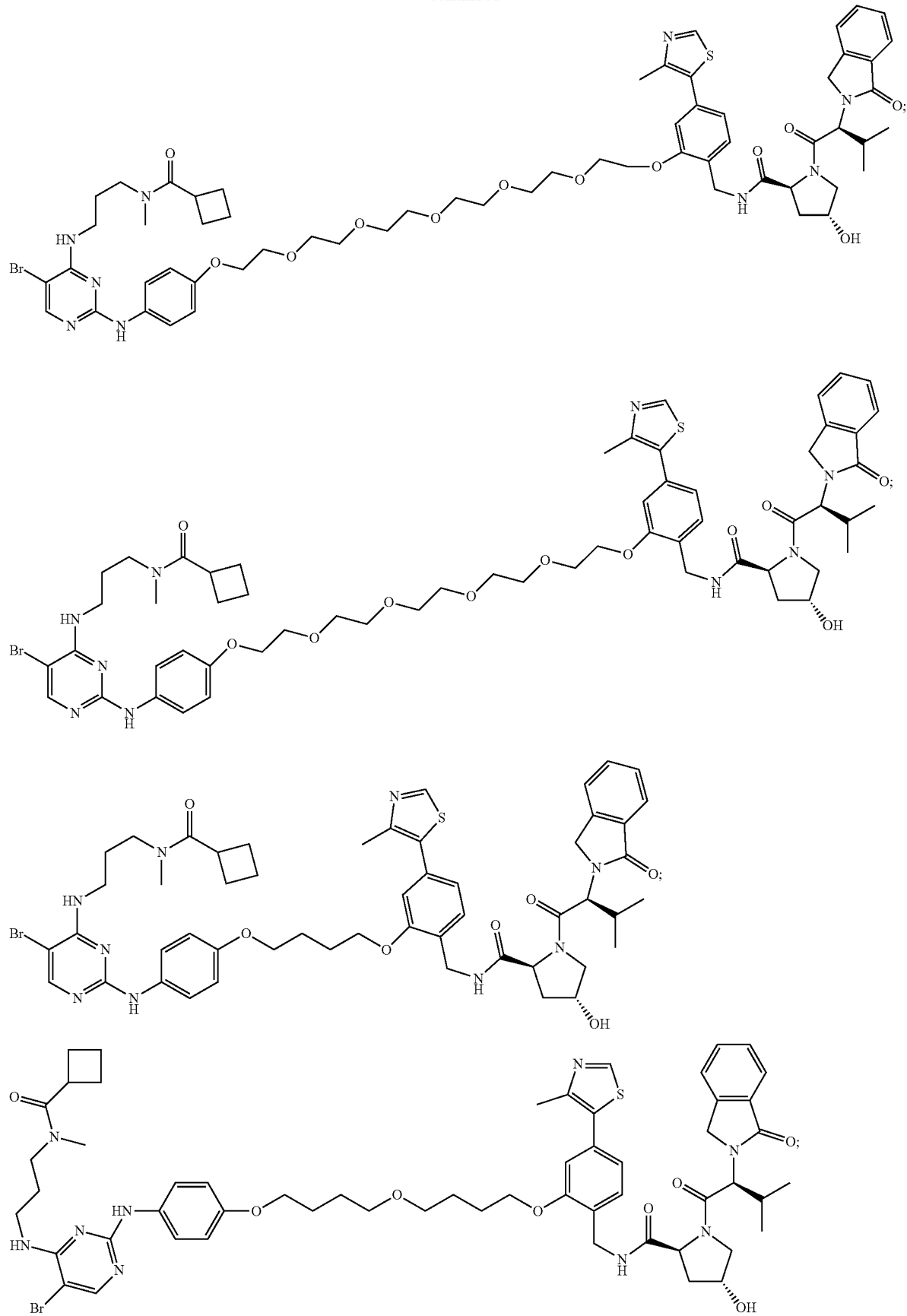

121
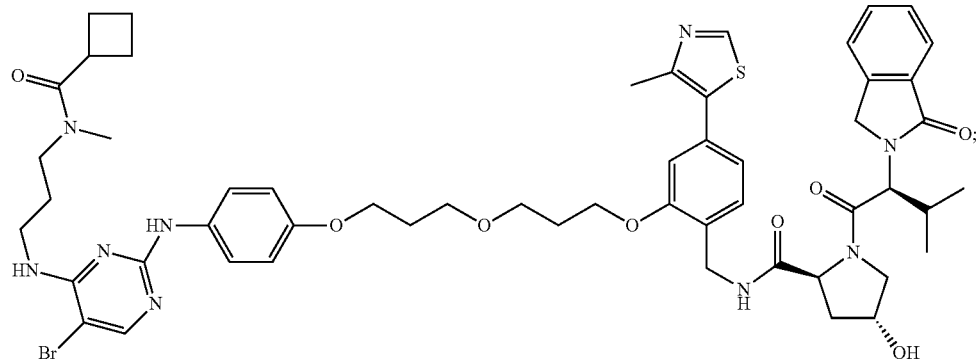
122
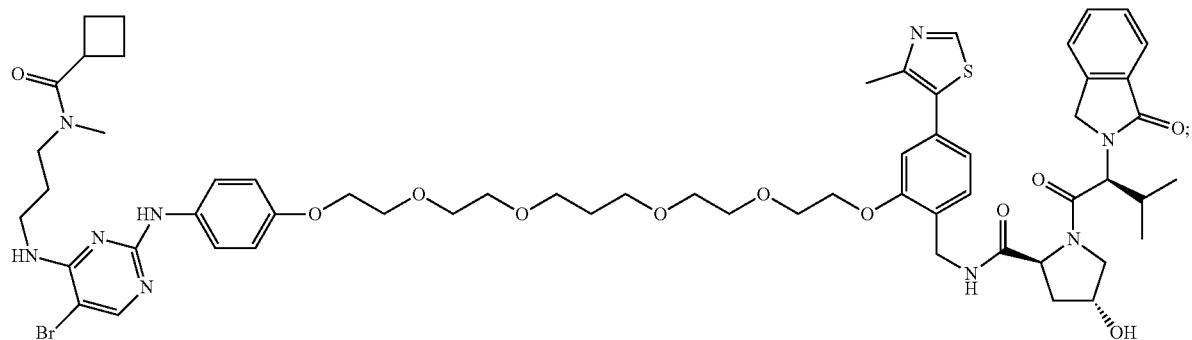
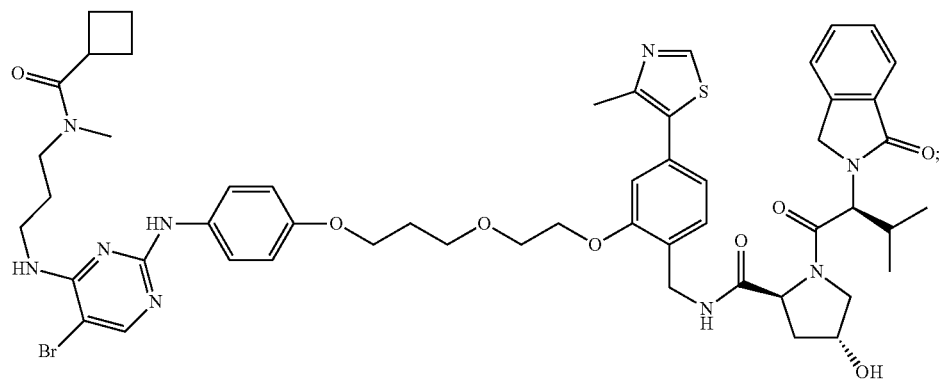
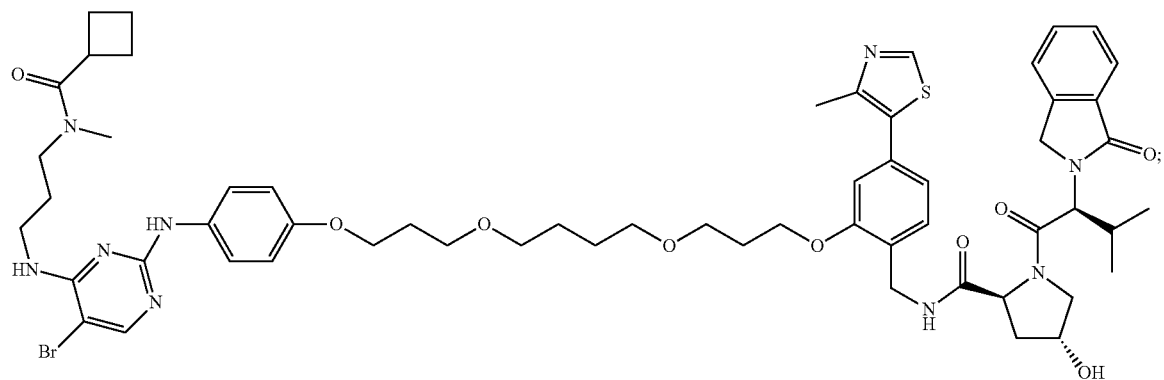

123 124
-continued
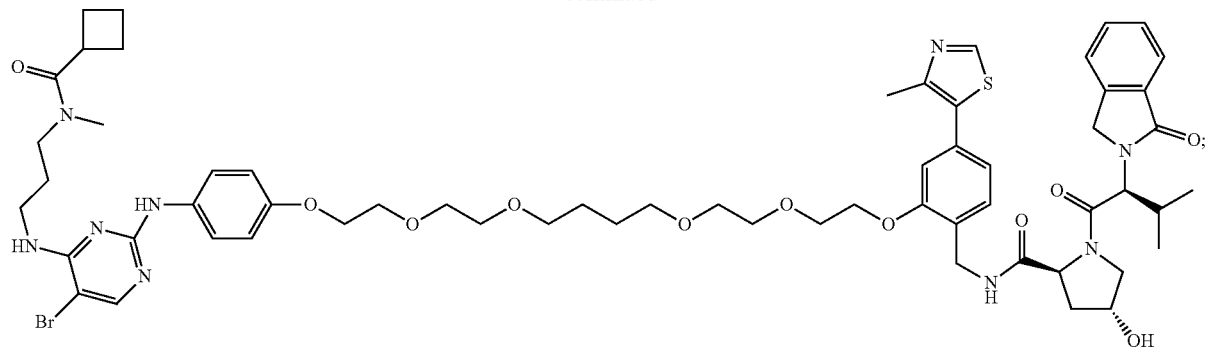
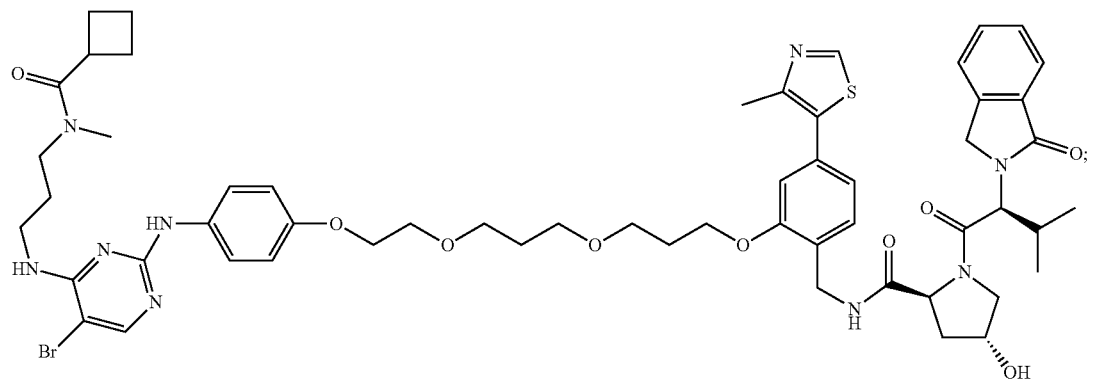
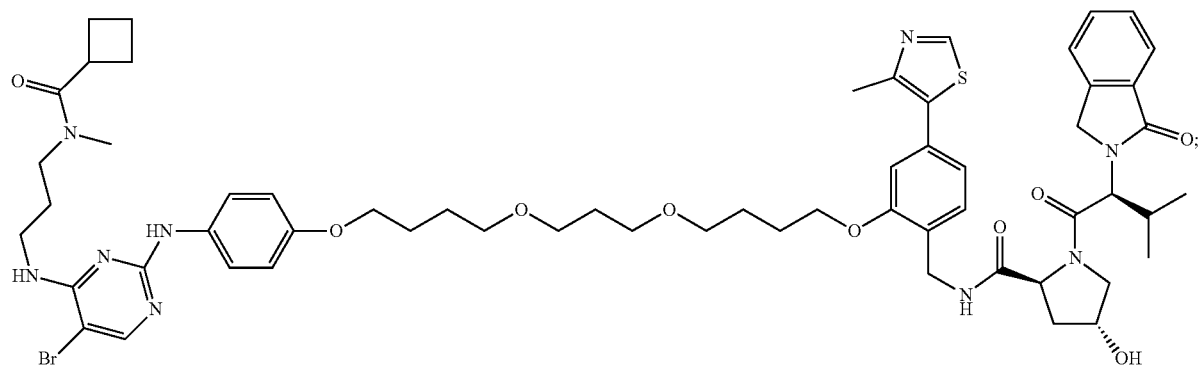
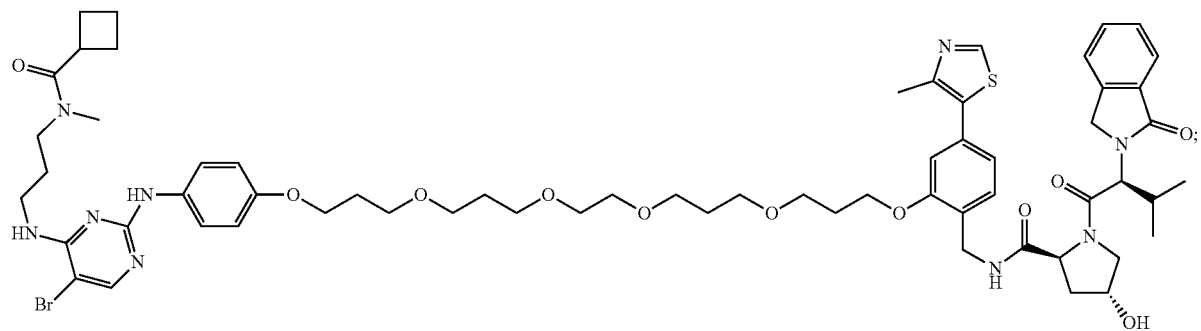

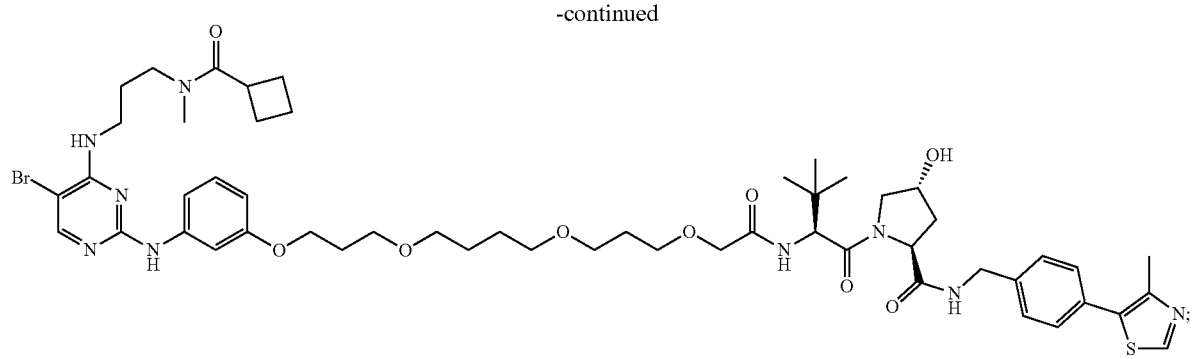
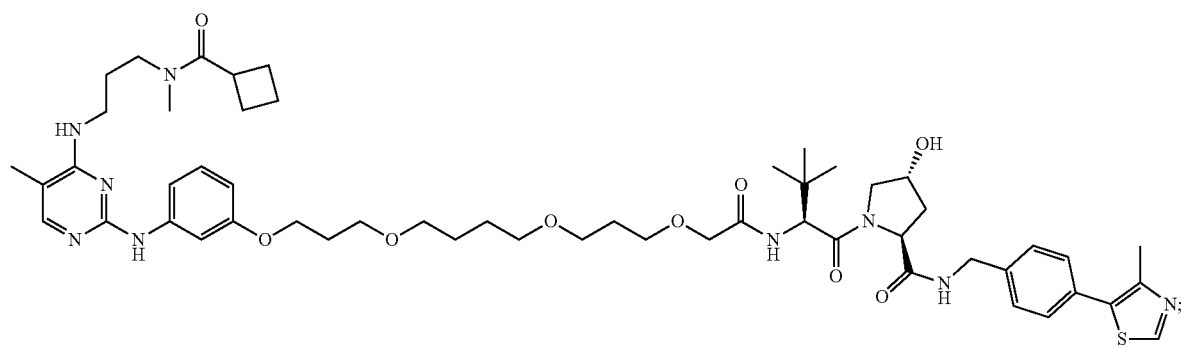
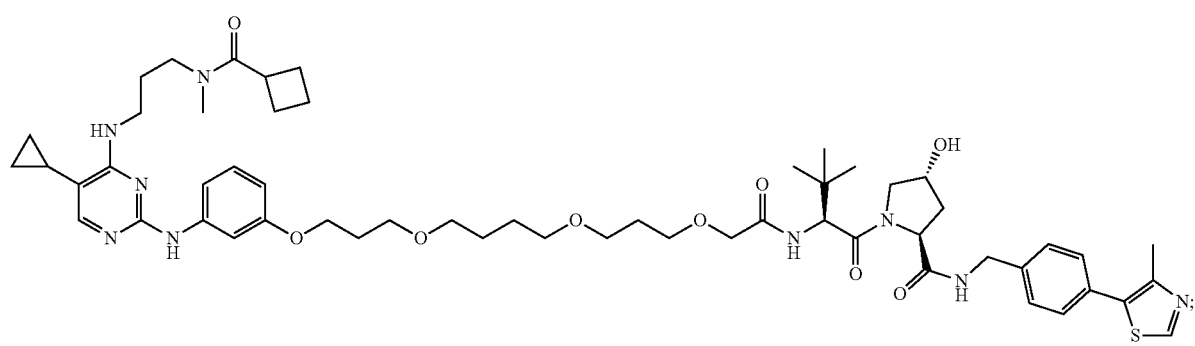
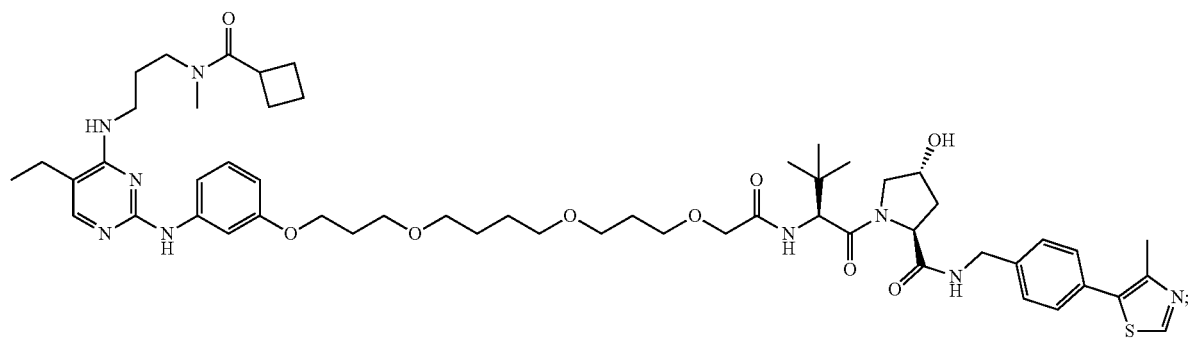
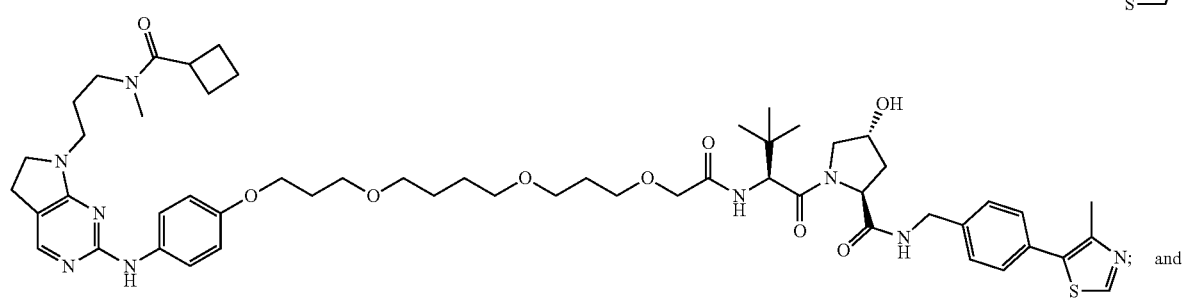

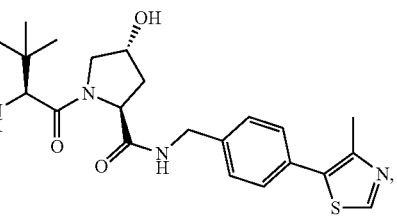

and combinations thereof.

14. The bifunctional compound of claim 1, wherein the ULM has a chemical structure selected the group consisting of:

(a) 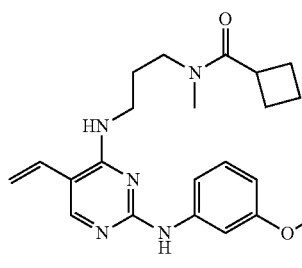

(b) 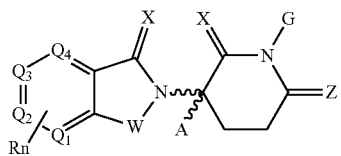

(c) 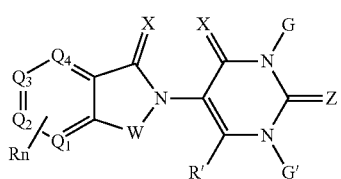

(d) 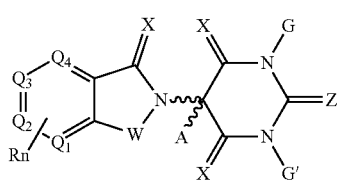

(e) 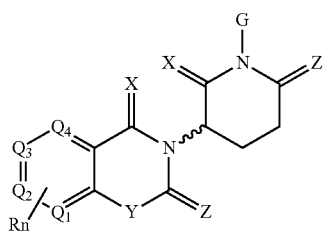 and (f) 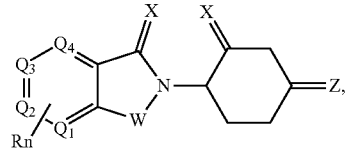

wherein:
W is independently selected from the group CH$_2$, CHR, C=O, SO$_2$, NH, and N-alkyl;
X is independently selected from the group absent, O and S;
Y is independently selected from the group NH, N-alkyl, N-aryl, N-hetaryl, N-cycloalkyl, N-heterocyclyl, O, and S;
Z is independently selected from the group absent, O and S, except that both X and Z cannot be absent;
G and G' are independently selected from the group H, alkyl, OH, CH$_2$-heterocyclyl optionally substituted with R', and benzyl optionally substituted with R';
Q1-Q4 represent a carbon C substituted with a group independently selected from H, R, N or N-oxide;
A is independently selected from the group H, alkyl, cycloalkyl, Cl and F;
R is: —CONR'R", —OR', —NR'R", —SR', —SO$_2$R', —SONR'R", —CR'R"—, —CR'NR'R"—, -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —CCR', —S(C=O)(C=N—R')R", —SF$_5$ and —OCF$_3$, wherein one R is modified to be covalently joined to the chemical linker group or the TBM:
R' and R" are independently selected from a bond, H, alkyl, cycloalkyl, aryl, hetaryl, heterocyclyl;
n is an integer from 1-4; and
∿∿ represents a bond that may be stereospecific ((R) or (S)) or non-stereospecific.

15. A composition comprising an effective amount of the compound of claim 13, and a pharmaceutically acceptable carrier.

16. The composition of claim 15, wherein the composition further comprises at least one additional bioactive agent.

17. A TBK1 binding moiety having the chemical structure:

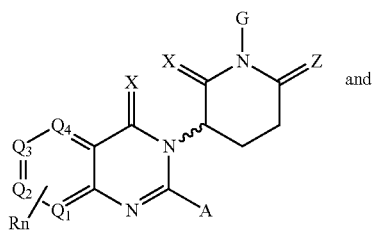

18. A method of making a bifunctional molecule comprising the chemical structure TBM-L-ULM, the method comprising:
  covalently linking the TBM to the L; and
  covalently linking the L to the ULM,
  wherein:
    the TBM is a TBK1 binding moiety,
    the L is a chemical linker that covalently couples the TBM and the ULM, and
    the ULM is an E3 ubiquitin ligase binding moiety.

19. A bifunctional compound comprising the chemical structure:

TBM-L-ULM, wherein:
  TBM includes a means for recruiting TBK1;
  L is a bond or a chemical linker that covalently couples the TBM and the ULM; and
  ULM includes a means for recruiting an E3 ubiquitin ligase.

20. The bifunctional compound of claim 1, wherein the TBM structure is represented by:

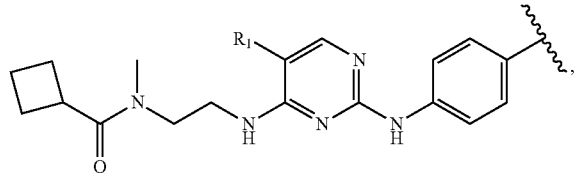

wherein $R_1$ is a group selected from Cl, $CF_3$, cyclobutyl, I, F, methyl, ethyl, vinyl, cyclopropyl, or Br.

21. The bifunctional compound of claim 1, wherein the ULM has the chemical structure:

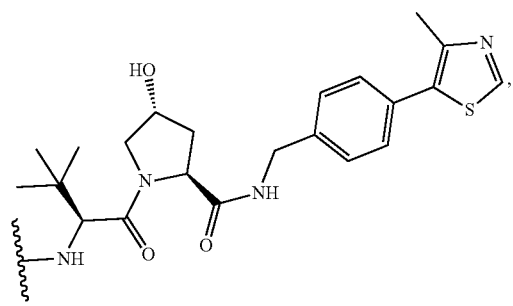

-continued

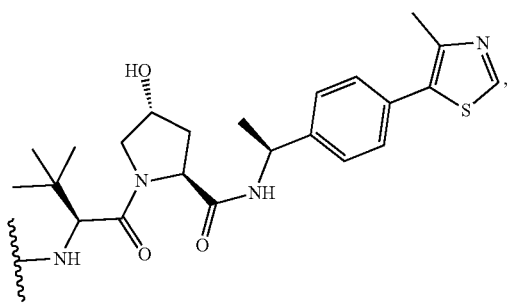

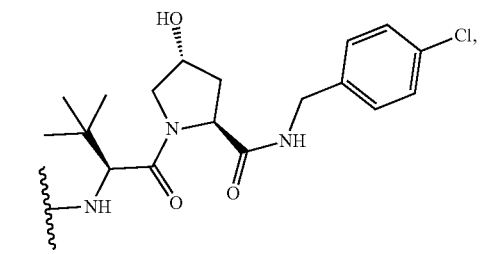

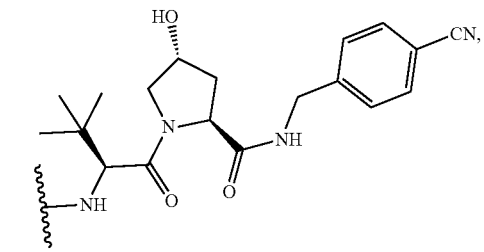

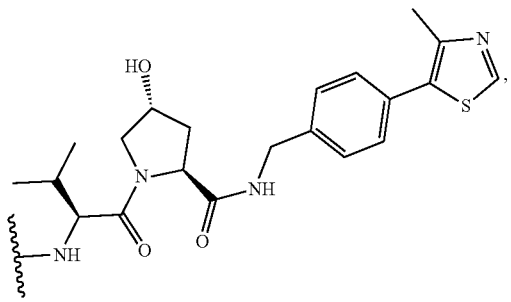

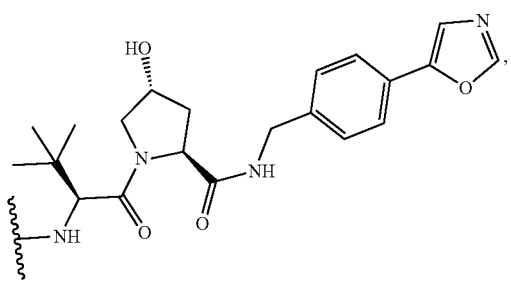

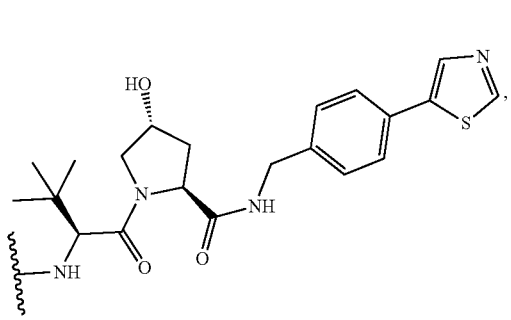

131
-continued
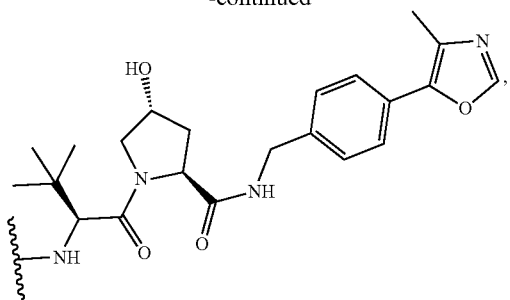
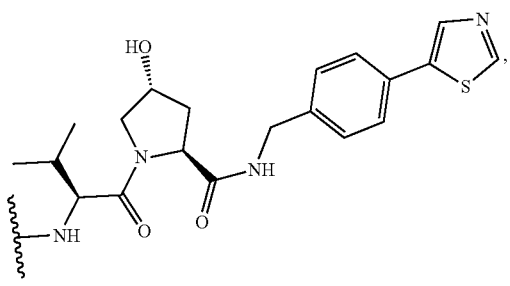
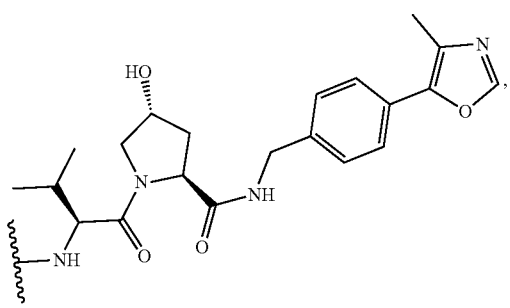
132
-continued
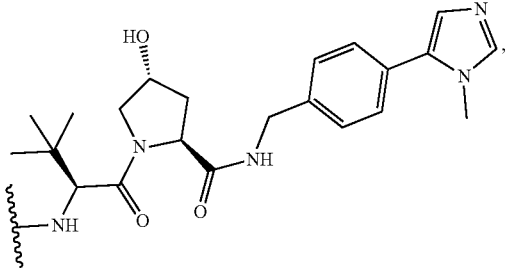
or
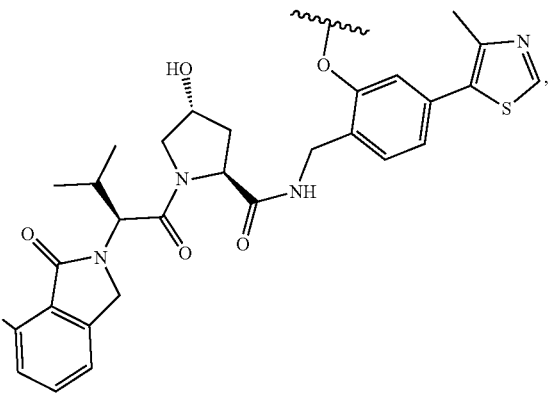
wherein
~~~
indicates the point of attachment to the chemical linker or the TBM.
* * * * *